United States Patent
Mason et al.

(10) Patent No.: US 11,635,434 B2
(45) Date of Patent: Apr. 25, 2023

(54) BETARETROVIRUS EPITOPES AND RELATED METHODS OF USE

(71) Applicants: Andrew L. Mason, Edmonton (CA); Mandana Rahbari, Edmonton (CA); Guangzhi Zhang, Edmonton (CA)

(72) Inventors: Andrew L. Mason, Edmonton (CA); Mandana Rahbari, Edmonton (CA); Guangzhi Zhang, Edmonton (CA)

( * ) Notice: Subject to any disclaimer, the term of this patent is extended or adjusted under 35 U.S.C. 154(b) by 476 days.

(21) Appl. No.: 16/681,494

(22) Filed: Nov. 12, 2019

(65) Prior Publication Data

US 2020/0166511 A1    May 28, 2020

Related U.S. Application Data

(60) Provisional application No. 62/758,823, filed on Nov. 12, 2018.

(51) Int. Cl.
| | | |
|---|---|---|
| G01N 33/574 | (2006.01) | |
| A61K 35/17 | (2015.01) | |
| G01N 33/68 | (2006.01) | |
| A61K 45/06 | (2006.01) | |
| C07K 14/195 | (2006.01) | |
| A61K 38/00 | (2006.01) | |

(52) U.S. Cl.
CPC ....... *G01N 33/57426* (2013.01); *A61K 35/17* (2013.01); *C07K 14/195* (2013.01); *G01N 33/6893* (2013.01); *A61K 38/00* (2013.01); *A61K 45/06* (2013.01); *G01N 2333/525* (2013.01); *G01N 2333/57* (2013.01)

(58) Field of Classification Search
None
See application file for complete search history.

(56) References Cited

PUBLICATIONS

Xu, L. et al., "Does a Betaretrivirus Infection Trigger Primary Biliary Cirrhosis?"; PNAS (2003); vol. 100:14; pp. 3454-8459.

*Primary Examiner* — Nicole Kinsey White
(74) *Attorney, Agent, or Firm* — Fox Rothschild LLP

(57) ABSTRACT

Methods for determination of risk, previous history and/or presence of a betaretrovirus infection in a subject are described herein. Said methods may comprise incubating a biological sample from the subject, the biological sample comprising immune effector-producing cells, with one or more betaretrovirus-specific epitopes, the betaretrovirus-specific epitopes comprising at least 7 contiguous amino acids according to any one of SEQ ID Nos. 1-36, and measuring the production of immune effectors by the immune effector-producing cells, wherein production of the immune effectors by the immune effector-producing cells determines risk and/or presence of betaretrovirus infection in the subject. Isolated peptides and kits for carrying out the methods are also described.

16 Claims, 30 Drawing Sheets

Specification includes a Sequence Listing.

FIGURE 4C

C Stimulate lymphocytes 6 hr
- Nil (-ve control)
- PMA/Ionomycin (+ve control)
- Gag peptide pool
- Env peptide pool (+/- ISD)
- PDC-E2 peptide
- Peptide mapping with individual Gag and Env peptides FIG. 4D
Measure cytokines (IFN-γ and TNF-α)
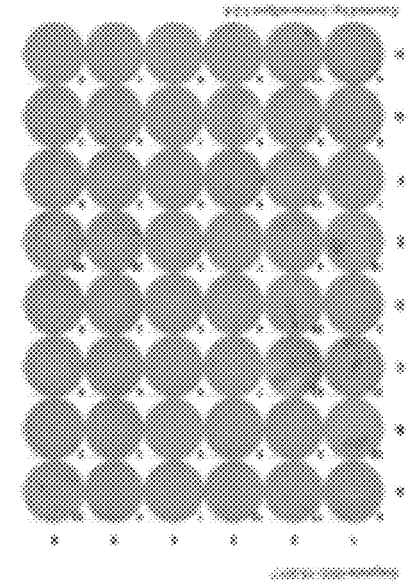
FACS
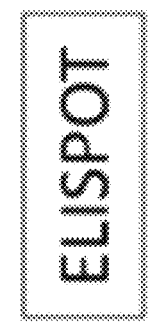
ELISPOT
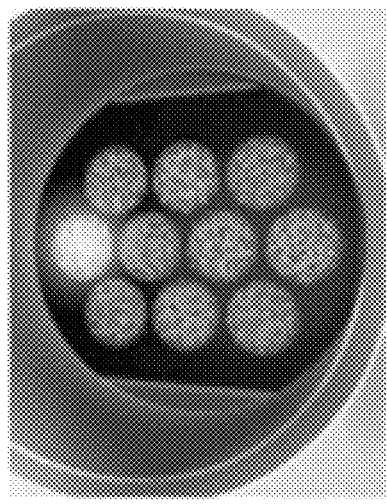
ELISA

FIGURE 8

HBRV envelope coding sequence (1362 bp, primers underlined) – SEQ ID NO: 148

<u>atgccgaatcaccaatctgggtccccgaccggttcatccgacctttt</u>actgagcggaaagaagcaacgcccacacctggcactgcgga
gaaaacgccgcagcgagatgagaaagatcaacaggaaagtccggaggatgaatctagccccatcaaagagaagacggcttggca
acatctgcaggcgttaatcttcgaagcggaggaggttcttaaaacctcacaaactccccaaacctctttgactttatttcttgctttgttgtct
gtcctcggccccccgcctgtgaccggggaaagttattgggcttacctacctaaaccacctattctccatcccgtgggatggggaaatac
agacccattagagttctgaccaatcaaaccatatatttgggtgggtcacctgactttcacgggtttagaaacatgtctggcaatgtacattt
tgaggggaagtctgatacgctccccatttgcttttccttctccttttctaccccacaggctgctttcaagtagataagcaagtatttctttctg
atacacccgcggttgataataataaacctgggggaaagggtgataaaaggcgtatgtgggaactttggttgactactttggggaactca
ggggccaatacaaaactggtccctataaaaaagaagttgcccccaatatcctcactgccagatcgcctttaagaaggacgccttctg
ggagggagacgagtctgctcctccacgtggttgccttgcgccttccctgaccagggggtgagttttctccaaaagggacccttgggt
tactttgggatttctccttccctcgcctagtgtagatcagtcagatcagattagaagcaaaaaggatctatttggaaattatactcccctgt
caataaagaggttcatcgatggtatgaagcaggatgggtagaacgtacatggttctgggaaattctcctaaggatcccaatgatagag
attttactgctctagttccccatacagaattgtttcgcttagttgcagcctcaagatatcttattctcaaaaggccaggatttcaagaacatga
catgattcctacatctgcctgtgctacttacccttatgccatattattaggattacctcagctaatagatatagagaaaagaggatctactttc
atatttcctgttcttcttgtagattgactaattgtttagattcttctgcctacgactatgcagcgatcatagtcaagaggccgccatacgtgctg
ctacctgtagatattggtgatgaaccatggtttgatgattctgccattctaacctttagg<u>tatgccacagatttaattcgagcc</u> (SEQ ID
NO: 148)

HBRV SU protein sequence (SEQ ID NO: 147)

MPNHQSGSPTGSSDLLLSGKKQRPHLALRRKRRSEMRKINRKVRRMNLAPIKEKTA
WQHLQALIFEAEEVLKTSQTPQTSLTLFLALLSVLGPPPVTGESYWAYLPKPPILHPVG
WGNTDPIRVLTNQTIYLGGSPDFHGFRNMSGNVHFEGKSDTLPICFSFSFSTPTGCFQV
DKQVFLSDTPAVDNNKPGGKGDKRRMWELWLTTLGNSGANTKLVPIKKKLPPKYP
HCQIAFKKDAFWEGDESAPPRWLPCAFPDQGVSFSPKGTLGLLWDFSLPSPSVDQSD
QIRSKKDLFGNYTPPVNKEVHRWYEAGWVERTWFWENSPKDPNDRDFTALVPHTEL
FRLVAASRYLILKRPGFQEHDMIPTSACATYPYAILLGLPQLIDIEKRGSTFHISCSSCR
LTNCLDSSAYDYAAIIVKRPPYVLLPVDIGDEPWFDDSAILTFRYATDLIRA (SEQ ID
NO: 147).

FIGURE 12
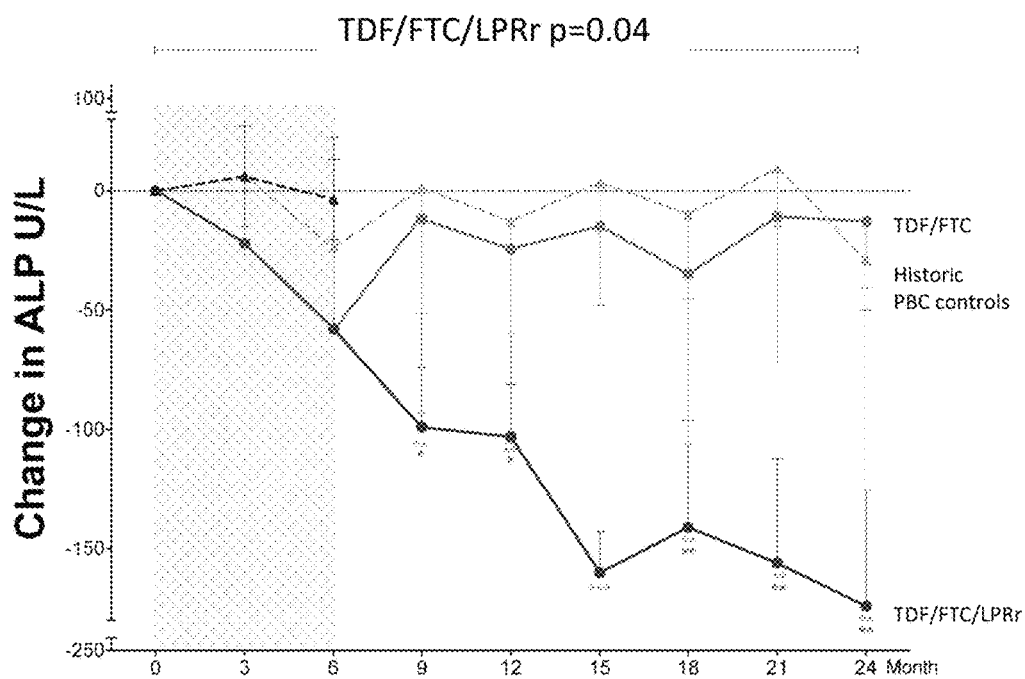
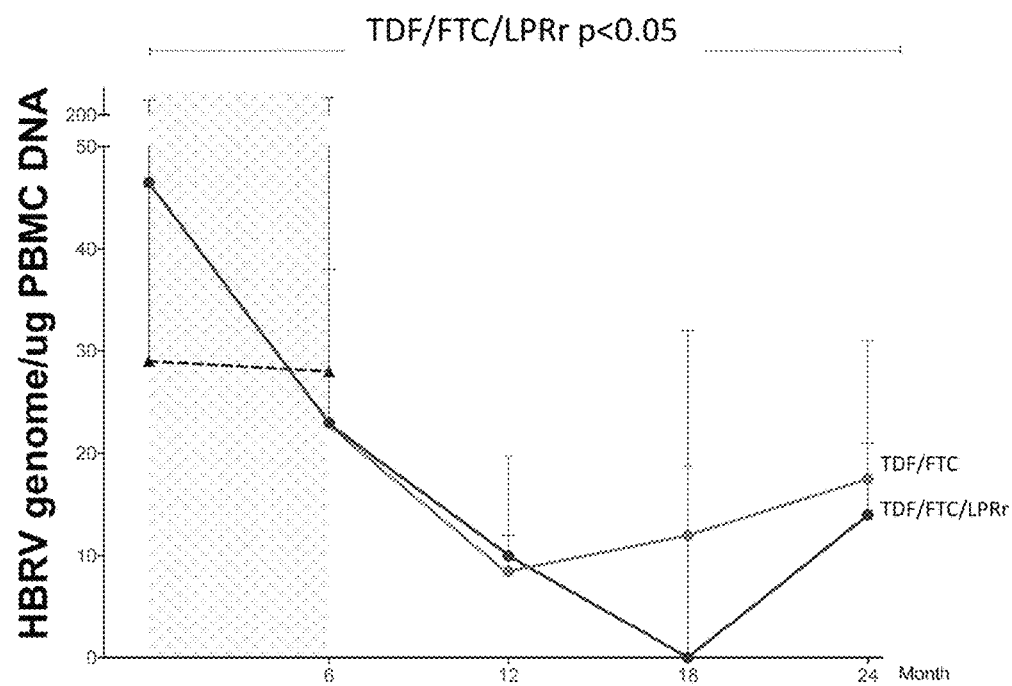

FIG. 15B
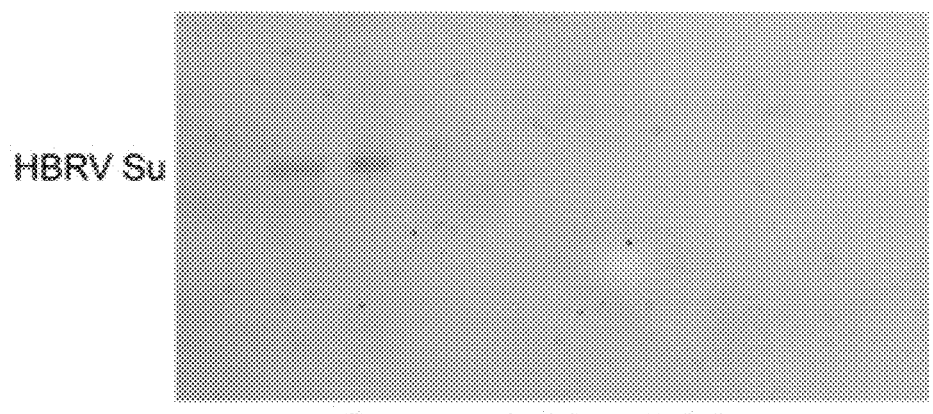
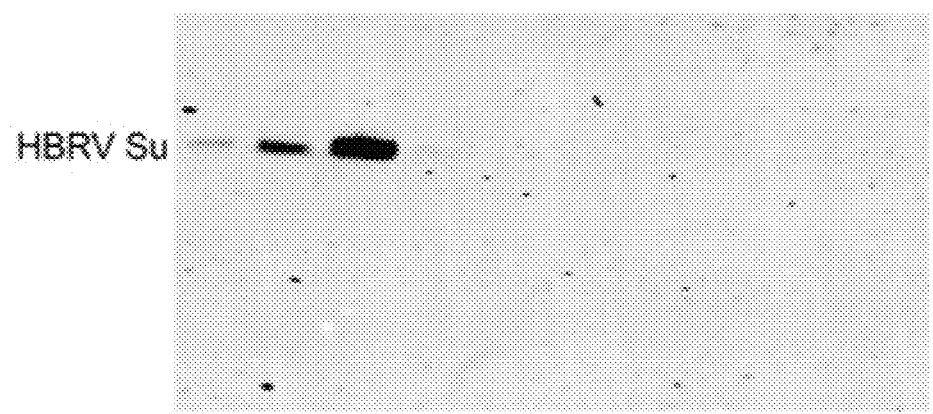
FIG. 15C
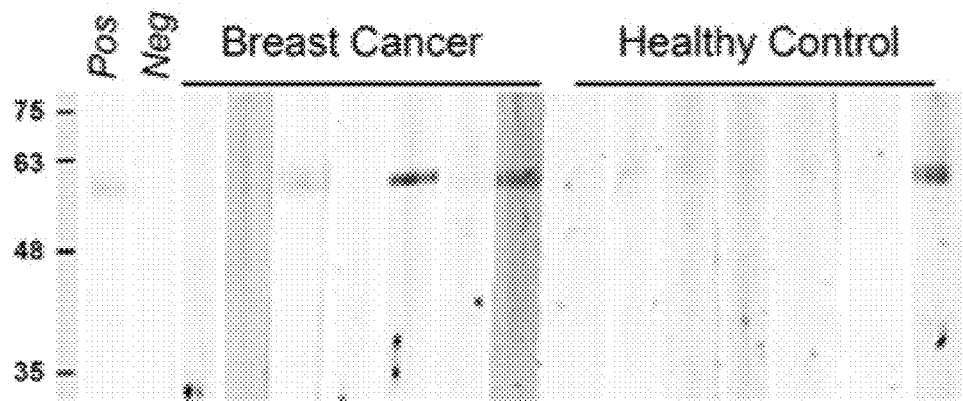

SEQUENCE LISTING

```
<160> NUMBER OF SEQ ID NOS: 154

<210> SEQ ID NO 1
<211> LENGTH: 20
<212> TYPE: PRT
<213> ORGANISM: Artificial Sequence
<220> FEATURE:
<223> OTHER INFORMATION: Gag 9

<400> SEQUENCE: 1

Tyr Pro Ile Trp Leu Gln Leu Arg Glu Ile Leu Thr Glu Gln Ser Asp
1               5                   10                  15

Leu Val Leu Leu
            20

<210> SEQ ID NO 2
<211> LENGTH: 20
<212> TYPE: PRT
<213> ORGANISM: Artificial Sequence
<220> FEATURE:
<223> OTHER INFORMATION: Gag 27

<400> SEQUENCE: 2

Glu Lys Gly Asp Leu Thr Phe Thr Phe Pro Val Val Phe Met Gly Glu
1               5                   10                  15

Ser Asp Asp Asp
            20

<210> SEQ ID NO 3
<211> LENGTH: 20
<212> TYPE: PRT
<213> ORGANISM: Artificial Sequence
<220> FEATURE:
<223> OTHER INFORMATION: Gag 40

<400> SEQUENCE: 3

Leu Lys Asp Val Thr Thr Asn Ala Val Leu Ala Trp Arg Ala Ile Pro
1               5                   10                  15

Pro Pro Gly Val
            20

<210> SEQ ID NO 4
<211> LENGTH: 20
<212> TYPE: PRT
<213> ORGANISM: Artificial Sequence
<220> FEATURE:
<223> OTHER INFORMATION: Gag 1

<400> SEQUENCE: 4

Met Gly Val Ser Gly Ser Lys Gly Gln Lys Leu Phe Val Ser Val Leu
1               5                   10                  15

Gln Arg Leu Leu
            20
```

```
<210> SEQ ID NO 5
<211> LENGTH: 20
<212> TYPE: PRT
<213> ORGANISM: Artificial Sequence
<220> FEATURE:
<223> OTHER INFORMATION: Gag 3

<400> SEQUENCE: 5

Ser Glu Arg Gly Leu His Val Lys Glu Ser Ser Ala Ile Glu Phe Tyr
1               5                   10                  15

Gln Phe Leu Ile
            20

<210> SEQ ID NO 6
<211> LENGTH: 20
<212> TYPE: PRT
<213> ORGANISM: Artificial Sequence
<220> FEATURE:
<223> OTHER INFORMATION: Gag 25

<400> SEQUENCE: 6

Ala Leu Arg Arg Lys Pro Leu Pro Val Gly Phe Ala Gly Ala Met
1               5                   10                  15

Ala Glu Ala Arg
            20

<210> SEQ ID NO 7
<211> LENGTH: 20
<212> TYPE: PRT
<213> ORGANISM: Artificial Sequence
<220> FEATURE:
<223> OTHER INFORMATION: Gag 26

<400> SEQUENCE: 7

Gly Phe Ala Gly Ala Met Ala Glu Ala Arg Glu Lys Gly Asp Leu Thr
1               5                   10                  15

Phe Thr Phe Pro
            20

<210> SEQ ID NO 8
<211> LENGTH: 20
<212> TYPE: PRT
<213> ORGANISM: Artificial Sequence
<220> FEATURE:
<223> OTHER INFORMATION: Gag 33

<400> SEQUENCE: 8

Trp Leu Thr Pro Ser Asp Trp His Gln Thr Ala Arg Ala Thr Leu Ser
1               5                   10                  15

Pro Gly Asp Tyr
            20

<210> SEQ ID NO 9
<211> LENGTH: 20
<212> TYPE: PRT
<213> ORGANISM: Artificial Sequence
<220> FEATURE:
<223> OTHER INFORMATION: Gag 37

<400> SEQUENCE: 9

Lys Arg Lys Gly Lys Val Ser Leu Asp Met Leu Leu Gly Thr Gly Gln
1               5                   10                  15

Phe Leu Ser Pro
            20
```

-continued

```
<210> SEQ ID NO 10
<211> LENGTH: 20
<212> TYPE: PRT
<213> ORGANISM: Artificial Sequence
<220> FEATURE:
<223> OTHER INFORMATION: Gag 42

<400> SEQUENCE: 10

Lys Lys Thr Val Leu Ala Gly Leu Lys Gln Gly Asn Glu Glu Ser Tyr
1               5                   10                  15

Glu Thr Phe Ile
            20

<210> SEQ ID NO 11
<211> LENGTH: 20
<212> TYPE: PRT
<213> ORGANISM: Artificial Sequence
<220> FEATURE:
<223> OTHER INFORMATION: Gag 43

<400> SEQUENCE: 11

Gly Asn Glu Glu Ser Tyr Glu Thr Phe Ile Ser Arg Leu Glu Glu Ala
1               5                   10                  15

Val Tyr Arg Met
            20

<210> SEQ ID NO 12
<211> LENGTH: 20
<212> TYPE: PRT
<213> ORGANISM: Artificial Sequence
<220> FEATURE:
<223> OTHER INFORMATION: Gag 51

<400> SEQUENCE: 12

Arg Gly Gln Lys Tyr Ser Thr Leu Val Lys Gln Thr Tyr Gly Gly Gly
1               5                   10                  15

Lys Gly Gly Gln
            20

<210> SEQ ID NO 13
<211> LENGTH: 20
<212> TYPE: PRT
<213> ORGANISM: Artificial Sequence
<220> FEATURE:
<223> OTHER INFORMATION: Gag 50

<400> SEQUENCE: 13

Val Gln Gly Met Ala Tyr Ala Ala Ala Met Arg Gly Gln Lys Tyr Ser
1               5                   10                  15

Thr Leu Val Lys
            20

<210> SEQ ID NO 14
<211> LENGTH: 20
<212> TYPE: PRT
<213> ORGANISM: Artificial Sequence
<220> FEATURE:
<223> OTHER INFORMATION: Gag 49

<400> SEQUENCE: 14

Arg Ala Cys Leu Asp Ala Ser Pro Ala Val Val Gln Gly Met Ala Tyr
1               5                   10                  15

Ala Ala Ala Met
```

```
<210> SEQ ID NO 15
<211> LENGTH: 20
<212> TYPE: PRT
<213> ORGANISM: Artificial Sequence
<220> FEATURE:
<223> OTHER INFORMATION: Gag 52

<400> SEQUENCE: 15

Gln Thr Tyr Gly Gly Gly Lys Gly Gly Gln Gly Ser Glu Gly Pro Val
1               5                   10                  15

Cys Phe Ser Cys
            20

<210> SEQ ID NO 16
<211> LENGTH: 18
<212> TYPE: PRT
<213> ORGANISM: Artificial Sequence
<220> FEATURE:
<223> OTHER INFORMATION: Env 79

<400> SEQUENCE: 16

Phe Ile Phe Ile Gly Val Gly Ala Leu Leu Leu Val Ile Val Leu Met
1               5                   10                  15

Ile Phe

<210> SEQ ID NO 17
<211> LENGTH: 18
<212> TYPE: PRT
<213> ORGANISM: Artificial Sequence
<220> FEATURE:
<223> OTHER INFORMATION: Env 85

<400> SEQUENCE: 17

Gly Asn Ala Ala Pro Ala Ala Glu Met Val Glu Leu Pro Arg Val Ser
1               5                   10                  15

Tyr Thr

<210> SEQ ID NO 18
<211> LENGTH: 18
<212> TYPE: PRT
<213> ORGANISM: Artificial Sequence
<220> FEATURE:
<223> OTHER INFORMATION: Env 15

<400> SEQUENCE: 18

Pro Val Gly Trp Gly Asn Thr Asp Pro Ile Arg Val Leu Thr Asn Gln
1               5                   10                  15

Thr Ile

<210> SEQ ID NO 19
<211> LENGTH: 18
<212> TYPE: PRT
<213> ORGANISM: Artificial Sequence
<220> FEATURE:
<223> OTHER INFORMATION: Env 13

<400> SEQUENCE: 19

Thr Gly Glu Ser Tyr Trp Ala Tyr Leu Pro Lys Pro Ser Ile Leu His
1               5                   10                  15

Pro Val
```

-continued

```
<210> SEQ ID NO 20
<211> LENGTH: 18
<212> TYPE: PRT
<213> ORGANISM: Artificial Sequence
<220> FEATURE:
<223> OTHER INFORMATION: Env 17

<400> SEQUENCE: 20

Thr Ile Tyr Leu Gly Gly Ser Pro Asp Phe His Gly Phe Arg Asn Met
1               5                   10                  15

Ser Gly

<210> SEQ ID NO 21
<211> LENGTH: 18
<212> TYPE: PRT
<213> ORGANISM: Artificial Sequence
<220> FEATURE:
<223> OTHER INFORMATION: Env 23

<400> SEQUENCE: 21

Gln Val Phe Leu Ser Asp Thr Pro Thr Val Asp Asn Asn Lys Pro Gly
1               5                   10                  15

Gly Lys

<210> SEQ ID NO 22
<211> LENGTH: 18
<212> TYPE: PRT
<213> ORGANISM: Artificial Sequence
<220> FEATURE:
<223> OTHER INFORMATION: Env 20

<400> SEQUENCE: 22

Lys Ser Asp Thr Leu Pro Ile Cys Phe Ser Leu Ser Phe Ser Thr Pro
1               5                   10                  15

Thr Gly

<210> SEQ ID NO 23
<211> LENGTH: 18
<212> TYPE: PRT
<213> ORGANISM: Artificial Sequence
<220> FEATURE:
<223> OTHER INFORMATION: Env 21

<400> SEQUENCE: 23

Phe Ser Leu Ser Phe Ser Thr Pro Thr Gly Cys Phe Gln Val Asp Lys
1               5                   10                  15

Gln Val

<210> SEQ ID NO 24
<211> LENGTH: 18
<212> TYPE: PRT
<213> ORGANISM: Artificial Sequence
<220> FEATURE:
<223> OTHER INFORMATION: Env 22

<400> SEQUENCE: 24

Thr Gly Cys Phe Gln Val Asp Lys Gln Val Phe Leu Ser Asp Thr Pro
1               5                   10                  15

Thr Val

<210> SEQ ID NO 25
<211> LENGTH: 18
<212> TYPE: PRT
<213> ORGANISM: Artificial Sequence
```

<220> FEATURE:
<223> OTHER INFORMATION: Env 24

<400> SEQUENCE: 25

Thr Val Asp Asn Asn Lys Pro Gly Gly Lys Gly Asp Lys Arg Arg Met
1               5                   10                  15

Trp Glu

<210> SEQ ID NO 26
<211> LENGTH: 18
<212> TYPE: PRT
<213> ORGANISM: Artificial Sequence
<220> FEATURE:
<223> OTHER INFORMATION: Env 19

<400> SEQUENCE: 26

Ser Gly Asn Val His Phe Glu Gly Lys Ser Asp Thr Leu Pro Ile Cys
1               5                   10                  15

Phe Ser

<210> SEQ ID NO 27
<211> LENGTH: 18
<212> TYPE: PRT
<213> ORGANISM: Artificial Sequence
<220> FEATURE:
<223> OTHER INFORMATION: Env 48

<400> SEQUENCE: 27

Ile Leu Leu Gly Leu Pro Gln Leu Ile Asp Ile Glu Lys Arg Gly Ser
1               5                   10                  15

Thr Phe

<210> SEQ ID NO 28
<211> LENGTH: 18
<212> TYPE: PRT
<213> ORGANISM: Artificial Sequence
<220> FEATURE:
<223> OTHER INFORMATION: Env 49

<400> SEQUENCE: 28

Ile Asp Ile Glu Lys Arg Gly Ser Thr Phe His Ile Ser Cys Ser Ser
1               5                   10                  15

Cys Arg

<210> SEQ ID NO 29
<211> LENGTH: 18
<212> TYPE: PRT
<213> ORGANISM: Artificial Sequence
<220> FEATURE:
<223> OTHER INFORMATION: Env 50

<400> SEQUENCE: 29

Thr Phe His Ile Ser Cys Ser Ser Cys Arg Leu Thr Asn Cys Leu Asp
1               5                   10                  15

Ser Ser

<210> SEQ ID NO 30
<211> LENGTH: 18
<212> TYPE: PRT
<213> ORGANISM: Artificial Sequence
<220> FEATURE:
<223> OTHER INFORMATION: Env 54

<400> SEQUENCE: 30

-continued

Val Leu Leu Pro Val Asp Ile Gly Asp Glu Pro Trp Phe Asp Asp Ser
1               5                   10                  15

Ala Ile

<210> SEQ ID NO 31
<211> LENGTH: 18
<212> TYPE: PRT
<213> ORGANISM: Artificial Sequence
<220> FEATURE:
<223> OTHER INFORMATION: Env 55

<400> SEQUENCE: 31

Asp Glu Pro Trp Phe Asp Ser Ala Ile Leu Thr Phe Arg Tyr Ala
1               5                   10                  15

Thr Asp

<210> SEQ ID NO 32
<211> LENGTH: 18
<212> TYPE: PRT
<213> ORGANISM: Artificial Sequence
<220> FEATURE:
<223> OTHER INFORMATION: Env 56

<400> SEQUENCE: 32

Ala Ile Leu Thr Phe Arg Tyr Ala Thr Asp Leu Ile Arg Ala Lys Arg
1               5                   10                  15

Phe Val

<210> SEQ ID NO 33
<211> LENGTH: 18
<212> TYPE: PRT
<213> ORGANISM: Artificial Sequence
<220> FEATURE:
<223> OTHER INFORMATION: Env 66

<400> SEQUENCE: 33

Glu Gly Val Val Leu Glu Leu Gly Gln Asp Glu Ala Asn Leu Lys Thr
1               5                   10                  15

Arg Met

<210> SEQ ID NO 34
<211> LENGTH: 18
<212> TYPE: PRT
<213> ORGANISM: Artificial Sequence
<220> FEATURE:
<223> OTHER INFORMATION: Env 68

<400> SEQUENCE: 34

Arg Met Ser Thr Arg Cys His Ala Asn Tyr Asp Phe Ile Cys Val Thr
1               5                   10                  15

Pro Leu

<210> SEQ ID NO 35
<211> LENGTH: 18
<212> TYPE: PRT
<213> ORGANISM: Artificial Sequence
<220> FEATURE:
<223> OTHER INFORMATION: Env 72

<400> SEQUENCE: 35

Leu Leu Gly Ile Trp Asn Asp Asn Glu Ile Ser Tyr Asn Ile Gln Glu
1               5                   10                  15

Leu Ala

```
<210> SEQ ID NO 36
<211> LENGTH: 18
<212> TYPE: PRT
<213> ORGANISM: Artificial Sequence
<220> FEATURE:
<223> OTHER INFORMATION: Env 73

<400> SEQUENCE: 36

Glu Ile Ser Tyr Asn Ile Gln Glu Leu Ala Asn Leu Ile Ser Asp Met
1               5                   10                  15

Ser Lys

<210> SEQ ID NO 37
<211> LENGTH: 20
<212> TYPE: PRT
<213> ORGANISM: Artificial Sequence
<220> FEATURE:
<223> OTHER INFORMATION: Gag 2

<400> SEQUENCE: 37

Leu Phe Val Ser Val Leu Gln Arg Leu Leu Ser Glu Arg Gly Leu His
1               5                   10                  15

Val Lys Glu Ser
            20

<210> SEQ ID NO 38
<211> LENGTH: 20
<212> TYPE: PRT
<213> ORGANISM: Artificial Sequence
<220> FEATURE:
<223> OTHER INFORMATION: Gag 4

<400> SEQUENCE: 38

Ser Ala Ile Glu Phe Tyr Gln Phe Leu Ile Lys Val Ser Pro Trp Phe
1               5                   10                  15

Pro Glu Glu Gly
            20

<210> SEQ ID NO 39
<211> LENGTH: 20
<212> TYPE: PRT
<213> ORGANISM: Artificial Sequence
<220> FEATURE:
<223> OTHER INFORMATION: Gag 5

<400> SEQUENCE: 39

Lys Val Ser Pro Trp Phe Pro Glu Glu Gly Gly Leu Asn Leu Gln Asp
1               5                   10                  15

Trp Lys Arg Val
            20

<210> SEQ ID NO 40
<211> LENGTH: 20
<212> TYPE: PRT
<213> ORGANISM: Artificial Sequence
<220> FEATURE:
<223> OTHER INFORMATION: Gag 6

<400> SEQUENCE: 40

Gly Leu Asn Leu Gln Asp Trp Lys Arg Val Gly Arg Glu Met Lys Arg
1               5                   10                  15

Tyr Ala Ala Glu
```

```
<210> SEQ ID NO 41
<211> LENGTH: 20
<212> TYPE: PRT
<213> ORGANISM: Artificial Sequence
<220> FEATURE:
<223> OTHER INFORMATION: Gag 7

<400> SEQUENCE: 41

Gly Arg Glu Met Lys Arg Tyr Ala Ala Glu His Gly Thr Asp Ser Ile
1               5                   10                  15

Pro Lys Gln Ala
            20

<210> SEQ ID NO 42
<211> LENGTH: 20
<212> TYPE: PRT
<213> ORGANISM: Artificial Sequence
<220> FEATURE:
<223> OTHER INFORMATION: Gag 8

<400> SEQUENCE: 42

His Gly Thr Asp Ser Ile Pro Lys Gln Ala Tyr Pro Ile Trp Leu Gln
1               5                   10                  15

Leu Arg Glu Ile
            20

<210> SEQ ID NO 43
<211> LENGTH: 20
<212> TYPE: PRT
<213> ORGANISM: Artificial Sequence
<220> FEATURE:
<223> OTHER INFORMATION: Gag 10

<400> SEQUENCE: 43

Leu Thr Glu Gln Ser Asp Leu Val Leu Leu Ser Ala Glu Ala Lys Ser
1               5                   10                  15

Val Thr Glu Glu
            20

<210> SEQ ID NO 44
<211> LENGTH: 20
<212> TYPE: PRT
<213> ORGANISM: Artificial Sequence
<220> FEATURE:
<223> OTHER INFORMATION: Gag 11

<400> SEQUENCE: 44

Ser Ala Glu Ala Lys Ser Val Thr Glu Glu Leu Glu Glu Gly Leu
1               5                   10                  15

Thr Gly Leu Leu
            20

<210> SEQ ID NO 45
<211> LENGTH: 20
<212> TYPE: PRT
<213> ORGANISM: Artificial Sequence
<220> FEATURE:
<223> OTHER INFORMATION: Gag 12

<400> SEQUENCE: 45

Glu Leu Glu Glu Gly Leu Thr Gly Leu Leu Ser Thr Ser Ser Gln Glu
1               5                   10                  15
```

Lys Thr Tyr Gly
        20

<210> SEQ ID NO 46
<211> LENGTH: 20
<212> TYPE: PRT
<213> ORGANISM: Artificial Sequence
<220> FEATURE:
<223> OTHER INFORMATION: Gag 13

<400> SEQUENCE: 46

Ser Thr Ser Ser Gln Glu Lys Thr Tyr Gly Thr Arg Gly Thr Ala Tyr
1               5                   10                  15

Ala Glu Ile Asp
        20

<210> SEQ ID NO 47
<211> LENGTH: 20
<212> TYPE: PRT
<213> ORGANISM: Artificial Sequence
<220> FEATURE:
<223> OTHER INFORMATION: Gag 14

<400> SEQUENCE: 47

Thr Arg Gly Thr Ala Tyr Ala Glu Ile Asp Thr Glu Val Asp Lys Leu
1               5                   10                  15

Ser Glu His Ile
        20

<210> SEQ ID NO 48
<211> LENGTH: 20
<212> TYPE: PRT
<213> ORGANISM: Artificial Sequence
<220> FEATURE:
<223> OTHER INFORMATION: Gag 15

<400> SEQUENCE: 48

Thr Glu Val Asp Lys Leu Ser Glu His Ile Tyr Asp Glu Pro Tyr Glu
1               5                   10                  15

Glu Lys Glu Lys
        20

<210> SEQ ID NO 49
<211> LENGTH: 20
<212> TYPE: PRT
<213> ORGANISM: Artificial Sequence
<220> FEATURE:
<223> OTHER INFORMATION: Gag 16

<400> SEQUENCE: 49

Tyr Asp Glu Pro Tyr Glu Glu Lys Glu Lys Ala Asp Lys Asn Glu Glu
1               5                   10                  15

Lys Asp His Val
        20

<210> SEQ ID NO 50
<211> LENGTH: 20
<212> TYPE: PRT
<213> ORGANISM: Artificial Sequence
<220> FEATURE:
<223> OTHER INFORMATION: Gag 17

<400> SEQUENCE: 50

Ala Asp Lys Asn Glu Glu Lys Asp His Val Arg Lys Val Lys Lys Val
1               5                   10                  15

Val Gln Arg Lys
            20

<210> SEQ ID NO 51
<211> LENGTH: 20
<212> TYPE: PRT
<213> ORGANISM: Artificial Sequence
<220> FEATURE:
<223> OTHER INFORMATION: Gag 18

<400> SEQUENCE: 51

Arg Lys Val Lys Lys Val Val Gln Arg Lys Glu Ile Ser Glu Gly Lys
1               5                   10                  15

Arg Lys Glu Lys
            20

<210> SEQ ID NO 52
<211> LENGTH: 20
<212> TYPE: PRT
<213> ORGANISM: Artificial Sequence
<220> FEATURE:
<223> OTHER INFORMATION: Gag 19

<400> SEQUENCE: 52

Glu Ile Ser Glu Gly Lys Arg Lys Glu Lys Asp Gln Lys Ala Phe Leu
1               5                   10                  15

Ala Thr Asp Trp
            20

<210> SEQ ID NO 53
<211> LENGTH: 20
<212> TYPE: PRT
<213> ORGANISM: Artificial Sequence
<220> FEATURE:
<223> OTHER INFORMATION: Gag 20

<400> SEQUENCE: 53

Asp Gln Lys Ala Phe Leu Ala Thr Asp Trp Asn Asp Asp Leu Ser
1               5                   10                  15

Pro Glu Asp Trp
            20

<210> SEQ ID NO 54
<211> LENGTH: 20
<212> TYPE: PRT
<213> ORGANISM: Artificial Sequence
<220> FEATURE:
<223> OTHER INFORMATION: Gag 21

<400> SEQUENCE: 54

Asn Asp Asp Asp Leu Ser Pro Glu Asp Trp Asp Leu Glu Glu Gln
1               5                   10                  15

Ala Ala His Tyr
            20

<210> SEQ ID NO 55
<211> LENGTH: 20
<212> TYPE: PRT
<213> ORGANISM: Artificial Sequence
<220> FEATURE:
<223> OTHER INFORMATION: Gag 22

<400> SEQUENCE: 55

Asp Asp Leu Glu Glu Gln Ala Ala His Tyr His Asp Asp Glu Leu

```
1               5                   10                  15
Ile Leu Pro Val
            20
```

<210> SEQ ID NO 56
<211> LENGTH: 20
<212> TYPE: PRT
<213> ORGANISM: Artificial Sequence
<220> FEATURE:
<223> OTHER INFORMATION: Gag 23

<400> SEQUENCE: 56

```
His Asp Asp Glu Leu Ile Leu Pro Val Lys Arg Lys Val Val Lys
1               5                   10                  15
Lys Lys Pro Gln
            20
```

<210> SEQ ID NO 57
<211> LENGTH: 20
<212> TYPE: PRT
<213> ORGANISM: Artificial Sequence
<220> FEATURE:
<223> OTHER INFORMATION: Gag 24

<400> SEQUENCE: 57

```
Lys Arg Lys Val Val Lys Lys Lys Pro Gln Ala Leu Arg Arg Lys Pro
1               5                   10                  15
Leu Pro Pro Val
            20
```

<210> SEQ ID NO 58
<211> LENGTH: 20
<212> TYPE: PRT
<213> ORGANISM: Artificial Sequence
<220> FEATURE:
<223> OTHER INFORMATION: Gag 28

<400> SEQUENCE: 58

```
Val Val Phe Met Gly Glu Ser Asp Asp Asp Thr Pro Val Trp Glu
1               5                   10                  15
Pro Leu Pro Leu
            20
```

<210> SEQ ID NO 59
<211> LENGTH: 20
<212> TYPE: PRT
<213> ORGANISM: Artificial Sequence
<220> FEATURE:
<223> OTHER INFORMATION: Gag 29

<400> SEQUENCE: 59

```
Asp Thr Pro Val Trp Glu Pro Leu Pro Leu Lys Thr Leu Lys Glu Leu
1               5                   10                  15
Gln Leu Ala Val
            20
```

<210> SEQ ID NO 60
<211> LENGTH: 20
<212> TYPE: PRT
<213> ORGANISM: Artificial Sequence
<220> FEATURE:
<223> OTHER INFORMATION: Gag 30

<400> SEQUENCE: 60

```
Lys Thr Leu Lys Glu Leu Gln Leu Ala Val Lys Thr Met Gly Pro Ser
1               5                   10                  15

Ala Pro Tyr Thr
            20

<210> SEQ ID NO 61
<211> LENGTH: 20
<212> TYPE: PRT
<213> ORGANISM: Artificial Sequence
<220> FEATURE:
<223> OTHER INFORMATION: Gag 31

<400> SEQUENCE: 61

Lys Thr Met Gly Pro Ser Ala Pro Tyr Thr Leu Gln Val Val Asp Met
1               5                   10                  15

Val Ala Ser Gln
            20

<210> SEQ ID NO 62
<211> LENGTH: 20
<212> TYPE: PRT
<213> ORGANISM: Artificial Sequence
<220> FEATURE:
<223> OTHER INFORMATION: Gag 32

<400> SEQUENCE: 62

Leu Gln Val Val Asp Met Val Ala Ser Gln Trp Leu Thr Pro Ser Asp
1               5                   10                  15

Trp His Gln Thr
            20

<210> SEQ ID NO 63
<211> LENGTH: 20
<212> TYPE: PRT
<213> ORGANISM: Artificial Sequence
<220> FEATURE:
<223> OTHER INFORMATION: Gag 34

<400> SEQUENCE: 63

Ala Arg Ala Thr Leu Ser Pro Gly Asp Tyr Val Leu Trp Arg Thr Glu
1               5                   10                  15

Tyr Glu Glu Lys
            20

<210> SEQ ID NO 64
<211> LENGTH: 20
<212> TYPE: PRT
<213> ORGANISM: Artificial Sequence
<220> FEATURE:
<223> OTHER INFORMATION: Gag 35

<400> SEQUENCE: 64

Val Leu Trp Arg Thr Glu Tyr Glu Glu Lys Ser Lys Glu Thr Val Gln
1               5                   10                  15

Lys Ala Ala Gly
            20

<210> SEQ ID NO 65
<211> LENGTH: 20
<212> TYPE: PRT
<213> ORGANISM: Artificial Sequence
<220> FEATURE:
<223> OTHER INFORMATION: Gag 36

<400> SEQUENCE: 65
```

Ser Lys Glu Thr Val Gln Lys Ala Ala Gly Lys Arg Lys Gly Lys Val
1               5                   10                  15

Ser Leu Asp Met
            20

<210> SEQ ID NO 66
<211> LENGTH: 20
<212> TYPE: PRT
<213> ORGANISM: Artificial Sequence
<220> FEATURE:
<223> OTHER INFORMATION: Gag 38

<400> SEQUENCE: 66

Leu Leu Gly Thr Gly Gln Phe Leu Ser Pro Ser Ser Gln Ile Lys Leu
1               5                   10                  15

Ser Lys Asp Val
            20

<210> SEQ ID NO 67
<211> LENGTH: 20
<212> TYPE: PRT
<213> ORGANISM: Artificial Sequence
<220> FEATURE:
<223> OTHER INFORMATION: Gag 39

<400> SEQUENCE: 67

Ser Ser Gln Ile Lys Leu Ser Lys Asp Val Leu Lys Asp Val Thr Thr
1               5                   10                  15

Asn Ala Val Leu
            20

<210> SEQ ID NO 68
<211> LENGTH: 20
<212> TYPE: PRT
<213> ORGANISM: Artificial Sequence
<220> FEATURE:
<223> OTHER INFORMATION: Gag 41

<400> SEQUENCE: 68

Ala Trp Arg Ala Ile Pro Pro Pro Gly Val Lys Lys Thr Val Leu Ala
1               5                   10                  15

Gly Leu Lys Gln
            20

<210> SEQ ID NO 69
<211> LENGTH: 20
<212> TYPE: PRT
<213> ORGANISM: Artificial Sequence
<220> FEATURE:
<223> OTHER INFORMATION: Gag 44

<400> SEQUENCE: 69

Ser Arg Leu Glu Glu Ala Val Tyr Arg Met Met Pro Arg Gly Glu Gly
1               5                   10                  15

Ser Asp Ile Leu
            20

<210> SEQ ID NO 70
<211> LENGTH: 20
<212> TYPE: PRT
<213> ORGANISM: Artificial Sequence
<220> FEATURE:
<223> OTHER INFORMATION: Gag 45

```
<400> SEQUENCE: 70

Met Pro Arg Gly Glu Gly Ser Asp Ile Leu Ile Lys Gln Leu Ala Trp
1               5                   10                  15

Glu Asn Ala Asn
            20

<210> SEQ ID NO 71
<211> LENGTH: 20
<212> TYPE: PRT
<213> ORGANISM: Artificial Sequence
<220> FEATURE:
<223> OTHER INFORMATION: Gag 46

<400> SEQUENCE: 71

Ile Lys Gln Leu Ala Trp Glu Asn Ala Asn Ser Leu Cys Gln Asp Leu
1               5                   10                  15

Ile Arg Pro Ile
            20

<210> SEQ ID NO 72
<211> LENGTH: 20
<212> TYPE: PRT
<213> ORGANISM: Artificial Sequence
<220> FEATURE:
<223> OTHER INFORMATION: Gag 47

<400> SEQUENCE: 72

Ser Leu Cys Gln Asp Leu Ile Arg Pro Ile Arg Lys Thr Gly Thr Ile
1               5                   10                  15

Gln Asp Tyr Ile
            20

<210> SEQ ID NO 73
<211> LENGTH: 20
<212> TYPE: PRT
<213> ORGANISM: Artificial Sequence
<220> FEATURE:
<223> OTHER INFORMATION: Gag 48

<400> SEQUENCE: 73

Arg Lys Thr Gly Thr Ile Gln Asp Tyr Ile Arg Ala Cys Leu Asp Ala
1               5                   10                  15

Ser Pro Ala Val
            20

<210> SEQ ID NO 74
<211> LENGTH: 20
<212> TYPE: PRT
<213> ORGANISM: Artificial Sequence
<220> FEATURE:
<223> OTHER INFORMATION: Gag 53

<400> SEQUENCE: 74

Gly Ser Glu Gly Pro Val Cys Phe Ser Cys Gly Lys Thr Gly His Ile
1               5                   10                  15

Lys Lys Asp Cys
            20

<210> SEQ ID NO 75
<211> LENGTH: 20
<212> TYPE: PRT
<213> ORGANISM: Artificial Sequence
<220> FEATURE:
<223> OTHER INFORMATION: Gag 54
```

```
<400> SEQUENCE: 75

Gly Lys Thr Gly His Ile Lys Lys Asp Cys Lys Glu Glu Lys Gly Ser
1               5                   10                  15

Lys Arg Ala Pro
            20

<210> SEQ ID NO 76
<211> LENGTH: 20
<212> TYPE: PRT
<213> ORGANISM: Artificial Sequence
<220> FEATURE:
<223> OTHER INFORMATION: Gag 55

<400> SEQUENCE: 76

Lys Glu Glu Lys Gly Ser Lys Arg Ala Pro Ser Gly Leu Cys Pro Arg
1               5                   10                  15

Cys Lys Lys Gly
            20

<210> SEQ ID NO 77
<211> LENGTH: 20
<212> TYPE: PRT
<213> ORGANISM: Artificial Sequence
<220> FEATURE:
<223> OTHER INFORMATION: Gag 56

<400> SEQUENCE: 77

Ser Gly Leu Cys Pro Arg Cys Lys Lys Gly Tyr His Trp Lys Ser Glu
1               5                   10                  15

Cys Lys Ser Lys
            20

<210> SEQ ID NO 78
<211> LENGTH: 20
<212> TYPE: PRT
<213> ORGANISM: Artificial Sequence
<220> FEATURE:
<223> OTHER INFORMATION: Gag 55

<400> SEQUENCE: 78

Tyr His Trp Lys Ser Glu Cys Lys Ser Lys Phe Asp Lys Asp Gly Asn
1               5                   10                  15

Pro Leu Pro Pro
            20

<210> SEQ ID NO 79
<211> LENGTH: 20
<212> TYPE: PRT
<213> ORGANISM: Artificial Sequence
<220> FEATURE:
<223> OTHER INFORMATION: Gag 58

<400> SEQUENCE: 79

Asp Lys Asp Gly Asn Pro Leu Pro Pro Leu Glu Thr Asn Thr Glu Asn
1               5                   10                  15

Ser Lys Asn Leu
            20

<210> SEQ ID NO 80
<211> LENGTH: 18
<212> TYPE: PRT
<213> ORGANISM: Artificial Sequence
<220> FEATURE:
```

<223> OTHER INFORMATION: Env 1

<400> SEQUENCE: 80

Met Pro Asn His Gln Ser Gly Ser Pro Thr Gly Ser Ser Asp Leu Leu
1               5                   10                  15

Leu Ser

<210> SEQ ID NO 81
<211> LENGTH: 18
<212> TYPE: PRT
<213> ORGANISM: Artificial Sequence
<220> FEATURE:
<223> OTHER INFORMATION: Env 2

<400> SEQUENCE: 81

Pro Thr Gly Ser Ser Asp Leu Leu Leu Ser Gly Lys Lys Gln Arg Pro
1               5                   10                  15

His Leu

<210> SEQ ID NO 82
<211> LENGTH: 18
<212> TYPE: PRT
<213> ORGANISM: Artificial Sequence
<220> FEATURE:
<223> OTHER INFORMATION: Env 3

<400> SEQUENCE: 82

Leu Ser Gly Lys Lys Gln Arg Pro His Leu Ala Leu Arg Arg Lys Arg
1               5                   10                  15

Arg Arg

<210> SEQ ID NO 83
<211> LENGTH: 18
<212> TYPE: PRT
<213> ORGANISM: Artificial Sequence
<220> FEATURE:
<223> OTHER INFORMATION: Env 4

<400> SEQUENCE: 83

His Leu Ala Leu Arg Arg Lys Arg Arg Arg Glu Met Arg Lys Ile Asn
1               5                   10                  15

Arg Lys

<210> SEQ ID NO 84
<211> LENGTH: 18
<212> TYPE: PRT
<213> ORGANISM: Artificial Sequence
<220> FEATURE:
<223> OTHER INFORMATION: Env 5

<400> SEQUENCE: 84

Arg Arg Glu Met Arg Lys Ile Asn Arg Lys Val Arg Arg Met Asn Leu
1               5                   10                  15

Ala Pro

<210> SEQ ID NO 85
<211> LENGTH: 18
<212> TYPE: PRT
<213> ORGANISM: Artificial Sequence
<220> FEATURE:
<223> OTHER INFORMATION: Env 6

<400> SEQUENCE: 85

Arg Lys Val Arg Arg Met Asn Leu Ala Pro Ile Lys Glu Lys Thr Ala
1               5                   10                  15

Trp Gln

<210> SEQ ID NO 86
<211> LENGTH: 18
<212> TYPE: PRT
<213> ORGANISM: Artificial Sequence
<220> FEATURE:
<223> OTHER INFORMATION: Env 7

<400> SEQUENCE: 86

Ala Pro Ile Lys Glu Lys Thr Ala Trp Gln His Leu Gln Ala Leu Ile
1               5                   10                  15

Phe Glu

<210> SEQ ID NO 87
<211> LENGTH: 18
<212> TYPE: PRT
<213> ORGANISM: Artificial Sequence
<220> FEATURE:
<223> OTHER INFORMATION: Env 8

<400> SEQUENCE: 87

Trp Gln His Leu Gln Ala Leu Ile Phe Glu Ala Glu Glu Val Leu Lys
1               5                   10                  15

Thr Ser

<210> SEQ ID NO 88
<211> LENGTH: 18
<212> TYPE: PRT
<213> ORGANISM: Artificial Sequence
<220> FEATURE:
<223> OTHER INFORMATION: Env 9

<400> SEQUENCE: 88

Phe Glu Ala Glu Glu Val Leu Lys Thr Ser Gln Thr Pro Gln Thr Ser
1               5                   10                  15

Leu Thr

<210> SEQ ID NO 89
<211> LENGTH: 18
<212> TYPE: PRT
<213> ORGANISM: Artificial Sequence
<220> FEATURE:
<223> OTHER INFORMATION: Env 10

<400> SEQUENCE: 89

Thr Ser Gln Thr Pro Gln Thr Ser Leu Thr Leu Phe Leu Thr Leu Leu
1               5                   10                  15

Ser Val

<210> SEQ ID NO 90
<211> LENGTH: 18
<212> TYPE: PRT
<213> ORGANISM: Artificial Sequence
<220> FEATURE:
<223> OTHER INFORMATION: Env 11

<400> SEQUENCE: 90

Leu Thr Leu Phe Leu Thr Leu Leu Ser Val Leu Gly Pro Pro Pro Val
1               5                   10                  15

Thr Gly

<210> SEQ ID NO 91
<211> LENGTH: 18
<212> TYPE: PRT
<213> ORGANISM: Artificial Sequence
<220> FEATURE:
<223> OTHER INFORMATION: Env 12

<400> SEQUENCE: 91

Ser Val Leu Gly Pro Pro Val Thr Gly Glu Ser Tyr Trp Ala Tyr
1               5                   10                  15

Leu Pro

<210> SEQ ID NO 92
<211> LENGTH: 18
<212> TYPE: PRT
<213> ORGANISM: Artificial Sequence
<220> FEATURE:
<223> OTHER INFORMATION: Env 14

<400> SEQUENCE: 92

Leu Pro Lys Pro Ser Ile Leu His Pro Val Gly Trp Gly Asn Thr Asp
1               5                   10                  15

Pro Ile

<210> SEQ ID NO 93
<211> LENGTH: 18
<212> TYPE: PRT
<213> ORGANISM: Artificial Sequence
<220> FEATURE:
<223> OTHER INFORMATION: Env 16

<400> SEQUENCE: 93

Pro Ile Arg Val Leu Thr Asn Gln Thr Ile Tyr Leu Gly Gly Ser Pro
1               5                   10                  15

Asp Phe

<210> SEQ ID NO 94
<211> LENGTH: 18
<212> TYPE: PRT
<213> ORGANISM: Artificial Sequence
<220> FEATURE:
<223> OTHER INFORMATION: Env 18

<400> SEQUENCE: 94

Asp Phe His Gly Phe Arg Asn Met Ser Gly Asn Val His Phe Glu Gly
1               5                   10                  15

Lys Ser

<210> SEQ ID NO 95
<211> LENGTH: 18
<212> TYPE: PRT
<213> ORGANISM: Artificial Sequence
<220> FEATURE:
<223> OTHER INFORMATION: Env 25

<400> SEQUENCE: 95

Gly Lys Gly Asp Lys Arg Arg Met Trp Glu Leu Trp Leu Thr Thr Leu
1               5                   10                  15

Gly Asn

<210> SEQ ID NO 96
<211> LENGTH: 18

```
<212> TYPE: PRT
<213> ORGANISM: Artificial Sequence
<220> FEATURE:
<223> OTHER INFORMATION: Env 26

<400> SEQUENCE: 96

Trp Glu Leu Trp Leu Thr Thr Leu Gly Asn Ser Gly Ala Asn Thr Lys
1               5                   10                  15

Leu Val

<210> SEQ ID NO 97
<211> LENGTH: 18
<212> TYPE: PRT
<213> ORGANISM: Artificial Sequence
<220> FEATURE:
<223> OTHER INFORMATION: Env 27

<400> SEQUENCE: 97

Gly Asn Ser Gly Ala Asn Thr Lys Leu Val Pro Ile Lys Lys Lys Leu
1               5                   10                  15

Pro Pro

<210> SEQ ID NO 98
<211> LENGTH: 18
<212> TYPE: PRT
<213> ORGANISM: Artificial Sequence
<220> FEATURE:
<223> OTHER INFORMATION: Env 28

<400> SEQUENCE: 98

Leu Val Pro Ile Lys Lys Lys Leu Pro Pro Lys Tyr Pro His Cys Gln
1               5                   10                  15

Ile Ala

<210> SEQ ID NO 99
<211> LENGTH: 18
<212> TYPE: PRT
<213> ORGANISM: Artificial Sequence
<220> FEATURE:
<223> OTHER INFORMATION: Env 29

<400> SEQUENCE: 99

Pro Pro Lys Tyr Pro His Cys Gln Ile Ala Phe Lys Lys Asp Ala Phe
1               5                   10                  15

Trp Glu

<210> SEQ ID NO 100
<211> LENGTH: 18
<212> TYPE: PRT
<213> ORGANISM: Artificial Sequence
<220> FEATURE:
<223> OTHER INFORMATION: Env 29 Amino Acid Sequence

<400> SEQUENCE: 100

Pro Pro Lys Tyr Pro His Cys Gln Ile Ala Phe Lys Lys Asp Ala Phe
1               5                   10                  15

Trp Glu

<210> SEQ ID NO 101
<211> LENGTH: 18
<212> TYPE: PRT
<213> ORGANISM: Artificial Sequence
<220> FEATURE:
<223> OTHER INFORMATION: Env 30
```

```
<400> SEQUENCE: 101

Ile Ala Phe Lys Lys Asp Ala Phe Trp Glu Gly Asp Glu Ser Ala Pro
1               5                   10                  15

Pro Arg

<210> SEQ ID NO 102
<211> LENGTH: 18
<212> TYPE: PRT
<213> ORGANISM: Artificial Sequence
<220> FEATURE:
<223> OTHER INFORMATION: Env 31

<400> SEQUENCE: 102

Trp Glu Gly Asp Glu Ser Ala Pro Pro Arg Trp Leu Pro Cys Ala Phe
1               5                   10                  15

Pro Asp

<210> SEQ ID NO 103
<211> LENGTH: 18
<212> TYPE: PRT
<213> ORGANISM: Artificial Sequence
<220> FEATURE:
<223> OTHER INFORMATION: Env 32

<400> SEQUENCE: 103

Pro Arg Trp Leu Pro Cys Ala Phe Pro Asp Gln Gly Val Ser Phe Ser
1               5                   10                  15

Pro Lys

<210> SEQ ID NO 104
<211> LENGTH: 18
<212> TYPE: PRT
<213> ORGANISM: Artificial Sequence
<220> FEATURE:
<223> OTHER INFORMATION: Env 33

<400> SEQUENCE: 104

Pro Asp Gln Gly Val Ser Phe Ser Pro Lys Gly Thr Leu Gly Leu Leu
1               5                   10                  15

Trp Asp

<210> SEQ ID NO 105
<211> LENGTH: 18
<212> TYPE: PRT
<213> ORGANISM: Artificial Sequence
<220> FEATURE:
<223> OTHER INFORMATION: Env 34

<400> SEQUENCE: 105

Pro Lys Gly Thr Leu Gly Leu Leu Trp Asp Phe Ser Leu Pro Ser Pro
1               5                   10                  15

Ser Val

<210> SEQ ID NO 106
<211> LENGTH: 18
<212> TYPE: PRT
<213> ORGANISM: Artificial Sequence
<220> FEATURE:
<223> OTHER INFORMATION: Env 35

<400> SEQUENCE: 106

Trp Asp Phe Ser Leu Pro Ser Pro Ser Val Asp Gln Ser Asp Gln Ile
```

-continued

```
                1               5                   10                  15
Lys Ser

<210> SEQ ID NO 107
<211> LENGTH: 18
<212> TYPE: PRT
<213> ORGANISM: Artificial Sequence
<220> FEATURE:
<223> OTHER INFORMATION: Env 36

<400> SEQUENCE: 107

Ser Val Asp Gln Ser Asp Gln Ile Lys Ser Lys Lys Asp Leu Phe Gly
1               5                   10                  15

Asn Tyr

<210> SEQ ID NO 108
<211> LENGTH: 18
<212> TYPE: PRT
<213> ORGANISM: Artificial Sequence
<220> FEATURE:
<223> OTHER INFORMATION: Env 37

<400> SEQUENCE: 108

Lys Ser Lys Lys Asp Leu Phe Gly Asn Tyr Thr Pro Pro Val Asn Lys
1               5                   10                  15

Glu Val

<210> SEQ ID NO 109
<211> LENGTH: 18
<212> TYPE: PRT
<213> ORGANISM: Artificial Sequence
<220> FEATURE:
<223> OTHER INFORMATION: Env 38

<400> SEQUENCE: 109

Asn Tyr Thr Pro Pro Val Asn Lys Glu Val His Arg Trp Tyr Glu Ala
1               5                   10                  15

Gly Trp

<210> SEQ ID NO 110
<211> LENGTH: 18
<212> TYPE: PRT
<213> ORGANISM: Artificial Sequence
<220> FEATURE:
<223> OTHER INFORMATION: Env 39

<400> SEQUENCE: 110

Glu Val His Arg Trp Tyr Glu Ala Gly Trp Val Glu Pro Thr Trp Phe
1               5                   10                  15

Trp Glu

<210> SEQ ID NO 111
<211> LENGTH: 18
<212> TYPE: PRT
<213> ORGANISM: Artificial Sequence
<220> FEATURE:
<223> OTHER INFORMATION: Env 39 Amino Acid Sequence

<400> SEQUENCE: 111

Glu Val His Arg Trp Tyr Glu Ala Gly Trp Val Glu Pro Thr Trp Phe
1               5                   10                  15

Trp Glu
```

<210> SEQ ID NO 112
<211> LENGTH: 18
<212> TYPE: PRT
<213> ORGANISM: Artificial Sequence
<220> FEATURE:
<223> OTHER INFORMATION: Env 40

<400> SEQUENCE: 112

Gly Trp Val Glu Pro Thr Trp Phe Trp Glu Asn Ser Pro Lys Asp Pro
1               5                   10                  15

Asn Asp

<210> SEQ ID NO 113
<211> LENGTH: 18
<212> TYPE: PRT
<213> ORGANISM: Artificial Sequence
<220> FEATURE:
<223> OTHER INFORMATION: Env 41

<400> SEQUENCE: 113

Trp Glu Asn Ser Pro Lys Asp Pro Asn Asp Arg Asp Phe Thr Ala Leu
1               5                   10                  15

Val Pro

<210> SEQ ID NO 114
<211> LENGTH: 18
<212> TYPE: PRT
<213> ORGANISM: Artificial Sequence
<220> FEATURE:
<223> OTHER INFORMATION: Env 42

<400> SEQUENCE: 114

Asn Asp Arg Asp Phe Thr Ala Leu Val Pro His Thr Glu Leu Phe Arg
1               5                   10                  15

Leu Val

<210> SEQ ID NO 115
<211> LENGTH: 18
<212> TYPE: PRT
<213> ORGANISM: Artificial Sequence
<220> FEATURE:
<223> OTHER INFORMATION: Env 43

<400> SEQUENCE: 115

Val Pro His Thr Glu Leu Phe Arg Leu Val Ala Ala Ser Arg Tyr Leu
1               5                   10                  15

Ile Leu

<210> SEQ ID NO 116
<211> LENGTH: 18
<212> TYPE: PRT
<213> ORGANISM: Artificial Sequence
<220> FEATURE:
<223> OTHER INFORMATION: Env 44

<400> SEQUENCE: 116

Leu Val Ala Ala Ser Arg Tyr Leu Ile Leu Lys Arg Pro Gly Phe Gln
1               5                   10                  15

Glu His

<210> SEQ ID NO 117
<211> LENGTH: 18
<212> TYPE: PRT

<213> ORGANISM: Artificial Sequence
<220> FEATURE:
<223> OTHER INFORMATION: Env 45

<400> SEQUENCE: 117

Ile Leu Lys Arg Pro Gly Phe Gln Glu His Asp Met Ile Pro Thr Ser
1               5                   10                  15

Ala Cys

<210> SEQ ID NO 118
<211> LENGTH: 18
<212> TYPE: PRT
<213> ORGANISM: Artificial Sequence
<220> FEATURE:
<223> OTHER INFORMATION: Env 46

<400> SEQUENCE: 118

Glu His Asp Met Ile Pro Thr Ser Ala Cys Ala Thr Tyr Pro Tyr Ala
1               5                   10                  15

Ile Leu

<210> SEQ ID NO 119
<211> LENGTH: 18
<212> TYPE: PRT
<213> ORGANISM: Artificial Sequence
<220> FEATURE:
<223> OTHER INFORMATION: Env 47

<400> SEQUENCE: 119

Ala Cys Ala Thr Tyr Pro Tyr Ala Ile Leu Leu Gly Leu Pro Gln Leu
1               5                   10                  15

Ile Asp

<210> SEQ ID NO 120
<211> LENGTH: 18
<212> TYPE: PRT
<213> ORGANISM: Artificial Sequence
<220> FEATURE:
<223> OTHER INFORMATION: Env 51

<400> SEQUENCE: 120

Cys Arg Leu Thr Asn Cys Leu Asp Ser Ser Ala Tyr Asp Tyr Ala Ala
1               5                   10                  15

Ile Ile

<210> SEQ ID NO 121
<211> LENGTH: 18
<212> TYPE: PRT
<213> ORGANISM: Artificial Sequence
<220> FEATURE:
<223> OTHER INFORMATION: Env 52

<400> SEQUENCE: 121

Ser Ser Ala Tyr Asp Tyr Ala Ala Ile Ile Val Lys Arg Pro Pro Tyr
1               5                   10                  15

Val Leu

<210> SEQ ID NO 122
<211> LENGTH: 18
<212> TYPE: PRT
<213> ORGANISM: Artificial Sequence
<220> FEATURE:
<223> OTHER INFORMATION: Env 52 Amino Acid Sequence

```
<400> SEQUENCE: 122

Ser Ser Ala Tyr Asp Tyr Ala Ala Ile Ile Val Lys Arg Pro Pro Tyr
1               5                   10                  15

Val Leu

<210> SEQ ID NO 123
<211> LENGTH: 18
<212> TYPE: PRT
<213> ORGANISM: Artificial Sequence
<220> FEATURE:
<223> OTHER INFORMATION: Env 53

<400> SEQUENCE: 123

Ile Ile Val Lys Arg Pro Pro Tyr Val Leu Leu Pro Val Asp Ile Gly
1               5                   10                  15

Asp Glu

<210> SEQ ID NO 124
<211> LENGTH: 18
<212> TYPE: PRT
<213> ORGANISM: Artificial Sequence
<220> FEATURE:
<223> OTHER INFORMATION: Env 57

<400> SEQUENCE: 124

Thr Asp Leu Ile Arg Ala Lys Arg Phe Val Ala Ala Ile Ile Leu Gly
1               5                   10                  15

Ile Ser

<210> SEQ ID NO 125
<211> LENGTH: 18
<212> TYPE: PRT
<213> ORGANISM: Artificial Sequence
<220> FEATURE:
<223> OTHER INFORMATION: Env 58

<400> SEQUENCE: 125

Phe Val Ala Ala Ile Ile Leu Gly Ile Ser Ala Leu Ile Ala Ile Ile
1               5                   10                  15

Thr Ser

<210> SEQ ID NO 126
<211> LENGTH: 18
<212> TYPE: PRT
<213> ORGANISM: Artificial Sequence
<220> FEATURE:
<223> OTHER INFORMATION: Env 59

<400> SEQUENCE: 126

Ile Ser Ala Leu Ile Ala Ile Ile Thr Ser Phe Ala Val Ala Thr Thr
1               5                   10                  15

Ala Leu

<210> SEQ ID NO 127
<211> LENGTH: 18
<212> TYPE: PRT
<213> ORGANISM: Artificial Sequence
<220> FEATURE:
<223> OTHER INFORMATION: Env 60

<400> SEQUENCE: 127

Thr Ser Phe Ala Val Ala Thr Thr Ala Leu Val Lys Glu Met Gln Thr
1               5                   10                  15
```

Ala Thr

<210> SEQ ID NO 128
<211> LENGTH: 18
<212> TYPE: PRT
<213> ORGANISM: Artificial Sequence
<220> FEATURE:
<223> OTHER INFORMATION: Env 61

<400> SEQUENCE: 128

Ala Leu Val Lys Glu Met Gln Thr Ala Thr Phe Val Asn Asn Leu His
1               5                   10                  15

Arg Asn

<210> SEQ ID NO 129
<211> LENGTH: 18
<212> TYPE: PRT
<213> ORGANISM: Artificial Sequence
<220> FEATURE:
<223> OTHER INFORMATION: Env 62

<400> SEQUENCE: 129

Ala Thr Phe Val Asn Asn Leu His Arg Asn Val Thr Leu Ala Leu Ser
1               5                   10                  15

Glu Gln

<210> SEQ ID NO 130
<211> LENGTH: 18
<212> TYPE: PRT
<213> ORGANISM: Artificial Sequence
<220> FEATURE:
<223> OTHER INFORMATION: Env 63

<400> SEQUENCE: 130

Arg Asn Val Thr Leu Ala Leu Ser Glu Gln Arg Ile Ile Asp Leu Lys
1               5                   10                  15

Leu Glu

<210> SEQ ID NO 131
<211> LENGTH: 18
<212> TYPE: PRT
<213> ORGANISM: Artificial Sequence
<220> FEATURE:
<223> OTHER INFORMATION: Env 64

<400> SEQUENCE: 131

Glu Gln Arg Ile Ile Asp Leu Lys Leu Glu Ala Arg Leu Asn Ala Leu
1               5                   10                  15

Glu Gly

<210> SEQ ID NO 132
<211> LENGTH: 18
<212> TYPE: PRT
<213> ORGANISM: Artificial Sequence
<220> FEATURE:
<223> OTHER INFORMATION: Env 65

<400> SEQUENCE: 132

Leu Glu Ala Arg Leu Asn Ala Leu Glu Gly Val Val Leu Glu Leu Gly
1               5                   10                  15

Gln Asp

```
<210> SEQ ID NO 133
<211> LENGTH: 18
<212> TYPE: PRT
<213> ORGANISM: Artificial Sequence
<220> FEATURE:
<223> OTHER INFORMATION: Env 67

<400> SEQUENCE: 133

Gln Asp Glu Ala Asn Leu Lys Thr Arg Met Ser Thr Arg Cys His Ala
1               5                   10                  15

Asn Tyr

<210> SEQ ID NO 134
<211> LENGTH: 18
<212> TYPE: PRT
<213> ORGANISM: Artificial Sequence
<220> FEATURE:
<223> OTHER INFORMATION: Env 69

<400> SEQUENCE: 134

Asn Tyr Asp Phe Ile Cys Val Thr Pro Leu Pro Tyr Asn Ala Ser Glu
1               5                   10                  15

Ser Trp

<210> SEQ ID NO 135
<211> LENGTH: 18
<212> TYPE: PRT
<213> ORGANISM: Artificial Sequence
<220> FEATURE:
<223> OTHER INFORMATION: Env 70

<400> SEQUENCE: 135

Pro Leu Pro Tyr Asn Ala Ser Glu Ser Trp Glu Arg Thr Lys Ala His
1               5                   10                  15

Leu Leu

<210> SEQ ID NO 136
<211> LENGTH: 18
<212> TYPE: PRT
<213> ORGANISM: Artificial Sequence
<220> FEATURE:
<223> OTHER INFORMATION: Env 71

<400> SEQUENCE: 136

Ser Trp Glu Arg Thr Lys Ala His Leu Leu Gly Ile Trp Asn Asp Asn
1               5                   10                  15

Glu Ile

<210> SEQ ID NO 137
<211> LENGTH: 18
<212> TYPE: PRT
<213> ORGANISM: Artificial Sequence
<220> FEATURE:
<223> OTHER INFORMATION: Env 74

<400> SEQUENCE: 137

Leu Ala Asn Leu Ile Ser Asp Met Ser Lys Gln His Ile Asp Thr Val
1               5                   10                  15

Asp Leu

<210> SEQ ID NO 138
<211> LENGTH: 18
<212> TYPE: PRT
<213> ORGANISM: Artificial Sequence
```

<220> FEATURE:
<223> OTHER INFORMATION: Env 75

<400> SEQUENCE: 138

Ser Lys Gln His Ile Asp Thr Val Asp Leu Ser Gly Leu Ala Gln Ser
1               5                   10                  15

Phe Ala

<210> SEQ ID NO 139
<211> LENGTH: 18
<212> TYPE: PRT
<213> ORGANISM: Artificial Sequence
<220> FEATURE:
<223> OTHER INFORMATION: Env 76

<400> SEQUENCE: 139

Asp Leu Ser Gly Leu Ala Gln Ser Phe Ala Asn Gly Val Lys Ala Leu
1               5                   10                  15

Asn Pro

<210> SEQ ID NO 140
<211> LENGTH: 18
<212> TYPE: PRT
<213> ORGANISM: Artificial Sequence
<220> FEATURE:
<223> OTHER INFORMATION: Env 77

<400> SEQUENCE: 140

Phe Ala Asn Gly Val Lys Ala Leu Asn Pro Leu Asp Trp Thr Gln Tyr
1               5                   10                  15

Phe Ile

<210> SEQ ID NO 141
<211> LENGTH: 18
<212> TYPE: PRT
<213> ORGANISM: Artificial Sequence
<220> FEATURE:
<223> OTHER INFORMATION: Env 78

<400> SEQUENCE: 141

Asn Pro Leu Asp Trp Thr Gln Tyr Phe Ile Phe Ile Gly Val Gly Ala
1               5                   10                  15

Leu Leu

<210> SEQ ID NO 142
<211> LENGTH: 18
<212> TYPE: PRT
<213> ORGANISM: Artificial Sequence
<220> FEATURE:
<223> OTHER INFORMATION: Env 80

<400> SEQUENCE: 142

Leu Leu Leu Val Ile Val Leu Met Ile Phe Pro Ile Val Phe Gln Cys
1               5                   10                  15

Leu Ala

<210> SEQ ID NO 143
<211> LENGTH: 18
<212> TYPE: PRT
<213> ORGANISM: Artificial Sequence
<220> FEATURE:
<223> OTHER INFORMATION: Env 81

<400> SEQUENCE: 143

```
Ile Phe Pro Ile Val Phe Gln Cys Leu Ala Lys Ser Leu Asp Gln Val
1               5                   10                  15

Gln Ser

<210> SEQ ID NO 144
<211> LENGTH: 18
<212> TYPE: PRT
<213> ORGANISM: Artificial Sequence
<220> FEATURE:
<223> OTHER INFORMATION: Env 82

<400> SEQUENCE: 144

Leu Ala Lys Ser Leu Asp Gln Val Gln Ser Asp Leu Asn Val Leu Leu
1               5                   10                  15

Leu Lys

<210> SEQ ID NO 145
<211> LENGTH: 18
<212> TYPE: PRT
<213> ORGANISM: Artificial Sequence
<220> FEATURE:
<223> OTHER INFORMATION: Env 83

<400> SEQUENCE: 145

Gln Ser Asp Leu Asn Val Leu Leu Leu Lys Lys Lys Gly Gly Asn
1               5                   10                  15

Ala Ala

<210> SEQ ID NO 146
<211> LENGTH: 18
<212> TYPE: PRT
<213> ORGANISM: Artificial Sequence
<220> FEATURE:
<223> OTHER INFORMATION: Env 84

<400> SEQUENCE: 146

Leu Lys Lys Lys Lys Gly Gly Asn Ala Ala Pro Ala Ala Glu Met Val
1               5                   10                  15

Glu Leu

<210> SEQ ID NO 147
<211> LENGTH: 454
<212> TYPE: PRT
<213> ORGANISM: Artificial Sequence
<220> FEATURE:
<223> OTHER INFORMATION: HBRV Su Amino Acid Sequence

<400> SEQUENCE: 147

Met Pro Asn His Gln Ser Gly Ser Pro Thr Gly Ser Ser Asp Leu Leu
1               5                   10                  15

Leu Ser Gly Lys Lys Gln Arg Pro His Leu Ala Leu Arg Lys Arg
            20                  25                  30

Arg Ser Glu Met Arg Lys Ile Asn Arg Lys Val Arg Met Asn Leu
            35                  40                  45

Ala Pro Ile Lys Glu Lys Thr Ala Trp Gln His Leu Gln Ala Leu Ile
        50                  55                  60

Phe Glu Ala Glu Glu Val Leu Lys Thr Ser Gln Thr Pro Gln Thr Ser
65                  70                  75                  80

Leu Thr Leu Phe Leu Ala Leu Leu Ser Val Leu Gly Pro Pro Val
                85                  90                  95
```

```
Thr Gly Glu Ser Tyr Trp Ala Tyr Leu Pro Lys Pro Ile Leu His
            100                 105                 110

Pro Val Gly Trp Gly Asn Thr Asp Pro Ile Arg Val Leu Thr Asn Gln
        115                 120                 125

Thr Ile Tyr Leu Gly Gly Ser Pro Asp Phe His Gly Phe Arg Asn Met
    130                 135                 140

Ser Gly Asn Val His Phe Glu Gly Lys Ser Asp Thr Leu Pro Ile Cys
145                 150                 155                 160

Phe Ser Phe Ser Phe Ser Thr Pro Thr Gly Cys Phe Gln Val Asp Lys
                165                 170                 175

Gln Val Phe Leu Ser Asp Thr Pro Ala Val Asp Asn Asn Lys Pro Gly
            180                 185                 190

Gly Lys Gly Asp Lys Arg Arg Met Trp Glu Leu Trp Leu Thr Thr Leu
        195                 200                 205

Gly Asn Ser Gly Ala Asn Thr Lys Leu Val Pro Ile Lys Lys Lys Leu
    210                 215                 220

Pro Pro Lys Tyr Pro His Cys Gln Ile Ala Phe Lys Lys Asp Ala Phe
225                 230                 235                 240

Trp Glu Gly Asp Glu Ser Ala Pro Pro Arg Trp Leu Pro Cys Ala Phe
                245                 250                 255

Pro Asp Gln Gly Val Ser Phe Ser Pro Lys Gly Thr Leu Gly Leu Leu
            260                 265                 270

Trp Asp Phe Ser Leu Pro Ser Pro Ser Val Asp Gln Ser Asp Gln Ile
        275                 280                 285

Arg Ser Lys Lys Asp Leu Phe Gly Asn Tyr Thr Pro Pro Val Asn Lys
    290                 295                 300

Glu Val His Arg Trp Tyr Glu Ala Gly Trp Val Glu Arg Thr Trp Phe
305                 310                 315                 320

Trp Glu Asn Ser Pro Lys Asp Pro Asn Asp Arg Asp Phe Thr Ala Leu
                325                 330                 335

Val Pro His Thr Glu Leu Phe Arg Leu Val Ala Ala Ser Arg Tyr Leu
            340                 345                 350

Ile Leu Lys Arg Pro Gly Phe Gln Glu His Asp Met Ile Pro Thr Ser
        355                 360                 365

Ala Cys Ala Thr Tyr Pro Tyr Ala Ile Leu Leu Gly Leu Pro Gln Leu
    370                 375                 380

Ile Asp Ile Glu Lys Arg Gly Ser Thr Phe His Ile Ser Cys Ser Ser
385                 390                 395                 400

Cys Arg Leu Thr Asn Cys Leu Asp Ser Ser Ala Tyr Asp Tyr Ala Ala
                405                 410                 415

Ile Ile Val Lys Arg Pro Pro Tyr Val Leu Leu Pro Val Asp Ile Gly
            420                 425                 430

Asp Glu Pro Trp Phe Asp Asp Ser Ala Ile Leu Thr Phe Arg Tyr Ala
        435                 440                 445

Thr Asp Leu Ile Arg Ala
    450

<210> SEQ ID NO 148
<211> LENGTH: 1362
<212> TYPE: DNA
<213> ORGANISM: Artificial Sequence
<220> FEATURE:
<223> OTHER INFORMATION: HBRV Vector Coding Sequence

<400> SEQUENCE: 148
```

```
atgccgaatc accaatctgg gtccccgacc ggttcatccg accttttact gagcggaaag    60
aagcaacgcc cacacctggc actgcggaga aaacgccgca gcgagatgag aaagatcaac   120
aggaaagtcc ggaggatgaa tctagccccc atcaaagaga agacggcttg caacatctg    180
caggcgttaa tcttcgaagc ggaggaggtt cttaaaacct cacaaactcc ccaaacctct   240
ttgactttat ttcttgcttt gttgtctgtc ctcggccccc cgcctgtgac cggggaaagt   300
tattgggctt acctacctaa accacctatt ctccatcccg tgggatgggg aaatacagac   360
cccattagag ttctgaccaa tcaaaccata tatttgggtg ggtcacctga ctttcacggg   420
tttagaaaca tgtctggcaa tgtacatttt gaggggaagt ctgatacgct ccccatttgc   480
ttttccttct ccttttctac ccccacaggc tgctttcaag tagataagca agtatttctt   540
tctgatacac ccgcggttga taataataaa cctgggggaa agggtgataa aaggcgtatg   600
tgggaacttt ggttgactac tttggggaac tcaggggcca atacaaaact ggtccctata   660
aaaaagaagt tgcccccccaa atatcctcac tgccagatcg cctttaagaa ggacgccttc   720
tgggagggag acgagtctgc tcctccacgg tggttgcctt gcgccttccc tgaccagggg   780
gtgagttttt ctccaaaagg gacccttggg ttactttggg atttctccct tccctcgcct   840
agtgtagatc agtcagatca gattagaagc aaaaaggatc tatttggaaa ttatactccc   900
cctgtcaata aagaggttca tcgatggtat gaagcaggat gggtagaacg tacatggttc   960
tgggaaaatt ctcctaagga tcccaatgat agagatttta ctgctctagt tccccataca  1020
gaattgtttc gcttagttgc agcctcaaga tatcttattc tcaaaaggcc aggatttcaa  1080
gaacatgaca tgattcctac atctgcctgt gctacttacc cttatgccat attattagga  1140
ttacctcagc taatagatat agagaaaaga ggatctactt ttcatatttc ctgttcttct  1200
tgtagattga ctaattgttt agattcttct gcctacgact atgcagcgat catagtcaag  1260
aggccgccat acgtgctgct acctgtagat attggtgatg aaccatggtt tgatgattct  1320
gccattctaa cctttaggta tgccacagat ttaattcgag cc                     1362
```

<210> SEQ ID NO 149
<211> LENGTH: 34
<212> TYPE: DNA
<213> ORGANISM: Artificial Sequence
<220> FEATURE:
<223> OTHER INFORMATION: Primer SuFW

<400> SEQUENCE: 149
gttggctagc atgccgaatc accaatctgg gtcc                              34

<210> SEQ ID NO 150
<211> LENGTH: 33
<212> TYPE: DNA
<213> ORGANISM: Artificial Sequence
<220> FEATURE:
<223> OTHER INFORMATION: Primer SuRV

<400> SEQUENCE: 150
tcgaggtacc ggctcgaatt aaatctgtgg cat                               33

<210> SEQ ID NO 151
<211> LENGTH: 29
<212> TYPE: DNA
<213> ORGANISM: Artificial Sequence
<220> FEATURE:
<223> OTHER INFORMATION: Primer TapFW

<400> SEQUENCE: 151

```
atgcggtacc ctggtgccgc gcggcagcg                              29

<210> SEQ ID NO 152
<211> LENGTH: 33
<212> TYPE: DNA
<213> ORGANISM: Artificial Sequence
<220> FEATURE:
<223> OTHER INFORMATION: Primer TapRV

<400> SEQUENCE: 152
ctccggatcc ttaatggtga tggtgatgat gcc                         33

<210> SEQ ID NO 153
<211> LENGTH: 38
<212> TYPE: DNA
<213> ORGANISM: Artificial Sequence
<220> FEATURE:
<223> OTHER INFORMATION: Primer PuriFW

<400> SEQUENCE: 153
gatcgatatc ccgggatggc caccgagtac aagcccac                    38

<210> SEQ ID NO 154
<211> LENGTH: 32
<212> TYPE: DNA
<213> ORGANISM: Artificial Sequence
<220> FEATURE:
<223> OTHER INFORMATION: Primer PuriRV

<400> SEQUENCE: 154
gatcttcgaa tcaggcaccg ggcttgcggg tc                          32
```

BETARETROVIRUS EPITOPES AND RELATED METHODS OF USE

CROSS REFERENCE TO RELATED APPLICATION

This application claims priority to and the benefit of U.S. provisional patent application 62/758,823, entitled "Betaretrovirus Epitopes and Related Methods of Use", filed on Nov. 12, 2018, the disclosure of which is incorporated herein by reference in its entirety.

FIELD OF INVENTION

The present invention relates to betaretrovirus proteins and related methods of use. More specifically, the present invention relates to methods of detecting infection or risk of infection by a betaretrovirus.

BACKGROUND OF THE INVENTION

Primary biliary cholangitis (PBC), previously known as primary biliary cirrhosis, is often characterized as an autoimmune disease of the liver. It may result from a slow, progressive destruction of the small bile ducts of the liver, causing bile and other toxins to build up in the liver, a condition called cholestasis. Further slow damage to the liver tissue can lead to scarring, fibrosis, and eventually cirrhosis.

The prevalence of PBC in North America is ~1/3,000 and the disease is 10 times more common in women. A third of subjects may develop progressive disease accounting for 5% of subjects requiring liver transplantation in Canada. PBC is often characterized histologically by a non-suppurative cholangitis with granulomatous destruction of 30 to 80 μm interlobular bile ducts. The progressive ductopenia may lead to bile accumulation in the liver resulting in fibrosis and cirrhosis.

More recently, a link between PBC and viral infections has been suggested. Human betaretrovirus (HBRV) infections have been previously characterized in subjects with primary biliary cholangitis (PBC). Human betaretrovirus (HBRV) is genetically similar to the mouse mammary tumor virus (MMTV). Recent reports have documented HBRV proviral integrations in bile ducts in the majority of PBC subjects studied. Moreover, sustained biochemical responses have been reported in subjects on long term combination anti-retroviral therapy.

Breast cancer is a frequent cancer diagnosis among females and a leading cause of cancer deaths worldwide. Several viruses have been linked with human breast cancer in some way. Breast cancer patients have been reported to harbour betaretrovirus nucleic acid sequences and/or proteins in the literature, with one example being human mammary tumor virus, which is the same virus as the human betaretrovirus.

There is a need in the art for a detection method for human betaretroviral infections. Confirmation of viral infections are typically limited because conventional polymerase chain reaction (PCR) and serological diagnostics are only capable of detecting HBRV infection in a minority of PBC subjects. This may be due to low viral levels, which limits detection by various methods, including PCR. PCR methods are also susceptible to contamination. PCR methods may additionally require confirmation of infection with viral integrations. HBRV may also evade immune responses with presentation of immunosuppressive domains in the gp52 Surface protein that triggers IL-10 production to inhibit immune system cells. For this reason and others, few mice and humans make neutralizing antibodies, making detection of betaretrovirus difficult.

SUMMARY OF THE INVENTION

According to an embodiment of the present invention, there is provided a method for determination of risk and/or presence of a human betaretrovirus infection in a subject. Such methods may, for example, provide and/or assist with diagnosis and/or treatment of cancer (for example, breast cancer or lymphoma) and/or liver disease (for example, primary biliary cholangitis and autoimmune hepatitis). The method comprises incubating a biological sample from the subject with one or more betaretrovirus-specific epitopes, the biological sample comprising immune effector-producing cells, the betaretrovirus-specific epitopes having a sequence of at least 7 contiguous amino acids according to any one of SEQ ID Nos. 1-146, and measuring the production of immune effectors by the immune effector-producing cells wherein production of the immune effectors by the immune effector-producing cells determines risk and/or presence of betaretrovirus infection in the subject. The betaretrovirus specific epitopes may have a sequence according to SEQ ID Nos: 1-36. The biological sample may be obtained from the subject. The subject may be a human or murine (mouse) subject. The subject may be diagnosed with one or more of cancer or liver disease or suspected of having cancer or a liver disease. Immune effector production may be above a pre-determined threshold to indicate infection or risk of infection.

In one or more embodiments of the method, the cancer may be breast cancer, or hematopoetic malignancy and the liver disease may be primary biliary cholangitis, autoimmune hepatitis, alcoholic associated liver disease, or cryptogenic cirrhosis. The hematopoetic malignancy may be chronic lymphocytic leukemia (CLL), non-Hodgkins lymphoma, or plasma cell myeloma. The subject may be diagnosed with an autoimmune disorder or neurodegenerative disease or suspected of having an autoimmune disorder or neurodegenerative disease. The autoimmune disorder may be Crohn's disease or Systemic Lupus Erythematosus and the neurodegenerative disease may be Parkinson's disease or Alzheimer's disease. The biological sample may comprise whole blood or purified leukocytes obtained from the subject. The leukocytes may be intrahepatic leukocytes. The immune effector-producing cells may be CD8+ T-cells. The immune effector may be any one of interferon-gamma, TNF-alpha, or a combination thereof.

In one or more embodiments of the method, production of the immune effectors above a pre-determined threshold may be indicative of an infection, previous history of an infection, or risk of an infection of betaretrovirus. The production of the immune effectors by the step of incubating the biological sample may comprise immune effector-producing cells with one or more betaretrovirus-specific epitopes may be greater than a control step of incubating the biological sample comprising immune effector-producing cells with no stimulus. The control step may comprise incubating the biological sample comprising immune effector-producing cells with one or more non-betaretrovirus-specific epitopes or other suitable control. Said greater production of immune effectors may be indicative of an infection or risk of an infection of betaretrovirus. The production of the immune effector may be measured at 10 micrograms/ml or greater. In a preferred embodiment, the immune effector is interferon-gamma.

A method for determination of risk and/or presence of a betaretrovirus infection in a subject is described herein. The method may comprise incubating a biological sample comprising a plurality of lymphocytes derived from the subject in an assay with about 15 or more, for example 20, betaretrovirus-specific epitopes, each epitope may comprise about 15 or more contiguous amino acids according to any one of SEQ ID Nos. 1-146, such as 1-36, for a time period sufficient for the lymphocytes to produce interferon-gamma, TNF-alpha and optionally one or more additional cytokines, and measuring the production of interferon-gamma, TNF-alpha and optionally one or more additional cytokines by the lymphocytes cells. An increased production of interferon-gamma, TNF-alpha, or both, as compared to a control-treated biological sample identifies the subject at increased risk for the presence of betaretrovirus infection or confirms the presence of betaretrovirus infection. The subject determined at risk for betaretrovirus infection or that exhibits the presence of betaretrovirus may be treated.

Any embodiment of the methods discussed herein may further comprise treatment of the subject following the indication of viral infection. Treatment may comprise anti-cancer and/or cancer prevention therapy, anti-viral therapy or a combination thereof. Treatment may comprise combination antiretroviral therapy (cART). cART may comprise administration of Raltegravir and Emtricitabine/tenofovir or a combination thereof optionally with any other antiretroviral therapy known in the art. cART may comprise inhibitors of retroviral enzymes, including reverse transcriptase, protease, integrase, or a combination thereof, cART may comprise a broad spectrum antiviral that inhibits HBRV, including a GSK-3beta inhibitor or a cyclophilin inhibitor.

Any embodiment of the methods discussed herein may comprise betaretrovirus-specific epitopes that comprise at least 8, 9, 10, 11, 12, 13, 14, 15, 16, 17, 18, 19 or 20 contiguous amino acids according to any one of SEQ ID Nos. 1-146, such as 1-36. Any embodiment of the methods described herein may have 36, 35, 34, 33, 32, 32, 30, 29, 28, 27, 26, 25, 24, 23, 22, 21, 20, 19, 18, 17, 16, 15, 14, 1, 12, 10, 9, 8, 7, 6, 5, 4, 3, 2 or 1 betaretrovirus-specific epitopes employed in the method. Any embodiment of the methods discussed herein may comprise a step of testing a sample of the subject for viral nucleic acids via reverse transcriptase PCR (RT-PCR) or serologic reactivity to retroviruses and retroviral sequences within the liver to further confirm betaretrovirus infection.

According to an embodiment of the present invention, there is provided an isolated immunogenic betaretrovirus peptide comprising at least 7, 8, 9, 10, 11, 12, 13, 14, 15, 16, 17, 18, 19, or 20 contiguous amino acids as defined by any one of SEQ ID Nos: 1-146 or a plurality of said peptides. A composition is disclosed comprising the isolated immunogenic betaretrovirus he isolated immunogenic betaretrovirus peptide and a carrier, diluent or excipient. A composition is disclosed comprising one or more isolated immunogenic peptides described herein, wherein said peptide is covalently attached or physically associated with a dish, bead, well, support, macromolecule, carrier or the like, optionally via a linker or spacer. Said peptide may be a tetrameric peptide, comprising monomeric sequences according to any one of SEQ ID Nos: 1-146, such as 1-36.

Kits for the determination of an infection or risk of an infection by human betaretrovirus in a subject are also provided. A kit may comprise a composition as detailed herein and one or more of a biological sample collection vessel, an anticoagulation agent, one or more buffers, a needle for drawing a biological sample, and any instructions, products, reagents, compositions, culture dishes or plates, glassware, plasticware, medical devices, the like, or any combination thereof, to carry out the method of any one of claims 1-25. In some embodiments, the kit comprises one or more human betaretrovirus-specific epitopes each of at least 7 amino acids according to SEQ ID Nos: 1-146, such as 1-36.

According to an embodiment of the invention there is provided a method for measuring cell-mediated immune response activity in a subject, said method comprising contacting a sample source of lymphocytes from the subject with one or more agents which potentiate proinflammatory immune responses and measuring the presence or elevation in the level of an immune effector from immune cells wherein the presence or level of the immune effector is indicative of the level of cell-mediated responsiveness of the subject. The one or more agents may comprise a sequence of at least 7 contiguous amino acids according to any one of SEQ ID Nos: 1-146, such as 1-36.

Isolated peptides associated with human betaretrovirus are also provided. The isolated peptide may comprise at least 7 consecutive amino acids according to any one of SEQ ID Nos: 1-146, such as 1-36. The peptide may be combined with a pharmaceutically acceptable adjuvant, diluent or carrier. The peptide may be used for immunization of a subject. A combination for immunization of a subject, the combination comprising an isolated peptide, and an adjuvant, pharmaceutical excipient or combinations thereof.

The invention also provides a peptide sequence as described above and herein throughout which is greater than 7 amino acids in length, for example, but not limited to 8, 9, 10, 11, 12, 13, 14, 15, 16, 17, 18, 19, 20, 21, 22, 23, 24, 25, 26, 27, 28, 29, 30, 40, 50, 60, 70, 80, 90, 100 or more amino acids. Further the length may be defined by a range of any two values noted above or any two values therein between. For example, but not to be considered limiting in any manner, the invention contemplates amino acids having a size range of between 11 and 25, or between 41 and 95. Ranges outside those specifically described are also contemplated.

A method for measuring cell-mediated immune response activity in a subject is also disclosed. The method may comprise contacting a sample source of lymphocytes from the subject with one or more agents which potentiate the adaptive and innate immune systems and measuring the presence or elevation in the level of one or more immune effectors from immune cells wherein the presence or level of the immune effector is indicative of the level of cell-mediated responsiveness of the subject wherein the one or more agents comprise a sequence of at least 7 contiguous amino acids according to any one of SEQ ID Nos. 1-146, such as 1-36.

A method for determination of a human betaretrovirus infection, previous history or risk of a human betaretrovirus infection in a subject is disclosed. The method may comprise obtaining a biological sample from the subject, the biological sample comprising one or more human antibodies, incubating the biological sample with one or more betaretrovirus-specific epitopes, the virus specific epitopes having a sequence of at least 7 contiguous amino acids according to any one of SEQ ID Nos. 1-146, such as 1-36, and measuring the binding of the one or more human antibodies with the one or more betaretrovirus-specific epitopes, wherein binding is indicative of an infection by the betaretrovirus. The binding may be considered indicative when above a predetermined threshold. The betaretrovirus-specific epitopes may be immobilized epitopes and measuring the binding of the one or more human antibodies comprises washing with at least one anti-human antibody-indicator hybrid. The method may further comprise incubating the biological sample with anti-betaretrovirus antibodies.

In another embodiment, there is provided herein a method for diagnosis of cancer and/or a liver disease, or risk thereof, in a subject, the method comprising: incubating a biological sample from the subject, the biological sample comprising immune effector-producing cells, with one or more betaretrovirus-specific epitopes, the betaretrovirus-specific epitopes comprising at least 7 contiguous amino acids according to any one of SEQ ID Nos. 1-36; and measuring the production of one or more immune effectors by the immune effector-producing cells; wherein production of the one or more immune effectors by the immune effector-producing cells above that of a healthy control or comparator is indicative of the subject having or being at risk of developing cancer and/or a liver disease. In another embodiment, the cancer may be breast cancer or lymphoma. In another embodiment, the liver disease may be primary biliary cholangitis (PBC), or an autoimmune disease linked to PBC.

In another embodiment, there is provided herein a method of treating and/or preventing cancer, said method comprising: diagnosing cancer or a cancer risk in the subject, the diagnosis comprising incubating a biological sample from the subject, the biological sample comprising immune effector-producing cells, with one or more betaretrovirus-specific epitopes, the betaretrovirus-specific epitopes comprising at least 7 contiguous amino acids according to any one of SEQ ID Nos. 1-36; and measuring the production of one or more immune effectors by the immune effector-producing cells, wherein production of the one or more immune effectors by the immune effector-producing cells above that of a healthy control or comparator is indicative of the subject having cancer or increased cancer risk; and treating the subject with one or more anti-cancer therapeutics such as any suitable cancer chemotherapy known to the skilled person, treating the subject with one or more anti-viral treatments for betaretrovirus infection, or a combination thereof.

In another embodiment, there is provided herein a method of treating a liver disease, said method comprising: diagnosing liver disease in the subject, the diagnosis comprising incubating a biological sample from the subject, the biological sample comprising immune effector-producing cells, with one or more betaretrovirus-specific epitopes, the betaretrovirus-specific epitopes comprising at least 7 contiguous amino acids according to any one of SEQ ID Nos. 1-36; and measuring the production of one or more immune effectors by the immune effector-producing cells, wherein production of the one or more immune effectors by the immune effector-producing cells above that of a healthy control or comparator is indicative of the subject having liver disease; and treating the subject with one or more liver disease therapies known to the skilled person, treating the subject with one or more anti-viral treatments for betaretrovirus infection, or a combination thereof.

In another embodiment of any of the above methods, the cancer may be breast cancer or lymphoma. In another embodiment, the liver disease may be primary biliary cholangitis (PBC), or an autoimmune disease linked to PBC.

In another embodiment, there is provided herein a method for diagnosing presence of a betaretrovirus infection, diagnosing cancer, diagnosing a liver disease, or any combination thereof, said method comprising: determining a level of anti-HBRV gp52 Surface (Su) antibodies in a subject; wherein an elevated level of anti-HBRV Su antibodies in the subject as compared to a healthy control or comparator is indicative of presence of a betaretrovirus infection, diagnosing cancer or cancer risk, diagnosing a liver disease, or any combination thereof. In an embodiment, the step of determining may comprise exposing an antibody-containing biological sample from the subject to an HBRV Su epitope to determine a presence or level of anti-HBRV Su antibodies in the sample. In another embodiment, the step of determining may comprise exposing an antibody-containing biological sample from the subject to a peptide comprising an HBRV Su epitope, the peptide being immobilized to a solid support, membrane, or other support. In another embodiment, the step of determining may comprise performing an ELISA-type assay in which an antibody-containing biological sample from the subject is exposed to a solid support coated with a peptide comprising an HBRV Su epitope such that anti-HBRV Su antibodies, if present, bind the peptide, and are subsequently detected and/or quantified.

In another embodiment, there is provided herein a method for treating a betaretrovirus infection, cancer, a liver disease, or any combination thereof, comprising diagnosing the subject as being in need to treatment using an of the method or methods as described herein, and then treating the subject with an anti-viral, anti-cancer, or anti-liver disease therapy, or any combination thereof.

In another embodiment of the above methods, the biological sample may comprise a serum sample from the subject.

In another embodiment, there is provided herein an expression vector encoding HBRV Su coding sequence. In another embodiment, the expression vector may comprise a TAP tag at the 3' terminus of the HBRV Su, at least one (for example, 4) copies of M-PMV cytoplasmic transport element (CTE) downstream, or both. In another embodiment, there is provided herein a cell transfected with an expression vector as described herein. In another embodiment, there is provided herein an isolated peptide comprising HBRV Su. In another embodiment, there is provided herein a peptide comprising HBRV Su, the peptide being covalently attached or physically associated with a dish, bead, well, support, macromolecule, carrier or the like, optionally via a tetramer, linker or spacer.

In another embodiment, the expression vector may encode HBRV Su, or a portion thereof. In another embodiment, the expression vector may encode SEQ ID NO: 147, or a portion thereof, or a sequence having at least 80% sequence identity therewith:

(SEQ ID NO: 147)
MPNHQSGSPTGSSDLLLSGKKQRPHLALRRKRRSEMRKINRKVRRMNL

APIKEKTAWQHLQALIFEAEEVLKTSQTPQTSLTLFLALLSVLGPPPV

TGESYWAYLPKPPILHPVGWGNTDPIRVLTNQTIYLGGSPDFHGFRNM

SGNVHFEGKSDTLPICFSFSFSTPTGCFQVDKQVFLSDTPAVDNNKPG

GKGDKRRMWELWLTTLGNSGANTKLVPIKKKLPPKYPHCQIAFKKDAF

WEGDESAPPRWLPCAFPDQGVSFSPKGTLGLLWDFSLPSPSVDQSDQI

RSKKDLFGNYTPPVNKEVHRWYEAGWVERTWFWENSPKDPNDRDFTAL

-continued

VPHTELFRLVAASRYLILKRPGFQEHDMIPTSACATYPYAILLGLPQL

IDIEKRGSTFHISCSSCRLTNCLDSSAYDYAAIIVKRPPYVLLPVDIG

DEPWFDDSAILTFRYATDLIRA.

In another embodiment, the expression vector may comprise the following coding sequence (SEQ ID NO: 148) or a sequence having at least about 80% sequence identity therewith, or another coding sequence encoding the same amino acid sequence or an amino acid sequence having at least about 80% sequence identity therewith:

(SEQ ID NO: 148)
<u>atgccgaatcaccaatctgggtccc</u>cgaccggttcatccgacctttta ctgagcggaaagaagcaacgcccacacctggcactgcggagaaaacgc cgcagcgagatgagaaagatcaacaggaaagtccggaggatgaatcta gcccccatcaaagagaagacggcttggcaacatctgcaggcgttaatc ttcgaagcggaggaggttcttaaaacctcacaaactccccaaacctat ttgactttatttcttgctttgttgtctgtcctcggccccccgcctgtg accggggaaagttatgggcttacctacctaaaccacctattctccat cccgtgggatggggaaatacagaccccattagagttctgaccaatcaa accatatatttgggtgggtcacctgactttcacgggtttagaaacatg tctggcaatgtacattttgaggggaagtctgatacgctccccatttgc ttttccttctccttttctaccccacaggctgctttcaagtagataag caagtatttctttctgatacaccgcggttgataataataaacctggg ggaaagggtgataaaaggcgtatgtgggaactttggttgactactttg gggaactcaggggccaatacaaaactggtccctataaaaagaagttg cccccaaatatcctcactgccagatcgcctttaagaaggacgccttc tgggagggagacgagtctgctcctccacggtggttgccttgcgccttc cctgaccaggggtgagttttctccaaaagggacccttgggttactt tgggatttctcccttccctcgcctagtgtagatcagtcagatcagatt agaagcaaaaggatctatttggaaattatactcccctgtcaataaa gaggttcatcgatggtatgaagcaggatgggtagaacgtacatggttc tgggaaaattctcctaaggatcccaatgatagagattttactgctcta gttccccatacagaattgtttcgcttagttgcagcctcaagatatctt attctcaaaaggccaggatttcaagaacatgacatgattcctacatct gcctgtgctacttacccttatgccatattattaggattacctcagcta atagatatagagaaagaggatctacttttcatatttcctgttcttct tgtagattgactaattgtttagattcttctgcctacgactatgcagcg atcatagtcaagaggccgccatacgtgctgctacctgtagatattggt gatgaaccatggtttgatgattctgccattctaacctttaggt<u>atgcc</u>

<u>acagatttaattcgagcc</u>.

In another embodiment, there is provided herein a kit for diagnosing presence of a betaretrovirus infection, diagnosing cancer, diagnosing a liver disease, or any combination thereof, in a subject. In an embodiment, the kit may comprise an expression vector encoding HBRV Su coding sequence as described herein, a cell transfected with the expressing vector, an isolated peptide comprising HBRV Su, or any combination thereof. In an embodiment, the peptide comprising HBRV Su may be covalently attached or physically associated with a dish, bead, well, support, macromolecule, carrier or the like, optionally via a tetramer, linker or spacer. In another embodiment, the kit may further comprise any one or more of a biological sample collection vessel, an anticoagulation agent, one or more buffers, a needle for drawing a biological sample, and any instructions, products, reagents, compositions, culture dishes or plates, glassware, plasticware, medical devices, the like, or any combination thereof, to carry out a method as described herein. In some embodiments, the kit may further comprise one or more human betaretrovirus-specific epitopes each of at least 7 amino acids according to SEQ ID Nos: 1-146, such as SEQ ID Nos: 1-36.

In another embodiment, there is provided herein a method for preparing a peptide comprising HBRV Su, said method comprising: transfecting a cell with an expression vector as described herein expressing HBRV Su, culturing the transfected cell, and collecting the peptide comprising HBRV Su produced by the cell. In an embodiment, the collecting may comprise precipitating the peptide comprising HBRV Su with TCA. In another embodiment, the culturing may comprise culturing the cell in medium supplemented with 10% FBS for a first period, followed by replacing the media with serum-free media for a second period, and collecting the peptide comprising HBRV Su from the serum-free media and/or cells therein. In an embodiment, the collection may comprise column chromatography purification to collect the peptide comprising HBRV Su.

In another embodiment, there is provided herein a method for preparing HBRV Su, said method comprising: transfecting a cell with an expression vector encoding tagged HBRV Su; expanding the transfected cells in medium supplemented with FBS; replacing the medium with serum-free medium when cells reach about 95% confluence; incubating the cells, and collecting the supernatant following incubation; and collecting and purifying the HBRV Su by His-Tag column purification.

BRIEF DESCRIPTION OF THE DRAWINGS

These and other features of the invention will become more apparent from the following description in which reference is made to the appended drawings wherein:

FIG. 4C is a schematic depicting test samples for an embodiment of the immunological-based diagnostic assay.

FIG. 4D is a schematic depicting suitable methods for detecting cytokine production.

Figure 1A:
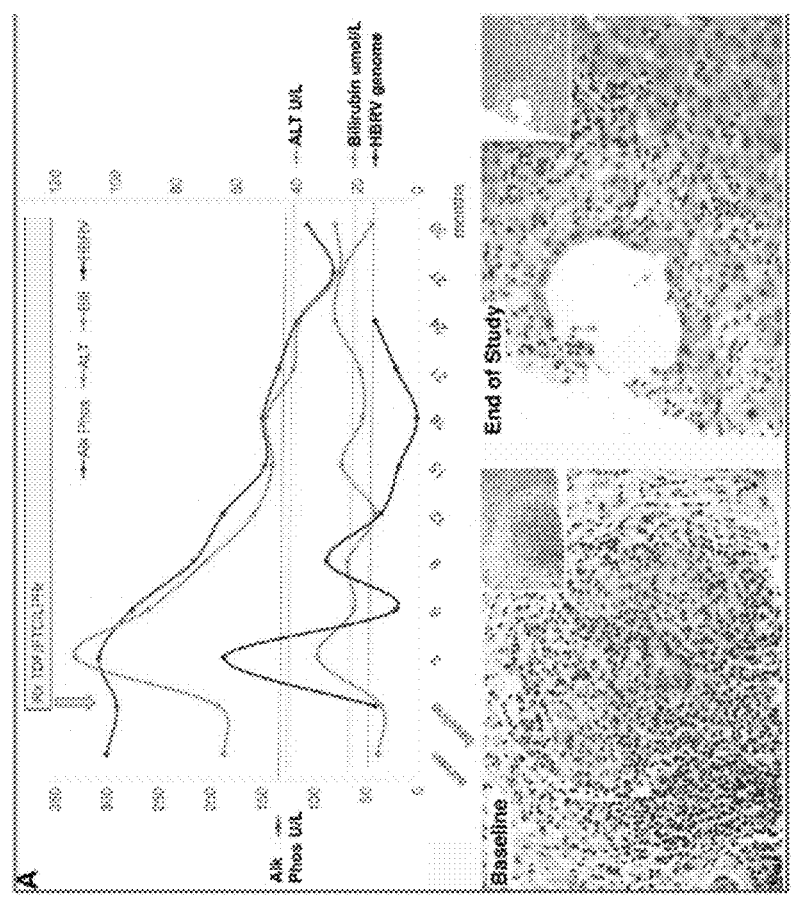
FIGS. 1A and 1B depict normalization of hepatic biochemistry and improvement in histology with Kaletra and Emtricitabine/tenofovir and off label Raltegravir and Emtricitabine/tenofovir.

Other applications of the disclosed methods include the analysis or monitoring of treatment steps for betaretrovirus infection and/or underlying/associated diseases and conditions.

Disclosed herein is a method for determination of a betaretrovirus infection or risk of a betaretrovirus infection in a subject, the method comprising incubating a biological sample from a subject, the biological sample comprising immune effector-producing cells, with one or more betaretrovirus-specific epitopes, the betaretrovirus-specific epitopes having a sequence of at least 7 contiguous amino acids according to any one of SEQ ID Nos. 1-36, and measuring the production of immune effectors by the immune effector-producing cells, wherein production of the immune effectors by the immune effector-producing cells is indicative of an infection by the betaretrovirus. In some embodiments, the betaretrovirus-specific epitopes have a sequence corresponding with any sequence encoded in the viral genome, for example SEQ ID Nos: 1-146.

Also disclosed herein is a method for measuring cell-mediated immune response activity in a subject, said method comprising contacting a sample source of lymphocytes from the subject with one or more agents which potentiate the adaptive and innate immune systems and measuring the presence, the level or change in the level of an immune effector from immune cells wherein the presence, the level, or change in level of the immune effector is indicative of the cell-mediated responsiveness of the subject, wherein the one or more agents comprise a sequence of at least 7 contiguous amino acids defined by any Gag or Env sequence, for example any one of SEQ ID Nos 1-146.

According to one embodiment, the assay comprises contacting the incubation composition or a portion thereof, such as a cell-depleted portion thereof, with an antibody or a fragment thereof specific for the immune effector to be detected for a time and under conditions sufficient for an antibody-effector complex to form, and then detecting said complex. As described above, cells comprised in the incubation composition may be removed by centrifugation prior to detection. When using blood as sample, cells can be separated from the incubation composition after incubation and thus production and release of immune effectors prior to detection, thereby basically providing a plasma sample.

Reference to a "subject" includes a human or non-human species including primates, livestock animals (sheep, cows, pigs, horses, donkey, goats), laboratory test animals (mice, rats, rabbits, guinea pigs, hamsters), companion animals (dogs, cats), avian species (poultry birds, aviary birds), reptiles and amphibians. The method disclosed herein has applicability in research, human medicine as well as in livestock, veterinary and wild-life applications. In a preferred embodiment, the subject is a human subject. In a further embodiment, which is not meant to be limiting in any manner, the subject is a mouse or rat.

Subjects as described in the embodiments may be diagnosed with cancer, liver disease or another disease/condition. The cancer may be breast cancer, or hematopoietic malignancy, such as chronic lymphocytic leukemia (CLL), non-Hodgkin's lymphoma, or plasma cell myeloma. The liver disease may be primary biliary cholangitis, autoimmune hepatitis, alcoholic liver disease, or cryptogenic cirrhosis. Subjects may also be diagnosed with Autoimmune/inflammatory diseases such as Crohn's disease and Systemic Lupus Erythematosus, and Neuropsychiatric/Neurodegenerative disorders such as Chronic fatigue syndrome, Alzheimer's disease, and Parkinson's disease. Parkinson's disease may be considered a disease with an autoimmune and/or a mitochondrial aspect. Patients with PBC may present symptoms of Parkinson's disease, such as lesions in the basal ganglia. These lesions may be found by brain scans.

The biological sample or "sample" comprises immune-effector producer cells capable of producing immune effectors following stimulation with an appropriate epitope. "Immune-effector producing cells" include but are not limited to immune cells, such as lymphocytes including natural killer (NK) cells, T-cells, B-cells, macrophages and monocytes, dendritic cells or any other immune cell which is capable of producing one or more immune effectors in response to direct or indirect epitope stimulation. The sample preferably comprises lymphocytes, more preferably T-lymphocytes. The terms "T-cells" and "T-lymphocytes" are used interchangeably herein. T-cells are capable of eliciting an immune response if they recognize the offered epitope. If the T-cells have been previously exposed to the tested epitope or an epitope for which the tested epitope is representative, a rapid re-stimulation of the T-cells with specific memory of that epitope occurs. These epitope-specific T-cells respond by secreting immune effectors such as, but not limited to interferon gamma (IFN-gamma, IFN-γ). Interferon gamma, or a subsequent immune effector or other molecule released in response to interferon gamma, can then be measured as specific marker of immune responsiveness against the tested epitope. Therefore, according to one embodiment, the sample comprises T-lymphocytes, preferably CD4+ helper T-cells and/or CD8+ cytotoxic T-cells. Preferably, the sample also comprises corresponding stimulator cells, in particular antigen presenting cells which are capable of presenting the tested epitope to the T-cells. However, suitable antigen presenting cells may also be added separately to the incubation composition. Respectively added antigen presenting cells (APC) include natural as well as artificial antigen presenting cells or particles. Stimulator cells such as irradiated autologous or HLA matched antigen-presenting cells can optionally be separately added to the incubation composition which then present the antigen to T-cells. This embodiment is feasible if the sample does not comprise respective stimulator cells necessary to induce a T-cell response. Artificial antigen presenting embodiments include but are not limited to particles or lipid vesicles with associated recombinant MHC molecules or peptides and recombinant co-stimulatory molecules. The immune effector-producing cells may be removed from a certain organ or tissue, for example intrahepatic lymphocytes (IHL).

Preferably, the sample is obtained fresh from a subject, but frozen samples also may be used in the methods described herein. According to one embodiment, the sample is a body fluid comprising immune cells. According to an embodiment, the sample is whole blood. By "whole blood" is meant blood from a subject that has not been substantially diluted or fractionated. According to one embodiment the whole blood sample is peripheral blood. Notwithstanding that whole blood is the preferred and most convenient sample for determining cell-mediated immune response activity, other samples also containing immune-effector producing cells can be used in general cell-mediated activity tests and assays. Examples include, but are not limited to lymph fluid, cerebral fluid, tissue fluid (such as bone marrow or thymus fluid) and respiratory fluid including nasal and pulmonary fluid and bronchioalveolar lavage. Also portions or derivatives of the above-mentioned samples, samples depleted of cells unnecessary for measuring the cell mediated immune response may be used as a sample and can be obtained by sample processing as is known in the art. For example, whole blood may be treated to remove components unnecessary for the assay such as red blood cells and/or platelets by methods known in the art, or whole blood may be processed to enrich for white blood cells. Also buffy coat cells or peripheral blood mononuclear cells (PBMC) can be obtained by methods known in the art and can be used as sample. According to one embodiment, fresh, isolated immune-producing cells are used as sample. Furthermore, as described above, cryopreserved cells comprising PBMC cells, can be used as source of the immune cells of the subject and thus as a sample. Thawed PBMC cells can be contacted with culture medium to provide the sample comprising immune cells which is then contacted and incubated with an epitope. According to one embodiment, the sample comprises all immune cells necessary for mediating a cellular immune response. However, as described above, it is also within the scope of the present invention to separately add stimulator cells, in particular antigen presenting cells. According to one embodiment, the sample comprises at least T-cells (T-lymphocytes) and NK cells (NK-lymphocytes). According to one embodiment, the sample is not diluted by more than 50%, 40%, 30%, 25%, 20%, 15%, 10%, 5%, 3° % or less prior to contacting the sample with the epitope. In a further embodiment, the sample is concentrated or enriched for immune cells by one or more methods known in the art before contacting the epitope.

The term "antigen" as used herein may refer to any molecule or agent that is capable of stimulating or re-stimulating an immune response, and in particular is capable of stimulating or re-stimulating a cellular immune response. It is contemplated herein that an epitope may be considered an antigen if it is capable of stimulating or re-stimulating a cellular immune response for example, but not limited to when used in an assay.

The term "peptide" as used herein includes polypeptides and proteins unless the context clearly indicates otherwise. According to one embodiment, the epitope is provided by a peptide. According to a further embodiment, the one or more peptides used as epitopes individually have a length defined by about 5 to about 100 amino acids, preferably about 7 to about 50 amino acids, for example, but not limited to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 continuous amino acids. The size of the peptides also may be described by a range of any two values recited above. According to an embodiment, the epitope is provided by a set of peptides from one or more different full length or part length peptides described by the sequences as defined herein. A peptide set comprises at least two peptides and includes in an embodiment a series of overlapping or non-overlapping peptides. A respective set of peptides may cover the entire length of or a part of a naturally occurring protein epitope. However, the peptides do not necessarily have to be overlapping or may overlap by a single amino acid or by multiple amino acids. According to one embodiment, a peptide set is used which encompasses from 80-100% of a naturally occurring betaretroviral peptide or protein epitope.

Following contacting the biological sample with the one or more epitopes, the combined composition is incubated for a period of time and conditions suitable for the production of immune effectors, for example interferon-gamma, TNF-alpha and the like. Without wishing to be limiting in any manner, typical incubations may be from 2 to 50 hours depending on assay conditions. The present methods contemplate any such time periods, for example, but not limited to 2 to 40 hours, 5 to 30 hours, 8 to 24 hours, 16 to 24 hours, or a time period in between including, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 hours.

According to one embodiment, the compositions and methods of the invention employ an anticoagulant, for example but not limited to heparin in the collection and/or processing of a biological sample that includes blood. Adding an optional non-reducing sugar may increase the release of immune effectors, such as interferon gamma, thereby increasing the sensitivity of the assay.

The immune effectors to be detected may be any of a range of molecules which are produced in response to cell activation, stimulation or re-stimulation by an epitope. In preferred embodiments, epitopes are betaretrovirus-specific epitopes. More than one immune effector or a pattern of immune effectors released upon contact of the sample with the tested epitope can be detected. The immune effector to be measured may be produced by immune cells, in particular can be produced by lymphocytes such as T-cells, in particular CD4+ helper T-cells and/or CD8+ cytotoxic T-cells. Thus, in some embodiments, the method is based upon measuring the production of one or more immune effectors by cells of the immune system, in particular T-cells, in response to antigenic stimulation. However, also non-immune cells may release immune effectors in response to stimulation, respectively re-stimulation, of immune cells by the epitope as they are stimulated by the immune effectors that are released by the immune cells, in particular by immune effectors such as IFN-gamma released by re-stimulated T-cells. These immune effectors can also be an important source of information. Therefore, according to an embodiment, the immune effector to be detected may be the immediate effector molecule produced by effector T cells in response to epitope re-stimulation. In other embodiments, a downstream immune effector is measured. For example, IFN-gamma or other immediate immune effectors produced by immune cells, in particular by T-cells that are (re) stimulated by the tested epitope, can be measured. However, as described above, these molecules often induce or enhance the production of further immune effectors by other cells. The production of these further (downstream) immune effectors may also be measured. The present invention also encompasses detecting more than one type of immune effector. According to one embodiment, the presence or level of a pattern of immune effectors is detected either alone or in addition to immediate immune effectors such as IFN-gamma. A respective pattern comprises more than two, preferably more than three different immune effectors. Analyzing a respective pattern can provide valuable information of the immune status of the subject. Specific immune effectors or patterns of immune effectors can be characteristic for specific diseases.

The epitopes in the embodiments may be derived from the viral genomic sequence of human betaretrovirus. The retroviral genome may be divided into three categories, Gag, Pol and Env. "Gag" is often used to describe a polyprotein and is an acronym for Group Antigens (ag). Gag proteins often code for the viral matrix (MA) capsid (CA) and nucleoproteins (NC). "Pol" refers to the reverse transcriptase. "Env" refers to the envelope protein. The group antigens form the viral core structure, RNA genome binding proteins, and are the major proteins comprising the nucleoprotein core particle. SEQ ID Nos: 1-146 represent peptides that are derived from Gag and Env peptides. In these cases. SEQ ID Nos: 1-15, and 37-79 refer to Gag-derived peptides and SEQ ID Nos: 16-36 and 80-146 refer to Env-derived peptides. Any peptides encoded by the betaretroviral genome may be used.

In a preferred embodiment, which is not meant to be limiting in any manner, the peptide is an isolated immunogenic betaretrovirus peptide comprising at least 7, 8, 9, 10, 11, 12, 13, 14, 15, 16, 17, 18, 19, or 20 contiguous amino acids as defined by any one of SEQ ID Nos: 1-36 or a plurality of said peptides. A composition is also contemplated, the composition comprising one or more betaretrovirus peptides, each peptide at least 75% identical, for example, but not limited to 76%, 77%, 78%, 79%, 80%, 81%, 82%, 83%, 84%, 85%, 86%, 87%, 88%, 89%, 90%, 91%, 92%, 93%, 94%, 95%, 95%, 97%, 98%, 99% or 100% to anyone of SEQ ID Nos: 1-146, for example 1-36.

An amino acid sequence exhibiting at least 70% identity thereto is understood to include sequences that exhibit 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9% or 100% identity, or a value therein between to SEQ ID NOs. 1-146. Further, the amino acid may be defined as comprising a range of sequence identities as defined by any two of the values listed or any values therein between. Such polypeptides are contemplated alone and for use in the methods as described herein.

As described above, the composition may comprise one or more isolated immunogenic peptides wherein the epitopes may be isolated peptides or they may be attached covalently or noncovalently to a carrier, macromolecule, polymer, substrate, support, culture dish, multiwall plate or the like optionally via any spacer, linker known in the art. The peptides may comprise a sequence of at least 7 contiguous amino acids according to any one of SEQ ID Nos. 1-146 but may comprise additional amino acids, non-amino acids, peptide sequences which are heterologous to betaretrovirus. The peptide sequence as described above and herein throughout which is greater than 7 amino acids in length, for example, but not limited to 8, 9, 10, 11, 12, 13, 14, 15, 16, 17, 18, 19, 20, 21, 22, 23, 24, 25, 26, 27, 28, 29, 30, 40, 50, 60, 70, 80, 90, 100 or more amino acids. Further the length may be defined by a range of any two values noted above or any two values therein between. For example, but not to be considered limiting in any manner, the invention contemplates amino acids having a size range of between 7 and 12, or between 9 and 11. Ranges outside those specifically described are also contemplated. Said peptide may be a tetrameric peptide or other multimeric construct. The monomeric units of said tetramer or other multimeric construct may comprise the same sequence as described herein and throughout according to SEQ ID Nos: 1-146, for example 1-36.

The epitopes may be mimotopes. Mimotope may refer to a macromolecule, often a peptide, which mimics the structure of an epitope. In some cases, mimotope refers to peptide mimic of all types of binding sites. Mimotopes may cause an antibody response similar to the one elicited by the epitope. An antibody for a given epitope epitope will recognize a mimotope which mimics that epitope. Mimotopes may be obtained from phage display libraries through biopanning. Vaccines utilizing mimotopes may be developed. Mimotopes may also be a kind of peptide aptamers.

According to one embodiment, the immune effector to be measured is a cytokine such as a lymphokine, interleukin or chemokine. Interferon (IFN) such as IFN-gamma is a particularly useful as immune effector to be measured/determined. Other examples of immune effectors include, but are not limited to a range of cytokines such as interleukins (IL), IL-2, IL-4, IL-6, IL-8 (CXCL8), IL-10, IL-12, IL-13, IL-16 (LCF) or IL-17, IL-1α (IL-1F1), IL-1β (IL-1F2), IL-1rα (IL-1F3), Tumor Necrosis Factor alpha (TNF-α), Transforming Growth Factor beta (TGF-β), a Colony Stimulating Factor (CSF) such as Granulocyte (G)-CSF or Granulocyte Macrophage (GM)-CSF, complement component 5a (C5a), Groa (CXCL1), sICAM-1 (CD54), IP-10 (CXCL10), I-TAC (CXCL11), MCP-1 (CCL2), MIF (GIF), MIP-1α (CCL3), MIP-1 (CCL4), Serpin E1 (PAI-1), RANTES (CCL5) or MIG (CXCL9). In some embodiments, the present disclosure provides methods wherein the immune effector to be detected is a cytokine, a component of the complement system, perforin, defensin, cathelicidin, granzyme, Fas ligand, CD-40 ligand, exotaxin, a cytotoxin, a chemokine or a monokine. In preferred embodiments, the immune effector detected is IFN-gamma. Thus, according to a preferred embodiment, the present disclosure provides a method for measuring a cell mediated immune response in a subject, said method comprising collecting a sample from said subject into a collection vessel wherein said sample comprises cells of the immune system which are capable of producing IFN-gamma following stimulation by an epitope, incubating said sample with an epitope and optionally a non-reducing sugar and then measuring the presence of or the change in the level of an IFN-gamma wherein the presence or change in the level of IFN-gamma is indicative of the capacity of said subject to mount a cell-mediated immune response.

Also a combination of immune effectors can be detected. The assay may comprise detecting an immune effector or combination of immune effectors, in particular cytokines, released in response to the stimulation with the epitope and characteristic for the disease or condition to be analyzed. Furthermore, the level of the one or more immune effector may be screened alone or in combination with other biomarkers or disease indicators.

The presence or elevation in the level of an immune effector may be detected. As described above, the presence, absence or level of an immune effector may be indicative of the level or capacity of cell-mediated immune responsiveness of the subject against the tested epitope. In particular, the method allows for the determination as to whether the subject has previously encountered the tested epitope or an epitope that shows cross-reactivity with the tested epitope such as the pathogen to be detected. Thereby, it can be determined whether the subject is capable of eliciting a cell-mediated immune response against said epitope, respectively the epitope, pathogen or disease the tested epitope is representative for. In such cases, reactivity of an immune-effector producing cell, such as a CD8+ T-lymphocyte, to a betaretrovirus-specific antigen, such a peptide with at least part of one of SEQ ID Nos: 1-146, may be indicative of an infection or a previous infection by betaretrovirus.

Figure 7A:
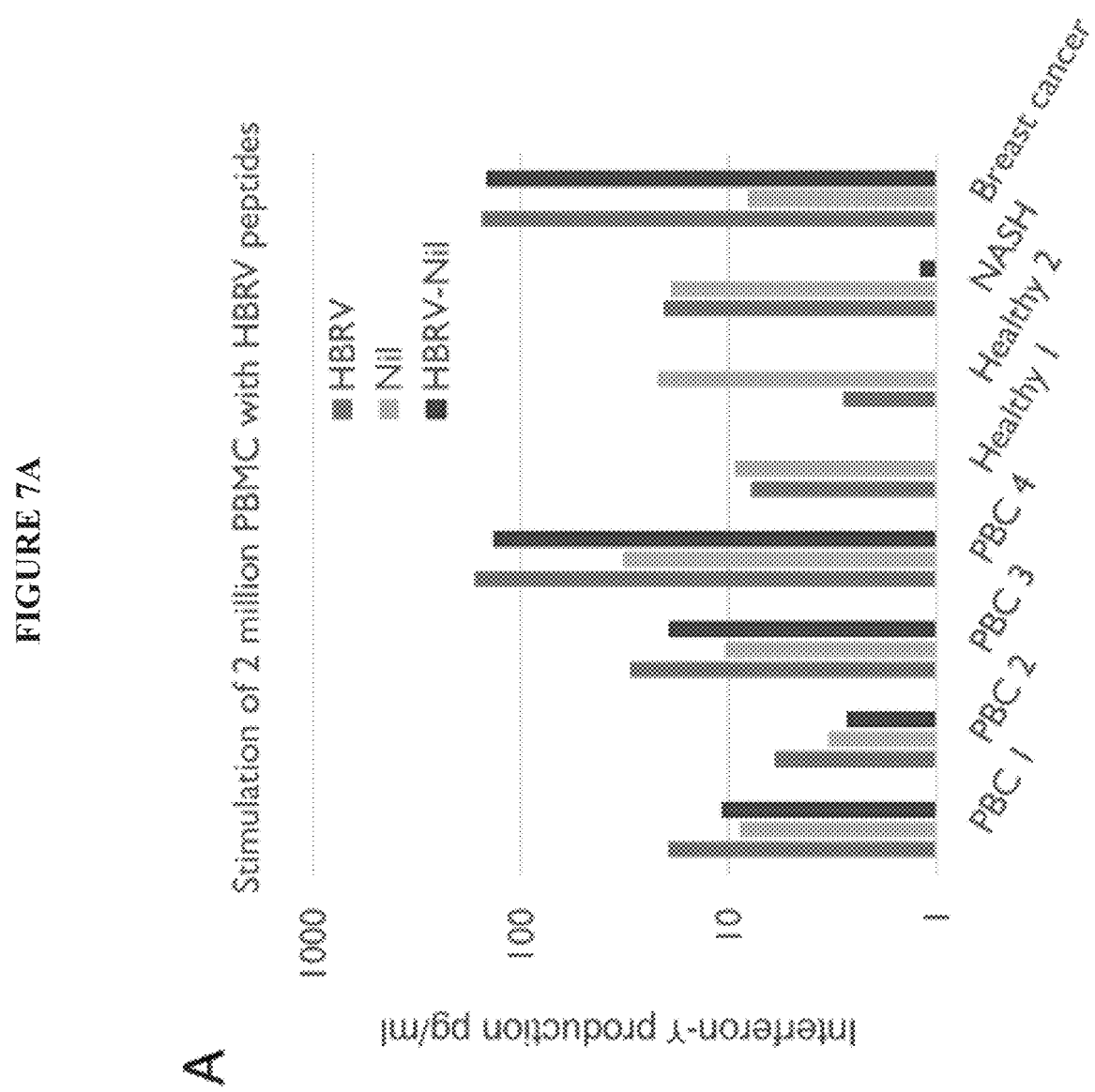
Figure 7B:
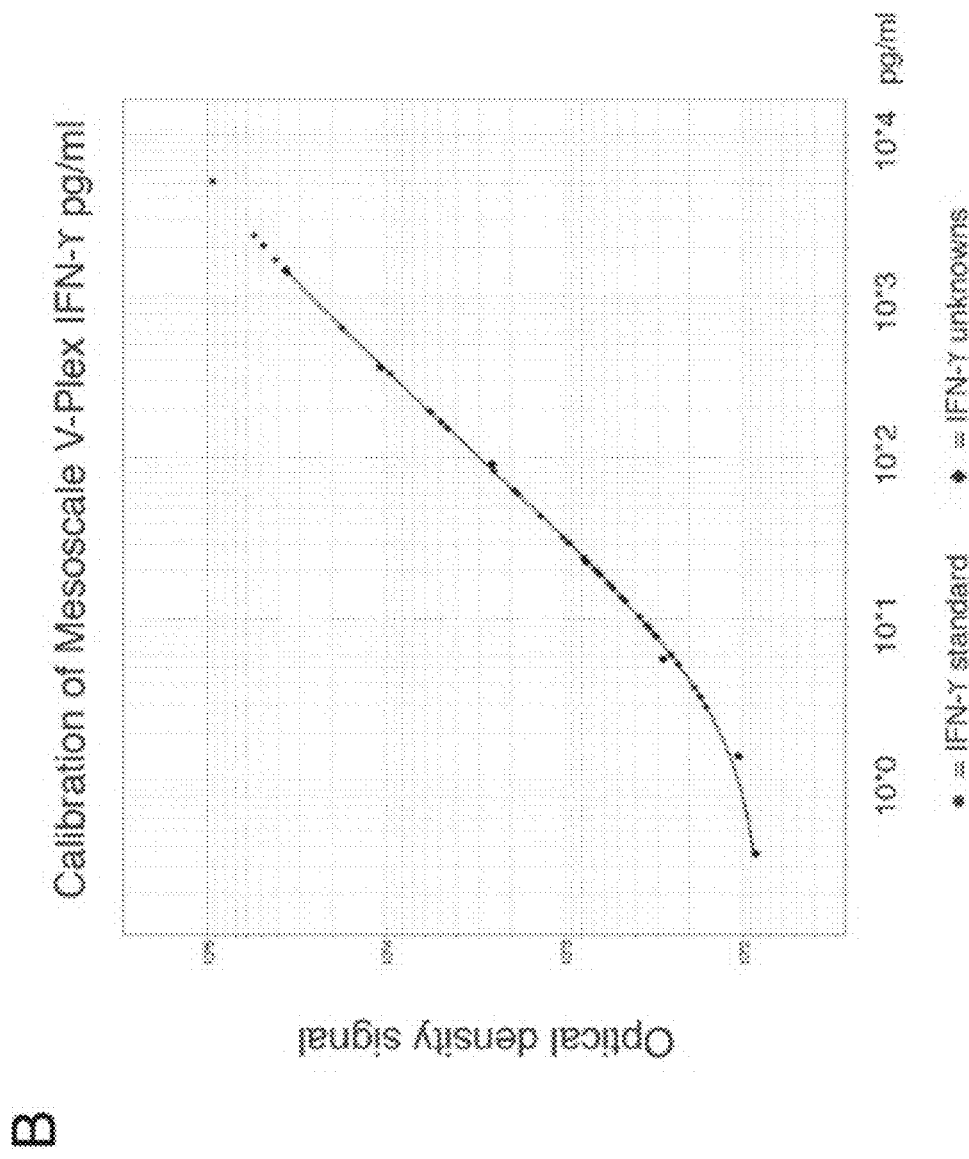

In an embodiment of the present invention, the presence of an immune effector, the level of an immune effector, an increase or change in the level of an immune effector is indicative of a betaretroviral infection. In a further embodiment, betaretroviral infection is present when above a predetermined threshold. The threshold may be an amount that is greater than, for example, one standard deviation, two standard deviations, three standard deviations or more from the mean of a control group, such as one or more negative controls without a betaretroviral-specific epitope added. A sensitive ELISA method may be used, for example Mesoscale V-Plex ELISA. A sufficiently broad linear range for measuring an immune effector such as IFN-γ is preferable, for example from 1,000 to below 10 µg/ml (FIG. 7B)

as well as validated reproducibility of IFN-γ detection. In some cases, the threshold is an average of background responses from healthy subjects without HBRV response using 1+, 2+ or 3+ standard deviation, as performed for the HBRV Env, Gag or both Env and Gag epitope ELISA. In some cases, the threshold of IFN-gamma measured is about 10 µg/ml or greater, for example, but not limited to 7.5, 8.0, 8.5, 9.0, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 32, 34, 36, 38, 40, 42, 44, 46, 48, 50, 55, 60, 65, 70, 75, 80, 85, 90, 100, 110, 120, 130, 140, 150, 175, 200, 225, 250, 300, 350, 400, or 500 μg/ml.

As noted above, the production of the immune effectors may be measured by incubating the biological sample containing immune effector-producing cells with one or more betaretrovirus-specific epitopes and determining if the immune effectors produced are greater than a control step of incubating the biological sample comprising immune effector-producing cells with one or more non-betaretrovirus-specific epitopes. Said greater production of immune effectors may be indicative of an infection or risk of a betaretrovirus infection. Positive and negative controls suitable controls are considered. One example of a negative control is incubating immune-effector producing cells in the absence of an epitope or other stimulus. One example of a positive control is incubating the biological sample comprising immune effector-producing cells with a lymphocyte stimulant (such as ionomycin and phorbal myristate acetate (PMA)). In such cases, the controls may be used to demonstrate that the lymphocytes are active and a lack of production of immune effectors may be indicative of no infection of betaretrovirus.

Antibodies produced by the subject's immune system may be used. Disclosed herein is a method for determination of a betaretrovirus infection in a subject, the method comprising obtaining a biological sample from the subject, the biological sample comprising one or more human antibodies, incubating the biological sample with one or more betaretrovirus-specific epitopes, the virus specific epitopes having a sequence of at least 7 contiguous amino acids according to any one of SEQ ID Nos: 1-36, and measuring the binding of the one or more human antibodies with the one or more betaretrovirus-specific epitopes, wherein binding is indicative of an infection by the betaretrovirus.

The assay may comprise incubating a sample comprising antibodies generated by the subject against the epitope. The betaretrovirus-specific epitopes may be immobilized and measuring the binding of the one or more human antibodies comprises washing with at least one anti-human antibody-indicator hybrid. The method described in these cases may resemble an ELISA assay to detect the presence of antibodies generated by the subject. In such cases, the assay further comprises incubating the biological sample with anti-betaretrovirus epitope antibodies. Examples of the epitopes include any fragment of the Env proteins, which includes any of SEQ ID NO: 1-36 and 80-146.

The detection of the immune effector may occur at the peptide or protein level or at the nucleic acid level, in particular, the immune effector mRNA expression level. Consequently, reference to detecting the "presence or level" of the immune effector includes direct and indirect data. For example, the presence or amount of immune effectors can be directly determined using appropriate detection methods such as ELISA or ELISpot. However, in one embodiment, the presence or level of the immune effector is measured based on its RNA expression level. High levels of immune effector mRNA are indirect data showing increased levels of the immune effector. Suitable methods for determining the mRNA expression level of a target gene are well-known in the prior art. Accordingly, in some embodiments, the immune effector may be detected using ligands or binding molecules such as antibodies specific for the effector molecule or by measuring the level of expression of genes encoding the immune effector.

According to one embodiment, the immune effector is detected by using a ligand which specifically binds the immune effector. Ligands to the immune effectors are particularly useful in detecting and/or quantitating these molecules. Cells comprised in the incubation composition can be removed prior to detecting the immune effector. Techniques for the detection assays that can be used are known in the art and include, for example, radioimmunoassays, sandwich assays, ELISA and ELISpot.

Antibodies to the immune effectors are particularly useful as ligands. Reference to "antibodies" includes parts of antibodies specifically binding the immune effector such as Fab fragments, mammalianized (humanized) antibodies, deimmunized antibodies, recombinant or synthetic antibodies and hybrid and single chain antibodies. Both polyclonal and monoclonal antibodies are obtainable by immunization with the immune effectors or antigenic fragments thereof and either type is utilizable for immunoassays. Methods of obtaining both types of antibodies are well known in the art. Polyclonal antibodies are less preferred but are relatively easily prepared by injection of a suitable laboratory animal with an effective amount of the immune effector, or antigenic part thereof, collecting serum from the animal and isolating specific sera by any of the known immunoadsorbent techniques. Although antibodies produced by this method are utilizable in virtually any type of immunoassay, they are generally less favored because of the potential heterogeneity of the product. The use of monoclonal antibodies in an immunoassay is particularly useful because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. Antibodies against specific immune effectors are also commercially available.

A wide range of immunoassay techniques are available as can be seen by reference to U.S. Pat. Nos. 4,016,043, 4,424,279 and 4,018,653. Respective assays that can be used in conjunction with cell-mediated immune response tests described herein to detect the produced immune effectors are also described in WO2004/042396, WO2008/113119, WO2010/009494 and WO2011/075773. Also Clay et al. "Assays for monitoring cellular immune responses to active immunotherapy of cancer; Clinical Cancer Research 2001; 7:1127-1135" describe several methods for monitoring cellular immune responses, thereby also describing suitable assays for detecting the immune effectors produced in response to antigen (re)stimulation. Therein, ELISA-based assays, ELISpot assays and nucleic acid-based assays such as the measurement of cytokine mRNA levels by real-time quantitative RT-PCR are described. Optionally, when determining the level of immune effector based on its RNA expression level, the obtained data can be normalized to the expression of control gene, such as for example CD8. Respective methods can also be used in conjunction with the present invention to detect the produced immune effectors. According to one embodiment, a nucleic acid based assay for detecting the presence or level of an immune effector is used. Nucleic acids, in particular RNA, can be isolated from the incubation composition or the cellular portion thereof using standard methods well-known in the prior art. Preferably, the presence or elevation of the expression of the immune effector is detected in this embodiment using amplification based assays, preferably PCR based assays. Isolated RNA can first be reverse transcribed to cDNA prior to amplification using primers and/or probes specific for the immune effector to be detected. Preferably, the detection is quantitative. One suitable method is quantitative real-time RT (reverse transcription) PCR. The detection of the immune effector may be a quantitative detection.

The enzyme-linked immunospot (ELISpot) assay is an immunoassay that measures the frequency of cytokine-secreting cells at the single-cell level. ELISpot combines plate-based Enzyme Linked Immunosorbent Assays (ELISAs) with membrane-based Western blotting technologies for assessing immune cell function based on secreted analytes. In this assay, cells may be cultured on a surface coated with a specific capture antibody in the presence or absence of stimuli. Proteins, such as cytokines, that are secreted by the cells may be captured by the specific antibodies on the surface. After an appropriate incubation time, cells may be removed and the secreted molecule may be detected using a detection antibody in a similar procedure to that employed by the ELISA. The detection antibody may be biotinylated and followed by a streptavidin-enzyme conjugate or the antibody may be directly conjugated to an enzyme. Using a substrate with a precipitating product may produce visible spots on the surface. Each spot may corresponds to an individual cytokine-secreting cell, which can be quantified. The assay can be performed manually or by automation. Equipment used in a typical ELISpot assay is well known in the art and may include Multi Screen® HTS 96-well Plates, 8-well strip, Plate sealing tape, and MultiScreen® 8-Well Strip Support Frame. References in the art for ELISpot procedures include: Barabas, Sascha et al. "An optimized IFN-γ ELISpot assay for the sensitive and standardized monitoring of CMV protein-reactive effector cells of cell-mediated immunity" BMC immunology vol. 18, 1 14. 7 Mar. 2017; Sedgwick J. D., and Holt P. G. (1983) A solid-phase immunoenzymatic technique for the enumeration of specific antibody-secreting cells. J. Immunol. Methods 57, 301-309; Czerkinsky C. C., Nilsson L. A., Nygren H., Ouchterlony O., and Tarkowski A. (2983) A solid-phase enzyme-linked immunospot (ELISPOT) assay for enumeration of specific antibody-secreting cells. J. Immunol. Methods 65, 109-121; Czerkinsky C., Moldoveanu Z., Mestecky J., Nilsson L. A., and Ouchterlony O. (1988) A novel two colour ELISPOT assay. I. Simultaneous detection of distinct types of antibody-secreting cells. J. Immunol. Methods 115, 31-37; Tanguay S. and Killion J. J. (1994) Direct comparison of ELISPOT and ELISA-based assays for detection of individual cytokine-secreting cells. Lymphokine Cytokine Res. 13, 259-263; Saletti et al., Nature Protocols 8, 1073-1087 (2013), all of which are incorporated by reference.

It will be understood by those skilled in the art that a wide variety of methods and techniques known in the art may be used in carrying out certain embodiments of the present invention. By way of example, detection of the immune effectors and viral integration into host cells as described herein may be accomplished using a variety of approaches and techniques well-known in the field, for example those described in U.S. Pat. No. 8,568,968 to Lenz and references cited therein, which are all incorporated by reference in their entirety. Lenz describes various conventional techniques in the art, including those described in:

Sambrook and Russell eds. MOLECULAR CLONING: A LABORATORY MANUAL, 3.sup.rd edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney 5.sup.th edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins-eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)) all of which are incorporated by reference.

Those skilled in the art will understand that a wide variety of expression systems can be used to produce the proteins or fragments thereof as defined herein. With respect to in vitro production, the precise host cell used is not critical to the invention. The proteins or fragments thereof can be produced in a prokaryotic host (such as *E. coli* or *B. subtilis*) or in a eukaryotic host (Examples include: *Saccharomyces* or *Pichia*, mammalian cells, such as COS, NIH 3T3, CHO, BHK, 293, or HeLa cells; insect cells; or plant cells). The methods of transformation or transfection and the choice of expression vector will depend on the host system selected and can be readily determined by one skilled in the art. Transformation and transfection methods are described, for example, in Ausubel et al. (1994) Current Protocols in Molecular Biology, John Wiley & Sons, New York; and various expression vectors may be chosen from those provided, as in Cloning Vectors: A Laboratory Manual (Pouwels et al., 1985, Supp. 1987) and by various commercial suppliers.

In addition, a host cell may be chosen which modulates the expression of the inserted sequences, or modifies/processes the gene product in a specific, desired fashion. Such modifications (glycosylation) and processing (cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the expressed protein.

Mass spectrometry techniques may be used to identify proteins as described herein, for example those described in Mass Spectrometry and Genomic Analysis, ed. Housby, 2001 which is incorporated by reference.

Antibodies may be useful in some embodiments, the production and use of which are well known in the art, for example is described in Current Protocols in Immunology, Coico et al., John Wiley & Sons, which is hereby incorporated by reference.

The present invention also contemplates one or more antibodies that are capable of binding to any one of the amino acid or polypeptide sequences described herein. In a preferred embodiment, the antibody is a monoclonal antibody. Also contemplated are nucleotide sequences comprising the one or more antibodies describe herein.

Antibodies, including monoclonal antibodies can be prepared using a wide variety of techniques known in the art including, for example, hybridoma, recombinant, and phage display technologies, or a combination thereof. For example, monoclonal antibodies can be produced using hybridoma techniques including those known in the art, for example, but not wishing to be considered limiting in any manner, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). The term "monoclonal antibody" refers to an antibody that is derived from a single clone, including any eukaryotic, prokaryotic, or phage clone, and is not meant to be limited by the method by which it is produced.

Methods for producing and screening for specific antibodies using hybridoma technology are routine and also well known in the art. As an example, but not to be considered limiting in any manner, an animal capable of eliciting an immune response to an epitope (for example, mice) can be immunized with an epitope, for example a polypeptide as described herein, a fragment or variant thereof, a fusion protein, or a cell expressing an epitope, polypeptide or fragment or variant thereof. Once an immune response is detected, antibodies specific for the epitope are detected in the mouse serum, the mouse spleen is harvested and splenocytes isolated. The splenocytes are then fused by well known techniques to any suitable cells, for example, mylenoma cells or the like. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating polyclonal and monoclonal antibodies as well as antibodies produced by the method comprising culturing a hybridoma cell secreting an antibody wherein, preferably, the hybridoma is generated by fusing splenocytes isolated from a mouse or other animal immunized with a polypeptide of the invention with myeloma cells and then screening the hybridomas resulting from the fusion for hybridoma clones that secrete an antibody able to bind a polypeptide of the invention.

Other well known methods for producing antibodies also may be employed. Such methods include but are not limited to Epstein Barr Virus (EBV) transformation protocols, for example, in Current Protocols in Immunology, Coligan et al., Eds., 1994, John Wiley & Sons, NY, which is hereby incorporated in its entirety by reference.

The present invention also contemplates the production of antibody fragments which recognize the polypeptides as described herein, fragments thereof or specific epitopes therein. Such antibody fragments may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

Antibodies that bind to an epitope can also be generated using various phage display methods known in the art. In phage display methods, functional antibody domains are displayed on the surface of phage particles which carry the polynucleotide sequences encoding them. In a particular embodiment, such phage can be utilized to display epitope binding domains expressed from a repertoire or combinatorial antibody library (human or murine). Phage expressing an antigen binding domain that binds the antigen of interest can be selected or identified with antigen, using labeled antigen or antigen/epitope bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make antibodies that bind to an antigen include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240: 1041-1043 (1988), herein incorporated by reference.

Examples of additional techniques which may be contemplated herein include those which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). Methods for producing chimeric antibodies are also known in the art and may be employed if desired. See, Morrison, Science 229:1202 (1985); Oi et al., BioTechniques 4:214 (1986); Gillies et al., (1989) J. Immunol. Methods 125:191-202; U.S. Pat. Nos. 5,807,715; 4,816, 567; and 4,816,397, which are incorporated herein by reference in their entirety.

For the production of antibodies, various hosts including, for example, goats, rabbits, rats, mice and humans, can be immunised with the target protein, or with a fragment or peptide thereof that has immunogenic properties. Depending on the host species, various adjuvants may be used to increase the immunological response. Such adjuvants include, but are not limited to, Freund's adjuvant, mineral gels such as aluminium hydroxide, and surface active substances such as lysolecithin, pluronic polyols, polyanions, peptides, oil emulsions, Keyhole limpet hemolysin (KLH), and dinitrophenol. Examples of adjuvants used in humans include, for example, BCG (bacilli Calmette-Guerin) and *Corynebacterium parvum*.

According to some embodiments of the present invention, the epitopes may be in a pharmaceutical composition. Forms of administration include, but are not limited to, injections, solutions, creams, gels, implants, pumps, ointments, emulsions, suspensions, microspheres, particles, microparticles, nanoparticles, liposomes, pastes, patches, tablets, capsules, transdermal delivery devices, sprays, aerosols, or other means familiar to one of ordinary skill in the art. Pharmaceutical formulations of the present invention can be prepared by procedures known in the art using well-known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (starch, sugars, mannitol, and silicic derivatives); binding agents (carboxymethyl cellulose and other cellulose derivatives, alginates, gelatin, and polyvinyl-pyrrolidone); moisturizing agents (glycerol); disintegrating agents (paraffin); resorption accelerators (quaternary ammonium compounds); surface active agents (cetyl alcohol, glycerol monostearate); adsorptive carriers (kaolin and bentonite); emulsifiers; preservatives; sweeteners; stabilizers; coloring agents; perfuming agents; flavoring agents; lubricants (talc, calcium and magnesium stearate); solid polyethyl glycols; and mixtures thereof.

The formulations can be so constituted that they release the active ingredient only or preferably in a particular location, possibly over a period of time (i.e., a sustained-release formulation). Such combinations provide yet a further mechanism for controlling release kinetics. The coatings, envelopes, and protective matrices may be made, for example, from polymeric substances or waxes and the pharmaceutically acceptable carrier.

Pharmaceutically acceptable carriers include liquid carriers, solid carriers or both. Liquid carriers are aqueous carriers, non-aqueous carriers or both, and include, but are not limited to, aqueous suspensions, oil emulsions, water-in-oil emulsions, water-in-oil-in-water emulsions, site-specific emulsions, long-residence emulsions, sticky-emulsions, micro-emulsions and nano-emulsions. Solid carriers are biological carriers, chemical carriers or both and include, but are not limited to, viral vector systems, particles, microparticles, nanoparticles, microspheres, nanospheres, minipumps, bacterial cell wall extracts and biodegradable or non-biodegradable natural or synthetic polymers that allow for sustained release of the oligonucleotide compositions. Emulsions, minipumps and polymers can be implanted in the vicinity of where delivery is required (Brem et al. J. Neurosurg. 74:441, 1991). Methods used to a solid carrier, covalent coupling to the surface of the solid carrier, either directly or via a linking moiety, and covalent coupling to the polymer used to make the solid carrier. Optionally, mycobacterial cell wall-DNA complexes can be formulated by adding non-ionic or ionic polymers such as polyoxyethylenesorbitan monooleates (TWEENs), chitosan, chemically modified chitosan, hyaluronic acid, sodium hyaluronate salts, chondroitin sulphate, heparin, heparin sulphate or chemical modifications of these molecules. The molecular weight range of such polymers can range from less than 100 Da to greater than 5 million Da depending on the degree of polymerization and chemical modification therein.

Preferred aqueous carriers include, but are not limited to, water, saline and pharmaceutically acceptable buffers. Preferred non-aqueous carriers include, but are not limited to, a mineral oil or a neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, squalane, squalene, soybean oil, canola oil, palm oil, olive oil and myglyol, wherein the fatty acids can be saturated or unsaturated. Optionally, excipients may be included regardless of the pharmaceutically acceptable carrier. These excipients include, but are not limited to, anti-oxidants, buffers, and bacteriostats, and may include suspending agents and thickening agents.

The compositions of the present invention can be applied in the form of creams, gels, solutions, suspensions, liposomes, particles, or other means known to one of ordinary skill in the art of formulation and delivery of the compositions. Ultrafine particle sizes can be used for inhalation delivery of therapeutics. Some examples of appropriate formulations for subcutaneous administration include, but are not limited to, implants, depot, needles, capsules, and osmotic pumps. Some examples of appropriate formulations for vaginal administration include but are not limited to creams and rings. Some examples of appropriate formulations for oral administration include but are not limited to: pills, liquids, syrups, and suspensions. Some examples of appropriate formulations for transdermal administration include but are not limited to gels, creams, pastes, patches, sprays, and gels. Formulations suitable for parenteral administration include, but are not limited to, aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. Extemporaneous injection solutions and suspensions may be prepared from sterile powders, granules and tablets commonly used by one of ordinary skill in the art.

Embodiments in which the compositions of the invention are combined with, for example, one or more pharmaceutically acceptable carriers or excipients may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Preferred unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art.

Additional steps may be taken after the assay is performed. For example, additional tests may be used to confirm that the subject is positive for PBC, cancer and/or an infection by betaretrovirus. Additional testing may take the form of blood tests, smears, reverse transcriptase PCR (RT-PCR) for viral nucleic acids (such as DNA or RNA), serologic reactivity to retroviruses and retroviral sequences within the liver, or additional biochemical assays such as ELISAs, cell counting (e.g. flow cytometry) or ELISPOT. Present or previous Betaretroviral infection may also be determined or confirmed by finding integration sites within the host cell (FIG. 11). Genetic tests may be used to find integration sequences into various cells in the patient. Combination tests may be used. In such cases, the methods described herein may be used to detect IFN-gamma production by leukocytes. The biological sample may also be tested for antibodies that bind betaretroviral epitopes. These antibodies may bind sequences that comprise all or part of the SEQ ID Nos: 1-146. The antibodies may be detected using immunoassays, such as ELISA, sandwich assays and any other methods described herein or in the art.

Additional steps may include treatment of the subject following the results of the assay. In cases where the assay indicates a betaretroviral infection, antiretroviral therapy may be given to the subject. Antiretroviral therapy may comprise a single retroviral therapeutic or combination antiretroviral therapy (cART). cART may be a combination of antiretrovirals or an antiretroviral and another type of therapeutic, such as a protease inhibitor. Combination antiretroviral therapy may include the administration of Raltegravir and Emtricitabine/tenofovir to a subject. In such cases and others, a subject with PBC and treatment by antiretrovirals may experience improvement of liver function, for example normalization in hepatic biochemistry and histological improvement. A subject with cancer, such as breast cancer, may be administered antivirals and/or anti-cancer therapeutics after indication of a betaretroviral infection. Examples of anti-viral therapy may, for example, be found in Randomized Clinical Trial: Combination antiretroviral therapy with Tenofovir-Emtricitabine and Lopinavir-Ritonavir in patients with primary biliary cholangitis. E. Lytvyak, I. Hosamani, A. Montano-Loza, L. Saxinger, A. Mason. Canadian Liver Journal, 2019, 10.3138/can-livj.2018-0020, herein incorporated by reference in its entirety.

Treatment may also comprise the use of any inhibitors of retroviral enzymes, such as reverse transcriptase, protease, and integrase. Any broad spectrum antivirals that inhibit HBRV may also be used, such as GSK-3beta inhibitors, cyclophilin inhibitors and others known in the art. Other antiretroviral therapeutics are considered, including: abacavir, atazanavir, atripla, darunavir, descovy, dolutegravir, efavirenz, elvitegravir, emtricitabine, etravirine, eviplera, evotaz, fosamprenavir, genvoya, kivexa, lamivudine, lopinavir, ritonavir, maraviroc, nevirapine, odefsey, raltegravir, rezolsta, rilpivirine, stribild, tenofovir, triumeq, truvada, zidovudine (AZT) and others.

It should be understood that following any method as described herein related to testing, identifying or screening, such methods may further comprise additional testing or screening for one or more additional genetic mutations, blood tests, blood enzyme tests, counseling, providing support resources or administering an additional pharmaceutical agent based on the results of such tests and/or screens. Similarly, it is further contemplated that such methods may be preceded by one or more steps, for example but not limited to selecting a subject that is infected or thought to be at risk of infection, or selecting a subject that is has been diagnosed with cancer or liver ailments.

The present invention also contemplates products and kits for practicing the methods of the present invention. For example, a kit may comprise: one or more collection vessels for the biological sample, one or more betaretroviral epitopes according to at least 7 nucleotides of any of SEQ ID Nos: 1-36, a lymphocyte stimulant, such as phorbal myristate acetate (PMA) or ionomycin, for a positive control, an auto antigen such as pyruvate dehydrogenase complex-E2 (PDC-E2), a non-reducing sugar, an anti-coagulant, one or more buffers to dilute the sample, or a combination thereof. The betaretrovirus-specific epitopes may be plural epitopes, with at least one of the pair derived from the Gag pool and the other of the pair derived from the Env pool. In some cases, twenty or more epitope sequences are used. In an exemplary embodiment, the kit comprises individual heparinized tubes with reagents for receiving the biological sample. For example a tube with pooled HBRV peptides of any one of SEQ ID Nos: 1-36, a negative control tube, a positive control tube with PMA and a tube with PDC-E2 immunodominant peptides.

Any kits described herein may include peptides in a collection tube to incubate with the biological sample, which may include whole blood or purified lymphocytes. Having the peptides in a pre-mixed state within the tube may decrease handling time during use of the kit. The kit may also include ingredients for carrying out a method for detecting IFN-gamma. The kit may include known ingredients in the art to carry out an ELISA assay, or ELISpot assay. The kit may also be used to prepare the sample for analysis off-site. For example, the sample may be mixed with buffers to stabilize the sample during travel off-site. Analysis at a location removed from the collection site may include ELISA, ELISpot, flow cytometry or a combination thereof.

The present invention also contemplates a kit comprising one or more components, such as, but not limited to one or more primary antibodies that are capable of binding to any amino acid or polypeptide sequence described herein, one or more secondary antibodies that are capable of binding the primary antibody, one or more solutions or reagents for immunological analysis, for example, a blocking or binding solution, one or more polypeptides as described herein, said polypeptide optionally conjugated to a non-protein carrier, polypeptide carrier, heterologous amino acid sequence, support, dish, bead, well, macromolecule, multi-well plate or the like. The polypeptide may be attached via a linker or spacer. Purification media may be in the kit, for example, but not limited to remove abundant plasma proteins from samples that are collected, centrifugation media, immunoabsorption columns, resin, buffers, enzymes, one or more supports, beads, wells, dishes, multiwell plates, instructions for using any component or practicing any method as described herein, or any combination thereof.

Biomolecules, compounds, and/or compositions as described herein may include one or more pharmaceutically acceptable excipients, diluents, and/or carriers. A pharmaceutically acceptable carrier, diluent, or excipient may include any suitable carrier, diluent, or excipient known to the person of skill in the art. Examples of pharmaceutically acceptable excipients may include, but are not limited to, cellulose derivatives, sucrose, and starch. The person of skill in the art will recognize that pharmaceutically acceptable excipients may include suitable fillers, binders, lubricants, buffers, glidants, and disentegrants known in the art (see, for example, Remington: The Science and Practice of Pharmacy (2006)). Examples of pharmaceutically acceptable carriers, diluents, and excipients may be found in, for example, Remington's Pharmaceutical Sciences (2000-20th edition) and in the United States Pharmacopeia: The National Formulary (USP 24 NF 19) published in 1999.

In another embodiment, there is provided herein a method for diagnosing presence of a betaretrovirus infection, diagnosing cancer or risk of cancer, diagnosing a liver disease or risk of liver disease, or any combination thereof, said method comprising: determining a level of anti-HBRV Su antibodies in a subject, wherein an elevated level of anti-HBRV Su antibodies in the subject as compared to a healthy control or comparator is indicative of presence of a betaretrovirus infection, cancer or risk of cancer, a liver disease or risk of liver disease, or any combination thereof. In an embodiment, the step of determining may comprise exposing an antibody-containing biological sample from the subject to one or more HBRV Su epitopes to determine a presence or level of anti-HBRV Su antibodies in the sample. In another embodiment, the step of determining may comprise exposing an antibody-containing biological sample from the subject to a peptide comprising an HBRV Su epitope, the peptide being immobilized to a solid support, membrane, or other support. In another embodiment, the peptide may comprise full length HBRV Su, or a portion thereof comprising at least one epitope, or an amino acid sequence having at least about 80% sequence identity (such as 80%, 81%, 82%, 83%, 84%, 85%, 86%, 87%, 88%, 89%, 89%, 90%, 91%, 92%, 93%, 94%, 95%, 96%, 97%, 98%, or 99% sequence identity, or any range spanning between any two of these values) therewith. In another embodiment, the step of determining may comprise performing an ELISA-type assay in which an antibody-containing biological sample from the subject is exposed to a solid support coated with a peptide comprising at least one HBRV Su epitope such that anti-HBRV Su antibodies, if present, bind the peptide, and are subsequently detected and/or quantified.

In an embodiment, the peptide may comprise HBRV SU protein sequence (SEQ ID NO: 147), or a portion thereof comprising at least one epitope, or an amino acid sequence having at least about 80% sequence identity (such as 80%, 81%, 82%, 83%, 84%, 85%, 86%, 87%, 88%, 89%, 89%, 90%, 91%, 92%, 93%, 94%, 95%, 96%, 97%, 98%, or 99% sequence identity, or any range spanning between any two of these values) therewith:

(SEQ ID NO: 147)
MPNHQSGSPTGSSDLLLSGKKQRPHLALRRKRRSEMRKINRKVRRMNL

APIKEKTAWQHQALIFEAEEVLKTSQTPQTSLTLFLALLSVLGPPPVT

GESYWAYLPKPPILHPVGWGNTDPIRVLTNQTIYLGGSPDFHGFRNMS

GNVHFEGKSDTLPICFSFSFSTPTGCFQVDKQVFLSDTPAVDNNKPGG

KGDKRRMWELWLTTLGNSGANTKLVPIKKKLPPKYPHCQIAFKKDAFW

EGDESAPPRWLPCAFPDQGVSFSPKGTLGLLWDFSLPSPSVDQSDQIR

SKKDLFGNYTPPVNKEVHRWYEAGWVERTWFWENSPKDPNDRDFTALV

PHTELFRLVAASRYLILKRPGFQEHDMIPTSACATYPYAILLGLPQLI

DIEKRGSTFHISCSSCRLTNCLDSSAYDYAAIIVKRPPYVLLPVDIGD

EPWFDDSAILTFRYATDLIRA.

In another embodiment, there is provided herein a method for treating a betaretrovirus infection, cancer, a liver disease, or any combination thereof, comprising diagnosing the subject as being in need to treatment using an of the method or methods as described herein, and then treating the subject with an anti-viral, anti-cancer, or anti-liver disease therapy, or any combination thereof.

In another embodiment of the above methods, the biological sample may comprise a serum sample from the subject.

In another embodiment, there is provided herein an expression vector encoding HBRV Su or a portion thereof. In another embodiment, the expression vector may comprise a TAP tag at the 3' terminus of the HBRV Su (or portion thereof), at least one (preferably, more than one, such as at least 2-6, for example, 4) copies of M-PMV cytoplasmic transport element (CTE) downstream, or both. In another embodiment, there is provided herein a cell transfected with an expression vector as described herein. In an embodiment, the cell may be stably transfected with the expression vector. In another embodiment, there is provided herein an isolated peptide comprising HBRV Su, or an epitope-containing portion thereof. In another embodiment, there is provided herein a peptide comprising HBRV Su or a portion thereof comprising at least one HBRV Su epitope, the peptide being covalently attached or physically associated with a dish, bead, well, support, macromolecule, carrier or the like, optionally via a tetramer, linker or spacer.

In another embodiment, the expression vector may comprise the following HBRV SU nucleic acid sequence (SEQ ID NO: 148) or a sequence having at least about 80% sequence identity therewith, or a nucleic acid sequence encoding the same peptide or a sequence having at least about 80% sequence identity therewith:

(SEQ ID NO: 148)
atgccgaatcaccaatctgggtccccgaccggttcatccgaccttta ctgagcggaaagaagcaacgcccacacctggcactgcggagaaaacgc cgcagcgagatgagaaagatcaacaggaaagtccggaggatgaatcta gcccccatcaaagagaagacggcttggcaacatctgcaggcgttaatc ttcgaagcggaggaggttcttaaaacctcacaaactccccaaacctct ttgactttatttcttgctttgttgtctgtcctcggcccccgcctgtg accggggaaagttattgggcttacctacctaaaccacctattctccat cccgtgggatggggaaatacagaccccattagagttctgaccaatcaa accatatatttgggtgggtcacctgactttcacgggtttagaaacatg tctggcaatgtacattttgaggggaagtctgatacgctccccatttgc ttttccttctccttttctaccccccacaggctgctttcaagtagataag caagtatttctttctgatacaccgcggttgataataataaacctggg ggaaagggtgataaaaggcgtatgtgggaactttggttgactactttg gggaactcaggggccaatacaaaactggtccctataaaaagaagttg ccccccaaatatcctcactgccagatcgcctttaagaaggacgccttc tgggagggagacgagtctgctcctccacggtggttgccttgcgccttc cctgaccaggggggtgagttttctccaaaagggacccttgggttactt tgggatttctcccttcctcgcctagtgtagatcagtcagatcagatt agaagcaaaaaggatctatttggaaattatactcccctgtcaataaa gaggttcatcgatggtatgaagcaggatgggtagaacgtacatggttc tgggaaaattctcctaaggatcccaatgatagagattttactgctcta gttccccatacagaattgtttcgcttagttgcagcctcaagatatctt attctcaaaaggccaggatttcaagaacatgacatgattcctacatct gcctgtgctacttacccttatgccatattattaggattacctcagcta atagatatagagaaaagaggatctacttttcatatttcctgttcttct tgtagattgactaattgtttagattcttctgcctacgactatgcagcg atcatagtcaagaggccgccatacgtgctgctacctgtagatattggt gatgaaccatggtttgatgattctgccattctaacctttaggtatgcc acagatttaattcgagcc.

Figure 14A:
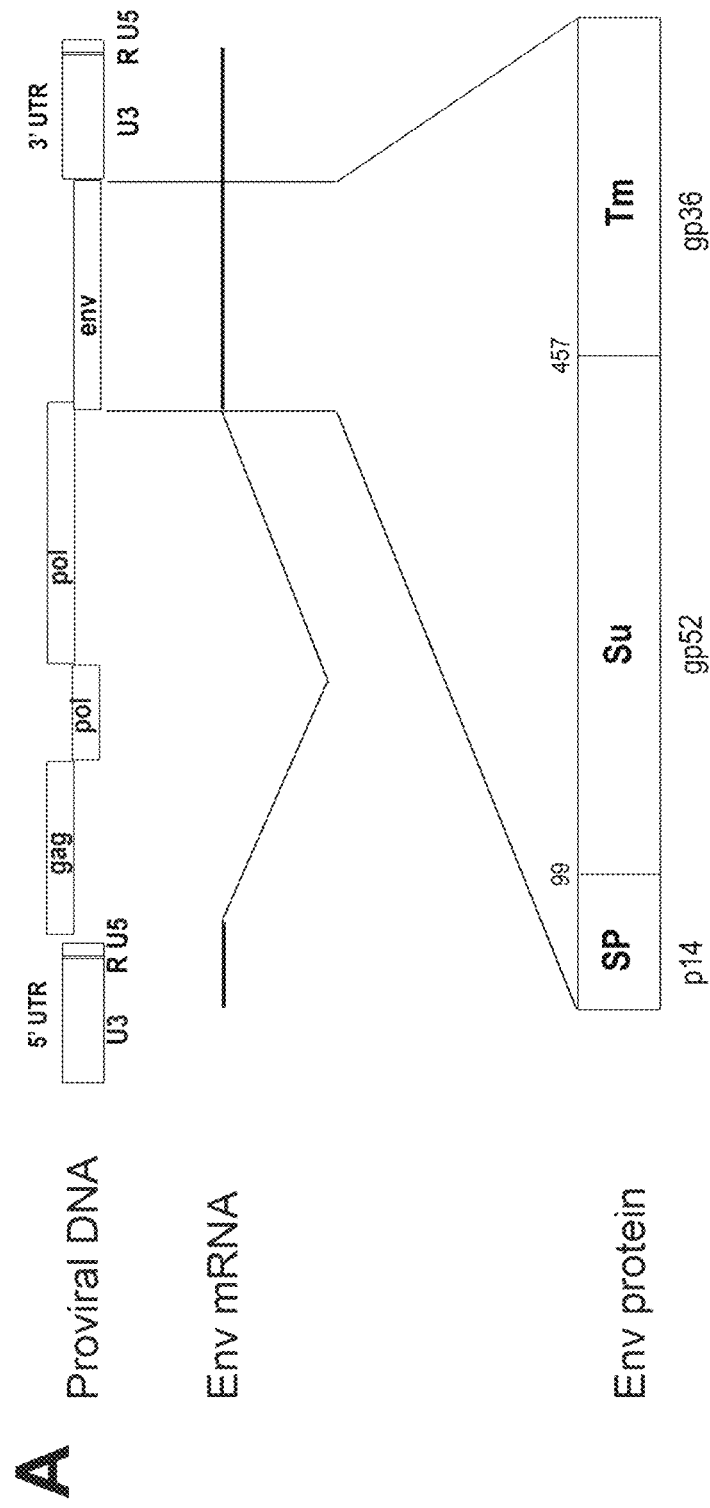

See FIG. 14, and descriptions thereof, for further details regarding exemplary expression vectors as described herein and features thereof.

In another embodiment, there is provided herein a kit for diagnosing presence of a betaretrovirus infection, diagnosing cancer, diagnosing a liver disease, or any combination thereof, in a subject. In an embodiment, the kit may comprise an expression vector encoding HBRV Su or one or more epitopes thereof as described herein, a cell transfected with the expressing vector, an isolated peptide comprising HBRV Su (or at least one epitope thereof), or any combination thereof. In an embodiment, the peptide comprising HBRV Su (or at least one epitope thereof) may be covalently attached or physically associated with a dish, bead, well, support, macromolecule, carrier or the like, optionally via a tetramer, linker or spacer. In another embodiment, the kit may further comprise any one or more of a biological sample collection vessel, an anticoagulation agent, one or more buffers, a needle for drawing a biological sample, and any instructions, products, reagents, compositions, culture dishes or plates, glassware, plasticware, medical devices, the like, or any combination thereof, to carry out a method as described herein. In some embodiments, the kit may further comprise one or more human betaretrovirus-specific epitopes each of at least 7 amino acids according to SEQ ID Nos: 1-146, such as SEQ ID Nos: 1-36.

In another embodiment, there is provided herein a method for preparing a peptide comprising HBRV Su or a portion thereof, said method comprising: transfecting a cell with an expression vector as described herein expressing HBRV Su or a portion thereof, culturing the transfected cell, and collecting the peptide comprising HBRV Su or portion thereof produced by the cell. In an embodiment, the collecting may comprise precipitating the peptide comprising HBRV Su or portion thereof (with, for example, TCA, or another suitable agent). In another embodiment, the culturing may comprise culturing the cell in medium supplemented with serum (for example, 10% FBS, or another such serum supplementation) for a first period, which may be followed by replacing the media with serum-free (or substantially serum-free) media for a second period, and collecting the peptide comprising HBRV Su or portion thereof from the serum-free media and/or cells therein. In an embodiment, the collecting may comprise column chromatography purification to collect the peptide comprising HBRV Su or portion thereof. In another embodiment, the step of culturing may comprise selecting for transfected cells stably expressing the HBRV Su or portion thereof, performing cell expansion, or both. In another embodiment, the expression vector may comprise more than one (e.g. multiple copies, such as 2-6, or 4 for example) copy of CTE downstream of the Su coding region to enhance HBRV Su expression and/or secretion.

In another embodiment, there is provided herein a method for preparing HBRV Su or a portion thereof comprising at least one epitope, said method comprising: transfecting a cell with an expression vector encoding tagged HBRV Su (or portion theref); expanding the transfected cells in medium supplemented with FBS or another suitable serum supplementation; replacing the medium with serum-free (or substantially serum-free) medium (which, in another embodiment, may be performed when cells reach, for example, about 95% confluence); incubating the cells, and collecting the supernatant following incubation; and collecting and purifying the HBRV Su (or portion thereof) from the supernatant by His-Tag column purification, or another suitable purification technique suitable for the conditions and/or tag being used. In another embodiment, the method may comprise a step of selecting for transfected cells stably expressing the HBRV Su or portion thereof, which may, in certain embodiments, be performed before the step of expanding. In another embodiment, the expression vector may comprise more than one (eg. multiple copies, such as 2-6, or 4 for example) copy of CTE downstream of the Su coding region to enhance HBRV Su expression and/or secretion.

One or more currently preferred embodiments have been described by way of example. It will be apparent to persons skilled in the art that a number of variations and modifications can be made without departing from the scope of the invention as defined in the claims.

The present invention will be further illustrated in the following examples.

EXAMPLES

Example 1

Characterization of a human betaretrovirus in subjects with PBC. Our lab first took an unbiased approach to cloning a HBRV from subjects with PBC after finding electron microscopy evidence of viral like particles in biliary epithelium, serologic reactivity to retroviruses and retroviral sequences within the liver. The virus was found predominantly in lymph nodes rather than in the liver, similar to observations of MMTV infection in mice. RT-PCR and immunochemistry revealed that 75% of lymph nodes were positive for virus but only 29% of PBC subjects had detectable HBRV RNA in the liver.[3] Others have reported that the virus is difficult to find in the liver[31,13] and similarly we have shown that hepatic HBRV DNA is rarely detected in the liver (~5%) using nested-PCR. This has caused controversy because HBRV is absent or below the limits of detection in liver and blood and large case control studies have not been performed.[5] Using the "gold standard" to confirm retroviral infection, we used ligation mediated (LM)-PCR and next generation sequencing to identify more than 2,000 unique integration sites. We confirmed that the provirus was transcriptionally active by detecting HBRV RNA in two thirds of PBC subjects' biliary epithelium using in situ hybridization and a Quantigene probe assay.[5] We addressed the hypothesis that HBRV is below the limits of detection in liver by identifying infection in the majority of PBC subject's biliary epithelium. Of importance, HBRV integration was less readily detected within the liver confirming our prior experience. We isolated HBRV from subject samples and demonstrated proviral integrations and HBRV RNA in the majority of PBC subjects' biliary epithelium at the site for disease (FIGS. 11A and 11B).

Our lab also linked HBRV and MMTV with the PBC mitochondrial phenotype of increased and aberrant pyruvate dehydrogenase-E2 (PDC-E2) expression thought to trigger AMA expression[3,6] We recently characterized this phenotype as a hypermetabolic state—with both aerobic glycolysis and increased oxidative phosphorylation—associated with elevated levels of mitochondrial DNA suggestive of a "leaky mitochondria" syndrome.[32] A similar phenotype with mitochondrial biogenesis can be initiated by WNT/β-catenin signaling, activated during MMTV infection by insertional mutagenesis proximal to wnt1 and fgr3 genes.[33] In PBC subjects, we have co-located HBRV in cells with increased PDC-E2 expression, in lymph nodes and in bile ducts; similar observations were made in lymphoid tissues and bile ducts of PBC mouse models.[3,34] As a major reservoir for HBRV in humans, we used lymph node homogenates in co-culture with healthy biliary epithelial cells to establish an in vitro model of PBC.[6] The cholangiocytes developed cell surface PDC-E2 expression in co-culture with PBC lymph node whereas control nodes had no such effect. Pure isolates of MMTV and HBRV promoted the phenotype but control viruses did not.[3] Taken together, these studies address some of Koch's postulates in vitro and provide a mechanism for viral induction of autoimmunity by co-expression of a sequestered protein with viral proteins to the immune system and induce loss of tolerance to self.[36] We therefore found that PBC cholangiocytes have a hypermetabolic, mitochondrial biogenesis phenotype. We also showed that HBRV and MMTV mediate a disease-specific phenotype that triggers the generation of anti-mitochondrial antibodies in vivo and in vitro in humans and mice.

Figure 11A:
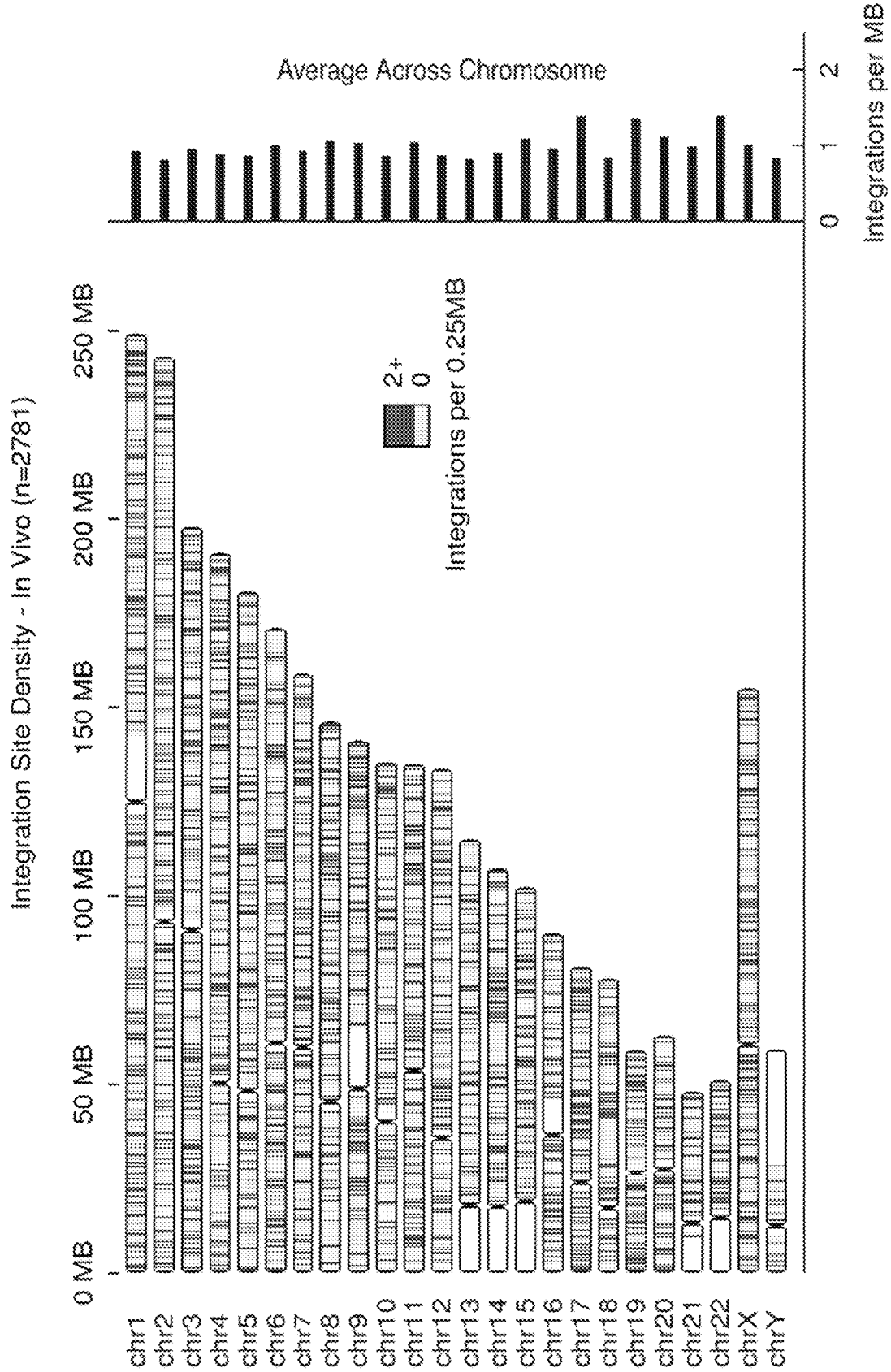
Figure 11B:
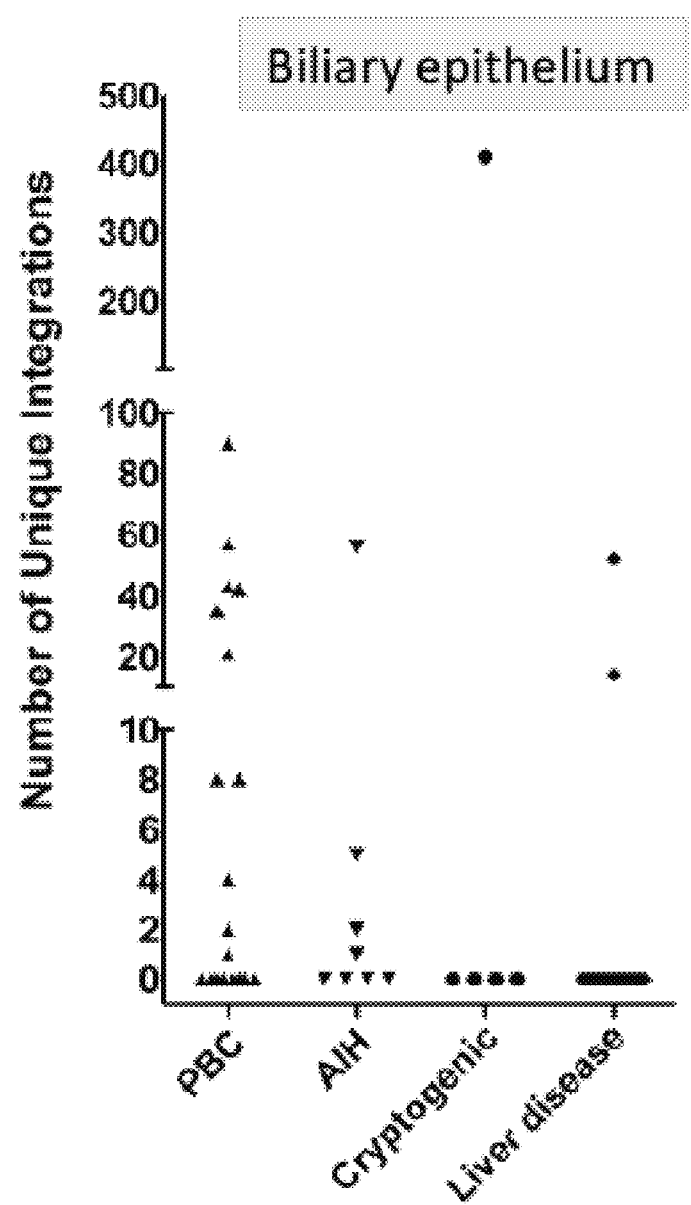
Figure 13A:
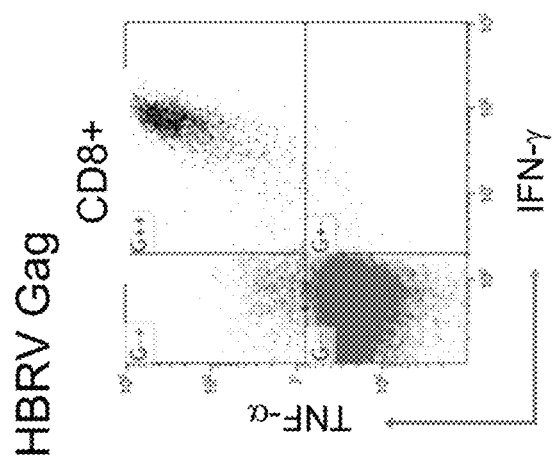
Figure 13B:
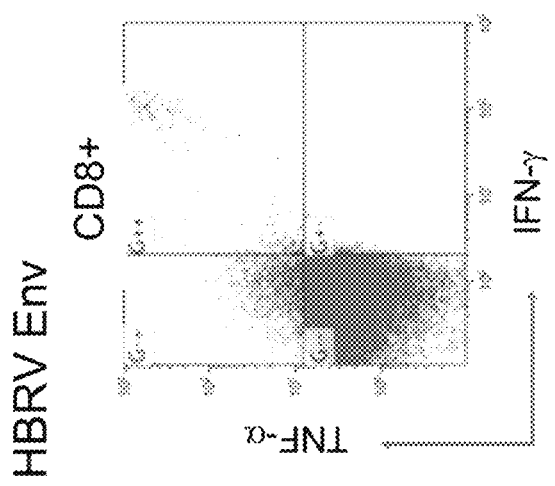
Figure 13C:
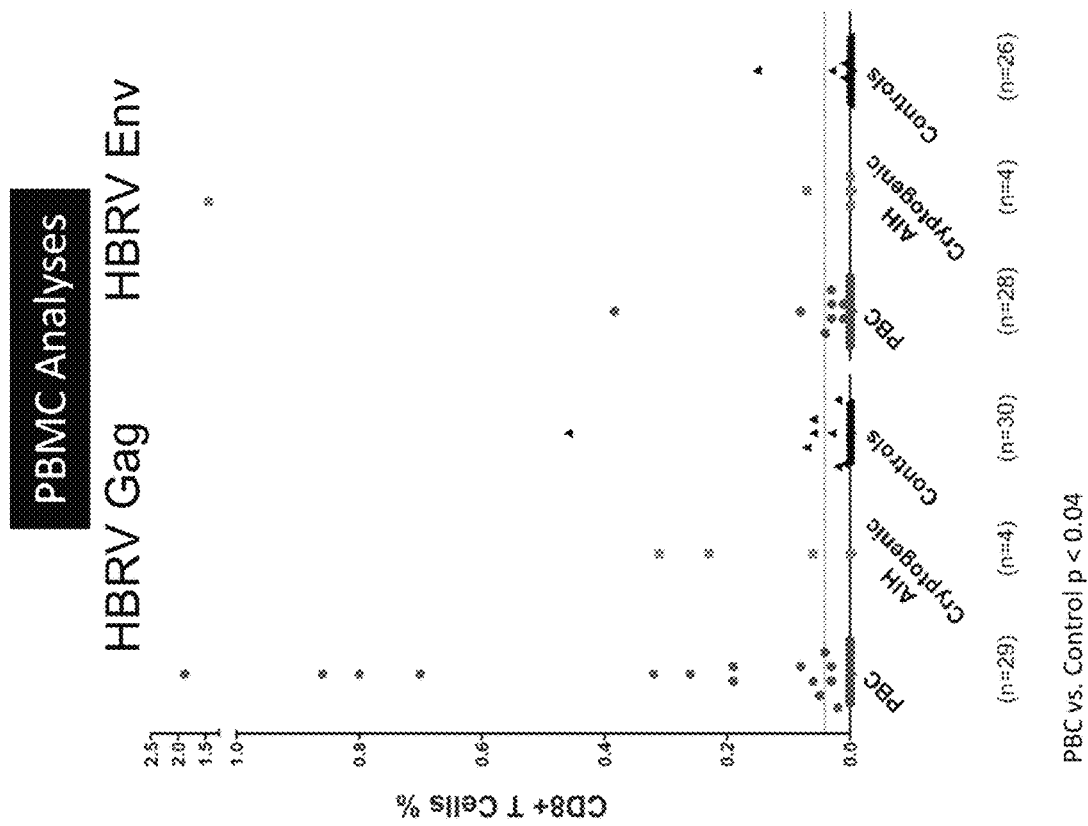

In some cases, betaretrovirus infection is not cleared because the virus integrates into the genome (FIGS. 11A and 11B). Accordingly, the spread may be controlled by active immune response. A patient with controlled infection, such as those with breast cancer, may have high level response. It may not be possible to differentiate who has active vs inactive disease because PBC patients may get the disease due to poor lymphocyte responses, whereas breast cancer patients may have better immune responses. Breast cancer patients may not get liver disease but during early infection, the virus may have already circulated to the breast, where it can later cause cancer by integrating its DNA into the breast epithelial cells.

Example 2: Cellular Immune Responses to HBRV

Figure 3:
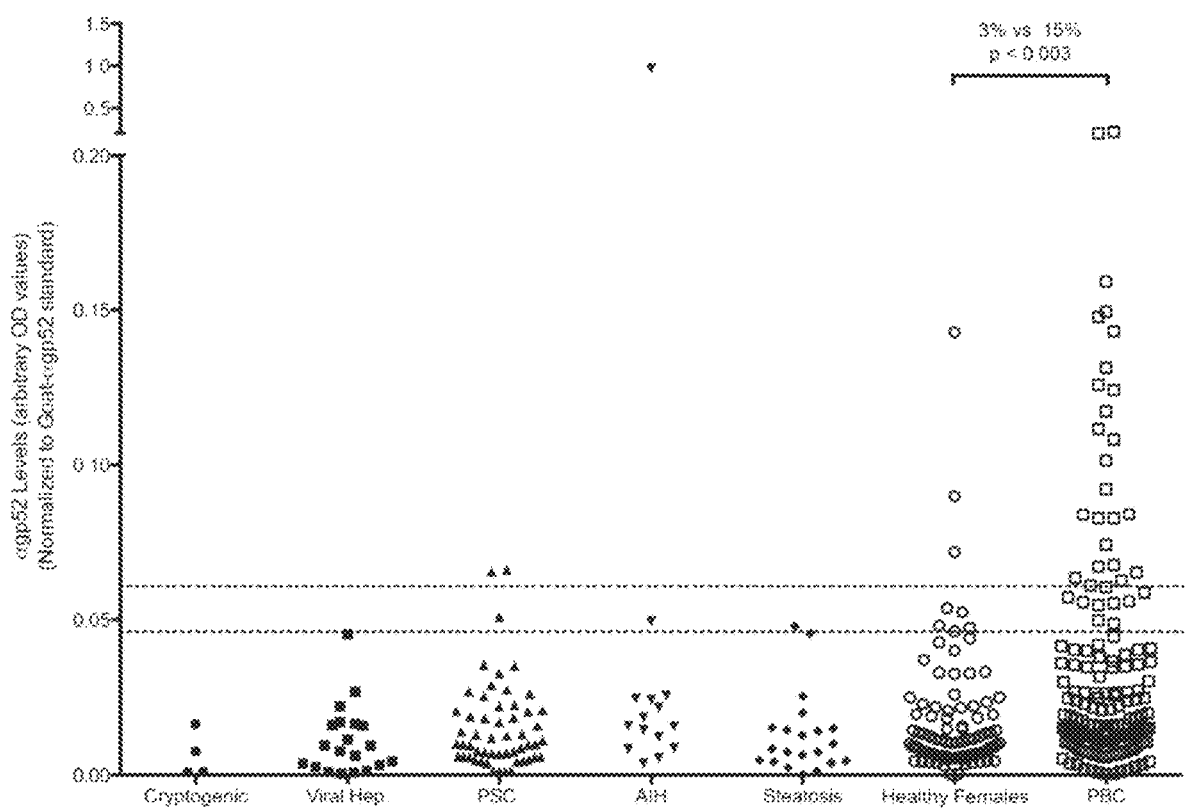
FIG. 3 depicts HBRV Env reactivity in liver disease. Dotted lines represent average plus 2× and 3× standard deviation of background responses (also see FIG. 16).
Figure 4A:
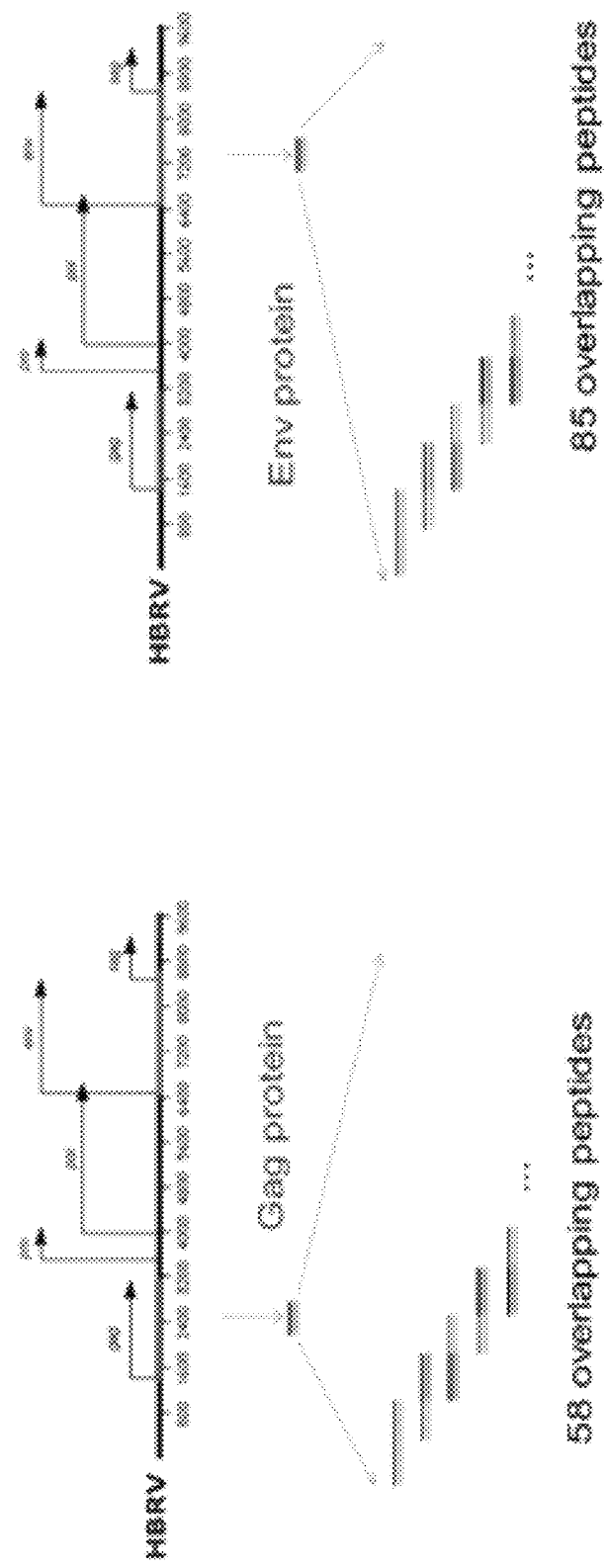
FIG. 4A is a schematic depicting the human betaretroviral genome and the synthesis of Gag and Env peptide fragments.

To determine proinflammatory lymphocyte responses to HBRV, overlapping 20mer peptides were synthesized (Mimotopes) and aggregated into pools for Gag (n=58) and Env (n=85) or used individually to stimulate lymphocyte preparations (FIG. 4A). Characterized PDC-E2 epitopes from the antigenic inner lipoyl domain were assessed as well.[51] Using flow cytometry analysis to detect intra-cellular production of IFN-γ and tumor necrosis factor (TNF)-α, we observed that 38% of PBC subjects had CD8+ responses to HBRV Gag and 7% to Env peptides. No response was observed using characterized PDC-E2 peptides, presumably because the low frequency of autoreactive lymphocytes found in PBMC (FIG. 3). We demonstrated both humoral and cellular immunity to HBRV in PBC subjects.

Mapping Immunodominant HBRV Peptides.

Figure 4B:
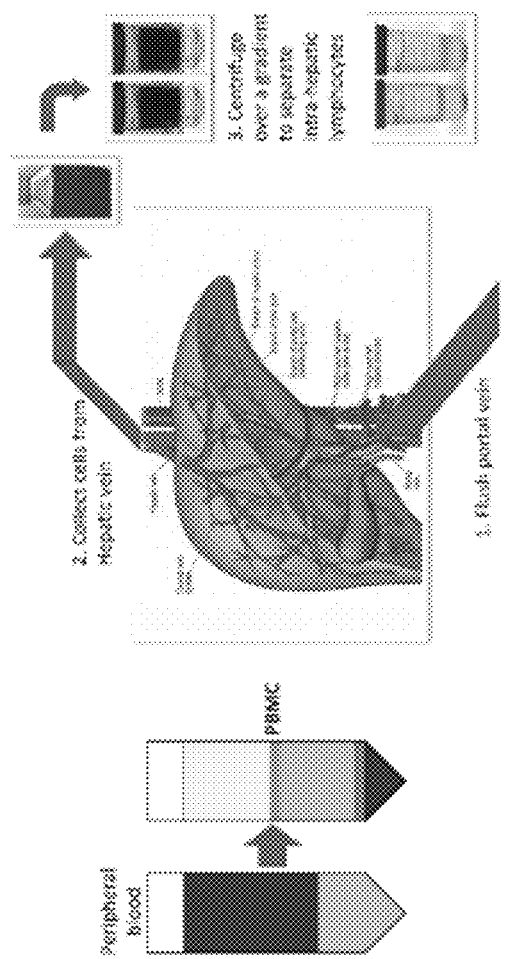
FIG. 4B is a schematic depicting a procedure for obtaining intra-hepatic lymphocytes from a liver.
Figure 5:
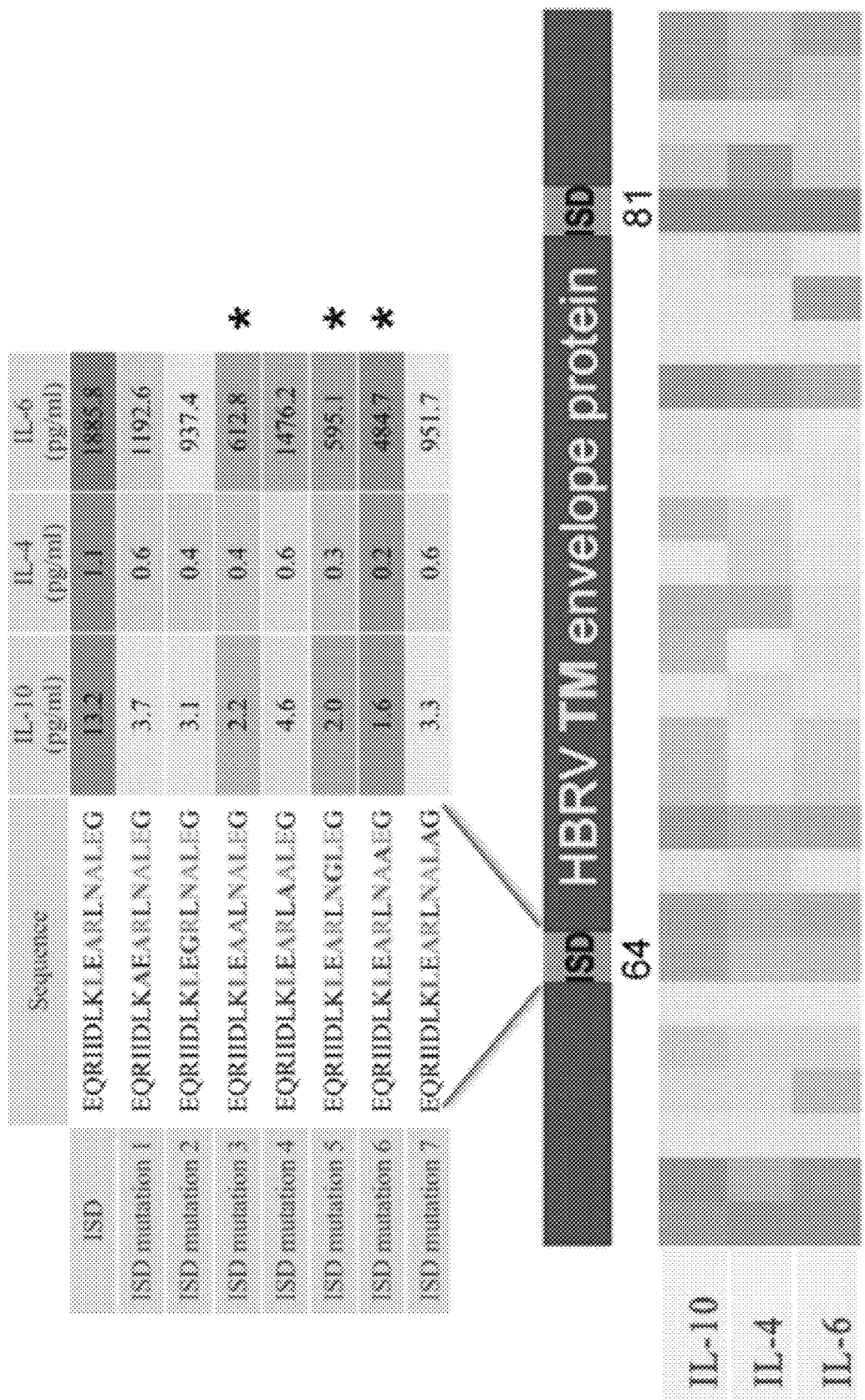
FIG. 5 is a heat map representing immunosuppressive activity of fragments of the transmembrane envelope protein of HBRV.
Figure 6A:
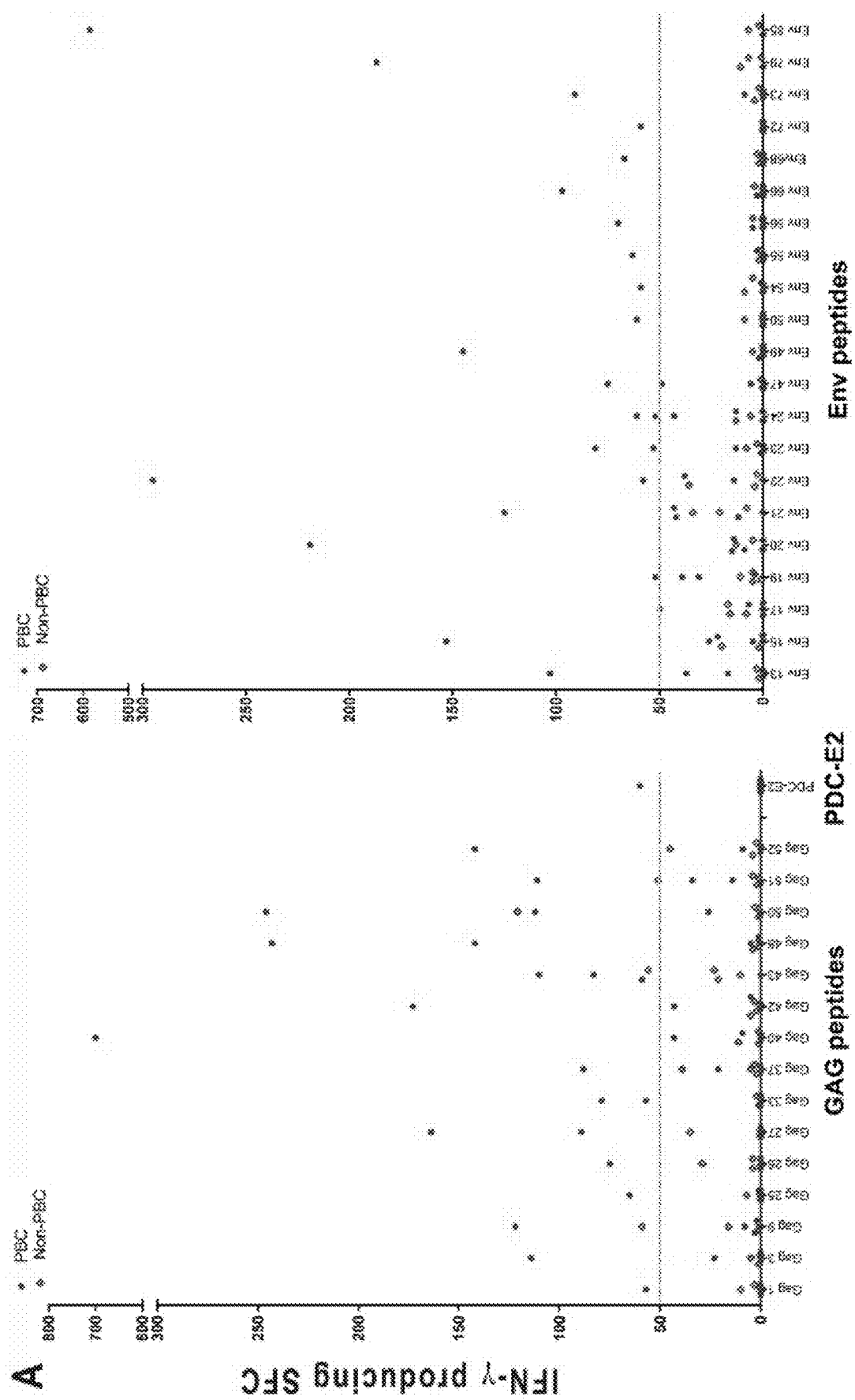
FIGS. 6A and 6B depict ELISPOT analyses

We isolated intrahepatic lymphocytes (IHL) to increase the likelihood of finding HBRV reactive lymphocytes (FIG. 3). IHL were extracted from 5 PBC subjects and 4 LT controls, as described[58] (FIG. 4B). ELISPOT was employed to detect IFN-γ spot forming colonies (SFC) using 100,000 IHL per reaction. Individual peptides from HBRV GAG and Env (immunosuppressive domains (ISD) peptides removed) were used to perform 140 analyses per sample with PMS/ionomycin as positive and no stimulus as negative control. We found 15 GAG and 21 Env peptides that produced SFC above background levels (FIG. 6A). 59 The bar at 50 SFC demonstrates that the Gag peptides alone showed a 100% sensitivity for the PBC subjects and an 80% specificity, whereas the Env peptides demonstrated both a 100% sensitivity and specificity for activity in subjects with PBC. Individually, PBC subjects had a >800-1,800 SFC from these analyses providing a precursor frequency of 1 in 50-125 HBRV reactive T cells in the liver (FIGS. 6A and 8), whereas prior studies using PBMC showed a lower range of 1 in $10^{-3}$ to $10^{-5}$ as expected.[10] In marked contrast, cellular immune responses to PDC-E2 were only observed in one PBC subject, due to the low precursor frequency of autoreactive T cells previously reported (FIG. 8).[59]

Cellular immune responses have been found using pooled peptides of the HBRV Gag (n=58) and Env (n=85) proteins. In these studies, 40% of PBC subjects were found to make proinflammatory cellular immune responses to HBRV using FACS analyses to detect TNFa and IFNg. In order to characterize immunodominant HBRV epitopes, we screened intra-hepatic lymphocytes (IHL) from PBC subjects and control subjects for evidence of IFNg production. Methods: IHL were isolated from liver transplant recipients with PBC (n=5) and other hepatic disorders (n=4). IHL were individually stimulated with 15-mer peptides from HBRV Gag or Env proteins (n=144) or the characterized CD8+ reactive epitope to pyruvate dehydrogenase-E2 (PDH-E2). ELISpot was used to measure spot forming colonies (SFC) producing IFN-g.

15 HBRV Gag and 21 HBRV Env peptides were found to stimulate IHL. The mean number of SFC producing IFN-g stimulated with individual HBRV Gag peptides was higher in PBC subjects versus control subjects (51 vs. 10, P<0.001) and for HBRV Env peptides (72 SFC/PBC subject vs. 3 SFC/control, P<0.0001). Using a background cutoff level of 1:2,000 SFC, the individual HBRV Env peptides provided a 100% specificity and sensitivity for detecting HBRV infection in PBC subjects IHL, whereas HBRV was less discriminatory. Notably only one subject with PBC had detectable IFN-g producing IHL following stimulation with the characterized CD8+ reactive mitochondrial autoantigen PDH-E2 peptide. These are the first data to demonstrate that the intrahepatic proinflammatory cellular immune responses to HBRV greatly exceed the autoimmune response, suggesting that HBRV infection plays an important role in mediating PBC. The identified 15 HBRV Gag and 21 Env peptides can be further evaluated to measure the IFN-g release in peripheral blood mononuclear cells and construct a "Quantiferon" assay.

Example 3

Quantiferon™ assays (Qiagen) that measure IFN-γ responses to *Mycobacterium tuberculosis* (Mth) or cytomegalovirus peptides have known utility for diagnosing and monitoring disease where serological and other tests are less instructive. Because of the multiplicity of HLA haplotypes, a range of about 20-30 immunodominant viral peptides is preferably employed to create an IFN-γ release assay. The assay is performed by collecting 1 ml of blood in tubes with (i) peptides that promote a proinflammatory cognate T cell response, (ii) a negative control with no stimulant, and (iii) a positive control mitogen triggering IFN-γ production. After incubation for 16-24 hours at 37° C., 50 μL plasma is used to measure IFN-γ by ELISA. By subtracting the levels in (i) peptide tube from (ii) negative control, IFN-γ levels >0.35 IU/ml (~14 pg/ml) are considered positive for the Mtb QuantiFERON assay and the peptide tube IFN-γ levels should be 25% more than the Nil tube. This Quantiferon diagnostic will comprise of a set of human betaretrovirus peptides (~25) in a blood collection tube, accompanied by a negative control tube and a positive control tube with a PMA stimulant. After collection of blood into each tube and incubation at 37 C, the plasma will be removed and assessed for interferon-gamma production.

We tested the pool of 36 HBRV immunodominant peptides (FIG. 6) by stimulating 2×10⁶ frozen PBMC for 6 hours at 37° C. and measured IFN-γ levels in 50 μL supernatant using the Mesoscale V-Plex ELISA. This platform was chosen because of the broad linear range for measuring IFN-γ from 1,000 to below 10 pg/ml (FIG. 7B) and the validated reproducibility of IFN-γ detection. In our preliminary studies, the negative control subjects were all negative and the HBRV positive control subject with breast cancer[65] was markedly positive (FIG. 7A). All PBC subjects met the criteria of having peptide tube 25%>negative control tube but 2 subjects were borderline or negative for the criteria of the peptide tube minus negative control tube >14 pg/ml. Of interest the IFN-γ production correlated somewhat with PBC subjects' grade of disease related to ALP levels. For example, subject PBC4 with the highest values (135 pg/ml) was a First Nation subject with severe and progressive disease. Also, of note, the positive control, breast cancer subject's level was 146 pg/ml and ~15% of breast cancer subjects that we have tested demonstrate anti-HBRV Env reactivity in a similar fashion to the PBC subjects (FIG. 3).

The IFN-γ release based on the initial 36 peptides appears specific for PBC but may lack sensitivity. Analyses of the reactive peptides in FIG. 6A suggests that some were only reactive in 1 PBC subject's IHL with levels <50 SFC (such as Env 17) and optimization of the peptide pool is performed. To date, we have derived additional IHL and a second screen will be performed using all HBRV peptides individually (without ISD) on 100,000 IHL from 4 PBC and 4 donors. The IFN-γ production is evaluated by the Mesoscale ELISA rather than ELISPOT as this is more relevant to the QuantiFERON assay. Optimization of peptide pools (~25) are carried out through several iterations to formulate the IFN-γ release assay.

PBMC from 20 subjects with PBC, 20 subjects with other liver disorders and 20 healthy subjects is assessed as in FIG. 7 for the HBRV QuantiFERON assay; similar protocols and numbers of subjects are used in prior studies for establishing QuantiFERON assays (sufficient to assess the multiplicity of HLA haplotypes).[62, 66] Because HBRV has been found in subjects with AIH, cryptogenic liver disease[5] and alcoholic cirrhosis,[13] we chose other hepatic diagnoses as controls. An additional control arm with healthy subjects is used as the prevalence of HBRV infection is low in this population (~3% in middle aged females, FIG. 3). To optimize sensitivity, the cutoff is evaluated as average of background responses from the 20 healthy subjects without HBRV response using either 2+ or 3+ standard deviation, as performed for the HBRV Env ELISA (FIG. 3).

Expected Outcomes and Potential Pitfalls.

We are familiar with the procedures and will improve and optimize our peptide pool for making an IFN-γ release assay by replacing peptides with reduced IFN-γ production to increase the sensitivity while maintaining the specificity of the assay.

Figure 9:
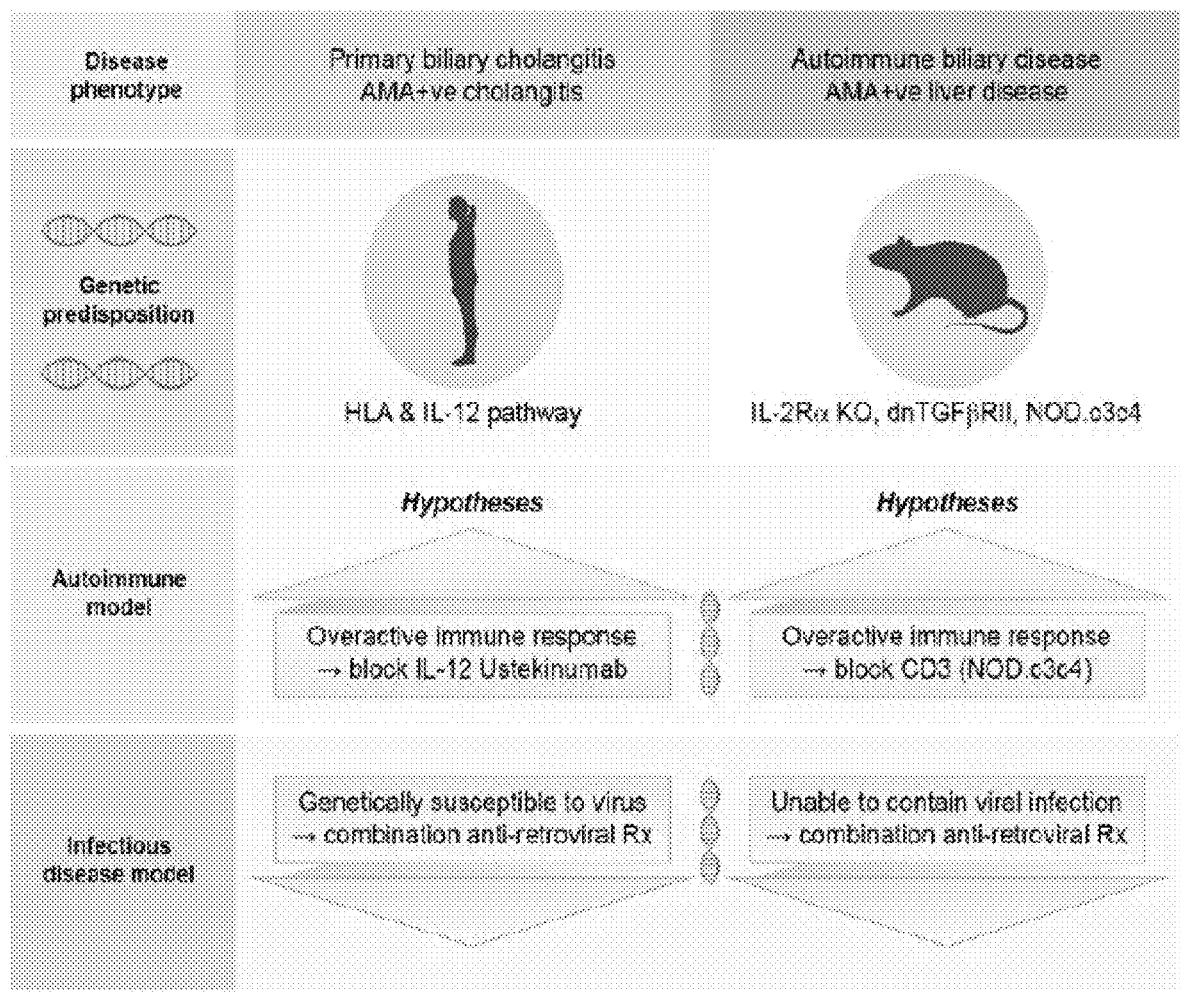

Example 4: Validation of IFN-γ Release Assay and Characterization of Cellular Immune Responses A range of subjects with and without liver disease is used to validate the IFN-γ release assay, including healthy subjects with T cell reactivity to HBRV, such PBC subject spouses and lab workers exposed to MMTV.[67] It is possible that PBC subjects produce higher levels of INF-γ with aggressive disease. Alternatively, they may have diminished IFN-γ production because of genetic predisposition (FIG. 9). In other viral diseases, for example, subjects with a remote history of acute HCV have superior memory CD8 INF-γ responses as compared to those with chronic HCV infection,[68] showing signs of T cell exhaustion.[69] Our preliminary data suggest that PBC subjects have a range of IFN-γ responses (FIG. 7) and ongoing evaluation of the cellular immune responses by other techniques are used to validate the findings from the IFN-γ release assay and further characterize HBRV immunity.

Study Design for the IFN-γRelease Assay.

1 ml blood is collected in individual heparinized tubes and tested individually with: (i) 1 μg pooled HBRV peptides, (ii) negative control, (iii) positive control with PMA and (iv) 1 μg of PDC-E2 immunodominant peptides and processed as described above and shown in FIG. 7.

Immunophenotyping HBR Reactive CD8+ Cells Using Flow Cytometry.

All our IHLs are derived from LT subjects and each of the immunodominant peptides have been liked with their respective HLA data. Using the Immune Epitope Database Analysis Resource software,[70] the thresholds for MHC class I binding predictions will be determined for the highest affinity HLA/peptide match for each sample (IC50<50 nM for high affinity).[71-76] HLA-typed tetramers will be constructed for high affinity HBRV Gag and Env peptides with high frequency class I restriction. CD8+ lymphocytes will be targeted because they provide the majority of the IFN-γ producing cells.[10] We plan to generate 10 HLA class I tetramers to evaluate the frequency of HBRV reactive CD8+ cells using a collection of common class I proteins to adequately cover the population of HLA types.[77, 78] A comparison will also be made with the HLA matched, characterized PDC-E2 CD8+ tetramer.[79] HBRV reactive CD8+ cells will be immune phenotyped for IFN-γ, TNF-α production as well as anergy/exhaustion markers, such as LAG3+, PD-1+ and BIM+.[69, 78]

Populations for Study.

For the preliminary analyses, we use 50 PBC subjects with a spectrum of progressive disease and 50 control subjects with PSC and NASH from the outsubjects. The studies are conducted in a blinded fashion to study utility of the assay linking HBRV reactivity to PBC in subjects with liver disease. Based on the current flow cytometry analyses data using HBRV GAG pools to stimulate CD8+, we use a sample size of 47 per group for a power of 0.80 with a two-sided p value of 0.05.[10] We then assess non-PBC liver disease subjects with a reported higher prevalence of HBRV target for the IFN-γ release assay (n=20 per group), including subjects with AIH, cryptogenic liver disease, HCV infection and alcoholic liver disease.[5, 13] We observed that some of our healthy controls have anti-HBRV gp52$^{SU}$ and T lymphocyte reactivity to HBRV in prior studies; these subjects are assessed using the IFN-γ release assay (n=20).

Methods.

Samples used for the IFN-γ release assay, ELISPOT and flow cytometry with HBRV and PDC-E2 tetramers. As part of the study, the magnitude of IFN-γ response to HBRV versus PDC-E2 is determined to provide a direct comparison of antiviral and autoimmune cellular proinflammatory activity (FIGS. 3 and 6). Accordingly, for both HBRV and PDC-E2, we evaluate the amount of INF-γ production, number of INF-γ producing lymphocytes, and the approximate frequency of CD8+ positive cells to each peptide and the relative state of anergy of the lymphocytes. These studies are performed using PBMC and in IHL (15 PBC subjects and 15 control LT subjects).

We have observed that all PBC LT subjects IHL have significantly higher cellular immune responses to HBRV as compared to control LT recipients (FIG. 6). Therefore, we expected to observe that a similar evaluation of PBMC will produce the same results but to a lesser degree (FIG. 7). Preliminary studies have shown that we can establish a more sensitive QuantiFERON assay because we have optimized our peptide pool and the use of whole blood provides higher levels IFN-γ production as compared to frozen PBMC. An important point established is whether PBC subjects make inadequate responses to HBRV as observed in FIG. 7, where the subject with breast cancer has the highest IFN-γ response, for example. It is possible to calculate the CD8+ IFN-γ production per lymphocyte and the state of T cell exhaustion to determine the relative activity of PBC subjects' immune response to HBRV compared to healthy individuals reactive to HBRV. IFN-γ production is evaluated with ALP and bilirubin levels to determine a relationship with disease. Our current data suggests that the anti-HBRV pro-inflammatory responses will surpass the autoimmune responses based on our flow cytometry and ELISPOT analyses, which we believe is an important finding.[59] The comparative analyses using confirmatory ELISPOT and flow cytometry provides insight into the relative contribution of the autoimmune response vs. anti-HBRV activity. The validation process also provides insight into the hepatotropic nature of HBRV and the possible contribution of viral infection in other disease processes such as AIH and other hepatic disorders.

Example 5

Subjects with Primary Biliary Cholangitis (PBC) Make Proinflammatory Cellular Immune Responses to Human Betaretrovirus Our laboratory is characterizing a human betaretrovirus (HBRV) infection in subjects with PBC. Most subjects have evidence of HBRV proviral integrations in their bile ducts and respond to anti-retroviral therapy. Peripheral blood, PCR and serological diagnostics are only capable of detecting HBRV infection in a minority of PBC subjects. FACS analyses has shown that PBC subjects mount pro-inflammatory T cell responses.

QuantiFERON (QF) assays are used to determine T lymphocyte γ-interferon (IFN) responses in subjects with mTB or CMV where humoral responses to infection are either absent or not helpful for diagnosis. Commercial γ-IFN release assays have a high positive predictive value for detecting ongoing T lymphocyte responses to ongoing infections. We plan to create new diagnostic assay to detect HBRV infection in PBC subjects and assess on activity of disease. Our second objective is to compare the γ-IFN release HBRV peptides to the characterized mitochondrial PDH complex E2 peptides.

Referring to FIG. 8, depending on stage of disease, subjects with PBC displayed a precursor frequency of $10^{-7}$ to $10^{-8}$ PBMC reactive to the characterized PDH-E2 peptide and $\sim 2 \times 10^{-5}$ within the IHL [data based on Table 1, ref. note that future epitope studies amplified cognate T cells in vitro to inflate the number of PDH-E2 reactive lymphocytes. Referring to FIG. 8B, in contrast, subjects with chronic HCV infection have a far higher proportion of lymphocyte reactive to HCV epitopes with a range of $2 \times 10^{-5}$ to $1.3 \times 10^{-3}$ in PBMC and a 30 fold enrichment of IHL reactive to HCV epitopes. Referring to FIG. 8C, subjects with PBC also have a higher frequency of lymphocytes reactive to HBRV in both PBMC and IHL as compared to the autoreactive T cell to PDH-E2.

Figure 6B:
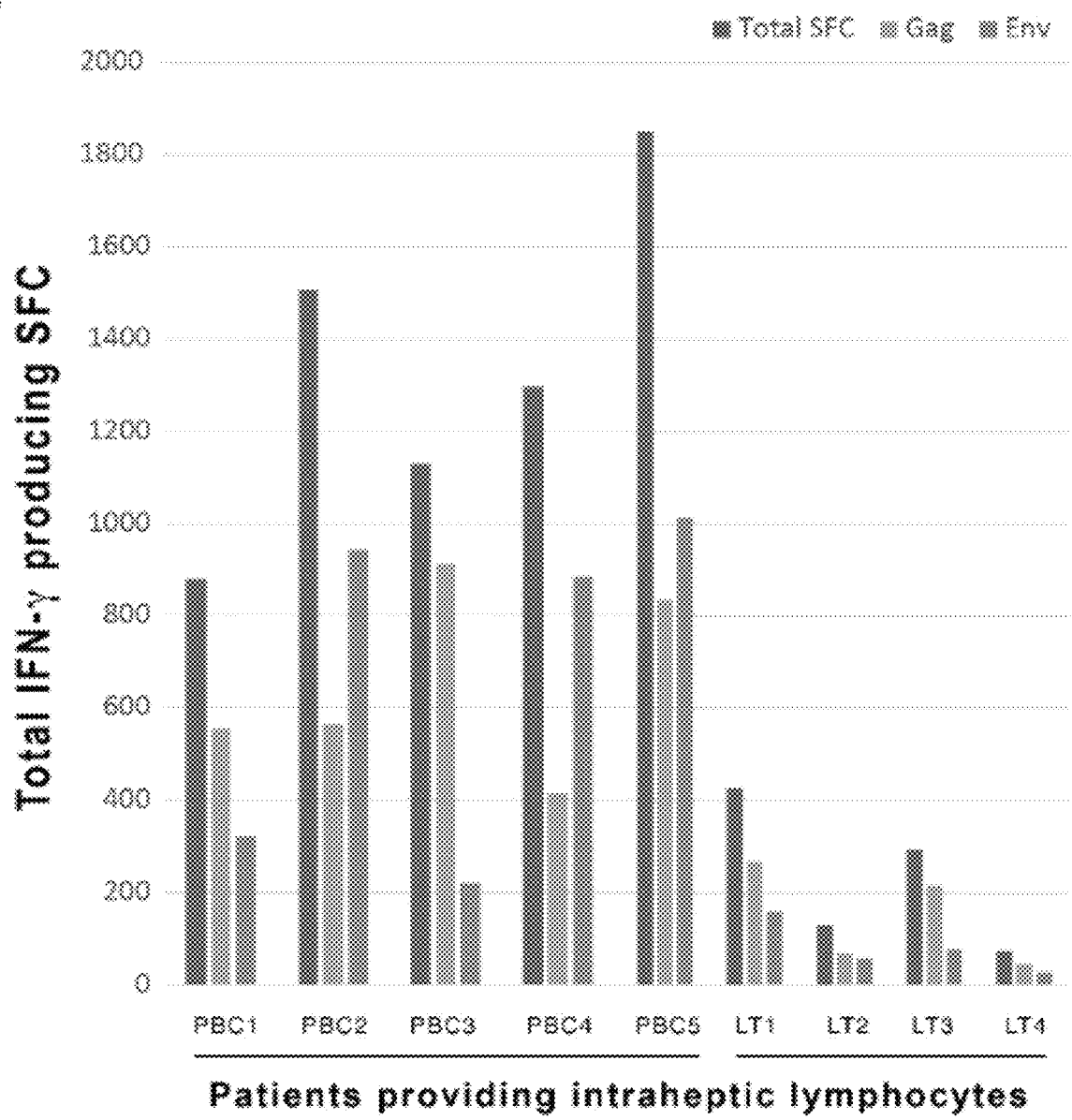
Figure 10A:
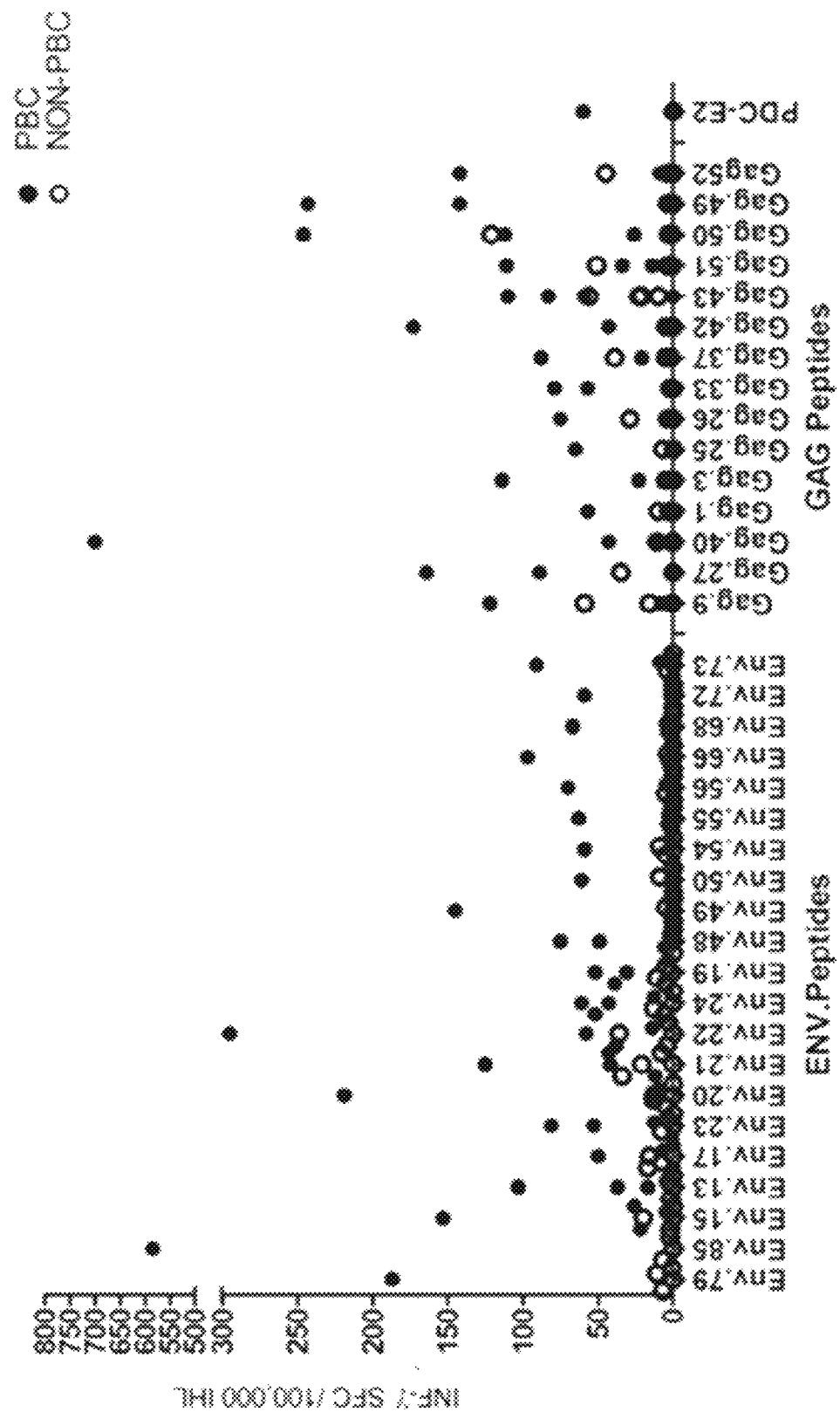
Figure 10B:
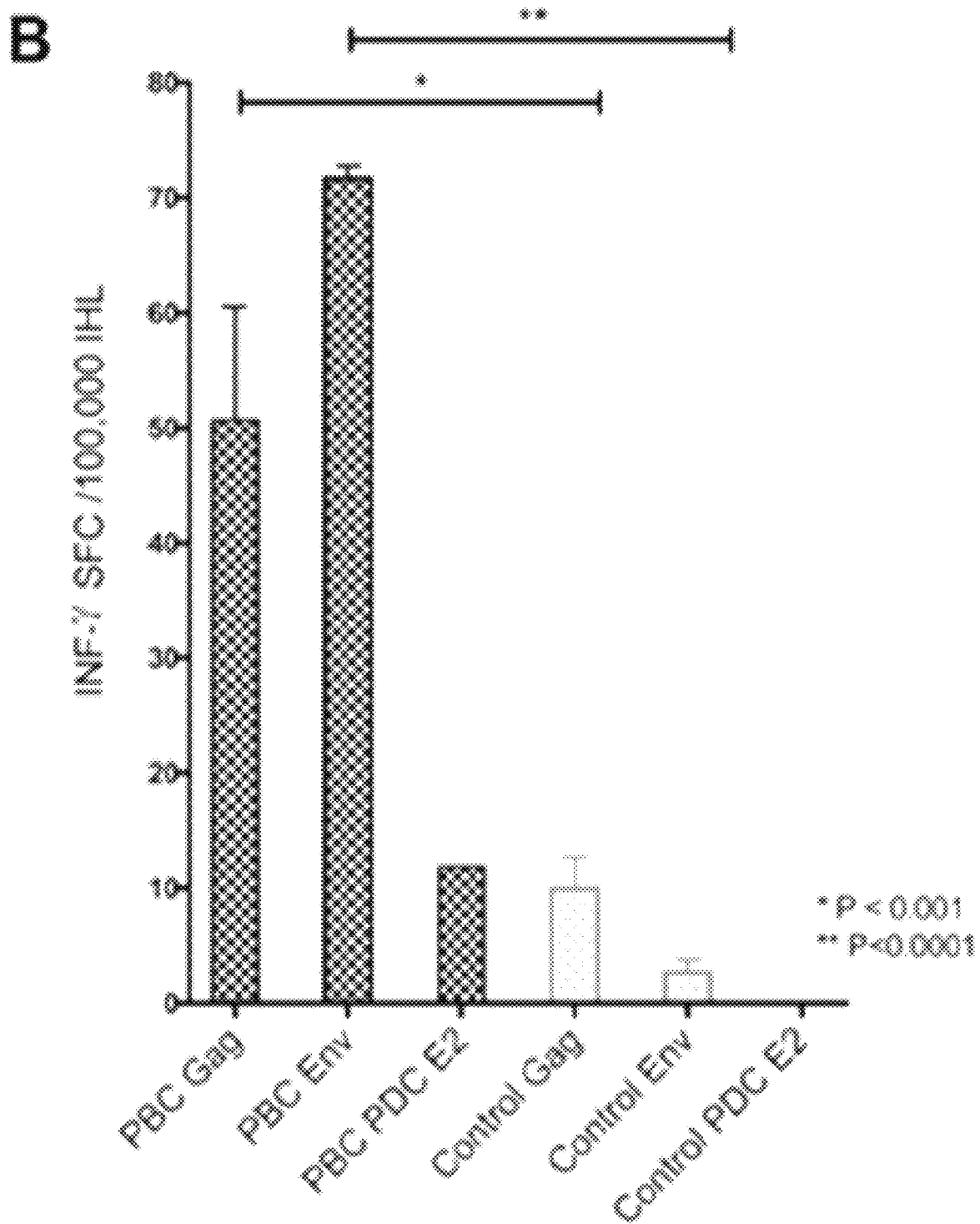

Referring to FIGS. 10A and 10B, the analyses using 144 peptides identified 15 HBRV Gag and 21 HBRV Env peptides that stimulated the PBC subjects' IHL (FIG. 6B, 10B). The mean number of IFN-γ producing SFC stimulated with individual peptides was 51 PBC versus 10 controls for HBRV Gag and 72 PBC versus 3 controls for HBRV Env (FIG. 10B: P<0.001 and P<0.0001, respectively). Using a mean cutoff level <5 SFC, the HBRV Env peptides provided a 100% specificity and sensitivity for detecting HBRV infection, whereas HBRV was less discriminatory. Notably only one subject with PBC had detectable IFN-γ producing IHL following stimulation with the autoantigen mitochondrial autoantigen PDH-E2 peptide.

These are the first data to demonstrate that the intrahepatic proinflammatory cellular immune responses to HBRV greatly exceed the autoimmune response, suggesting that HBRV infection plays an important role in mediating PBC. The identified 15 HBRV Gag and 21 Env peptides are being evaluated using peripheral blood mononuclear cells to measure the IFN-γ release and construct a "Quantiferon" assay.

Example 6 cART Therapy

Ursodeoxycholic acid (UDCA) is often considered the standard of care for PBC treatment and acts as a choleretic agent to ameliorate the toxic effects of bile within the liver. More recently obeticholic acid (OCA), a potent FXR agonist, has been licensed for PBC subjects following demonstration that 46% of subjects unresponsive to UDCA achieved the composite endpoints of improved hepatic biochemistry. Combination anti-retroviral therapy (cART) may also provide potential adjunctive therapy to UDCA nonresponders. A recent randomized controlled trial was terminated early due to poor tolerability of lopinavir-ritonavir. Those able to tolerate cART, however, developed marked improvement in hepatic biochemistry and HBRV levels in the open label extension study.

Figure 1B:
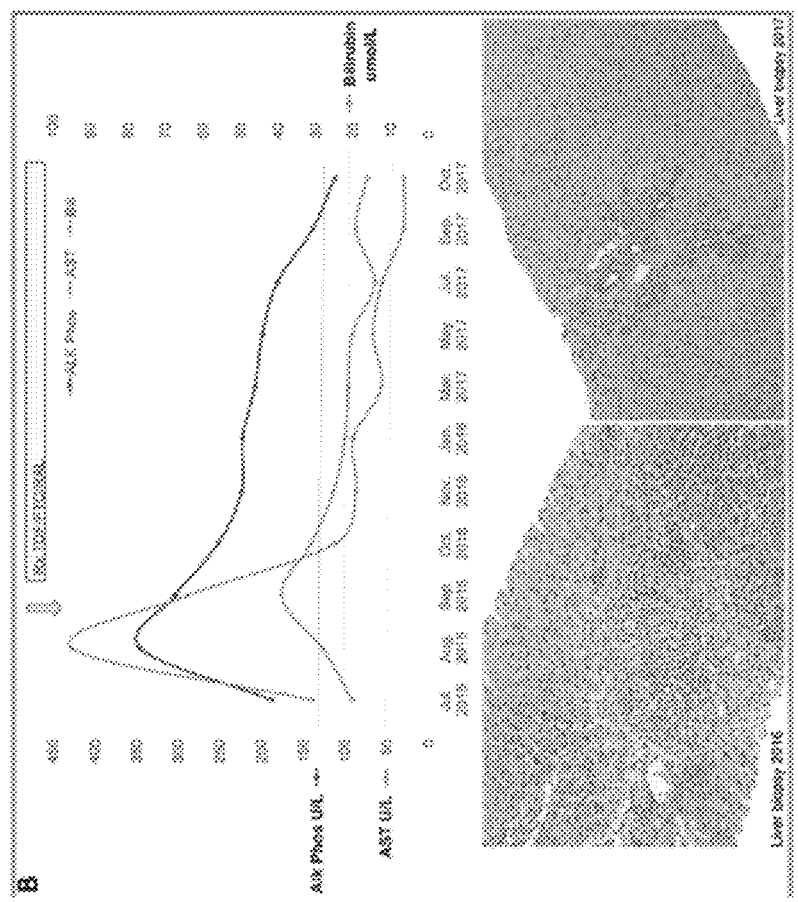

Referring to FIGS. 1A and 12, after commencing combination treatment of tenofovir (TDF)/emtricitabine (FTC)/a protease inhibitor lopinavir boosted with ritonavir (LPRr), the subject experienced increased ALP (left Y axis), bilirubin and a near doubling in ALT coinciding with increased proviral HBRV in the peripheral blood by 3 months (all right Y axis). After 12 months, she experienced a decline in all liver tests that subsequently normalized with further reduction of HBRV levels to below the established cut off level by 24 months of treatment, Marked improvement in cholangitis was observed by liver biopsy. Referring to FIG. 1B, this LT recipient developed severe recurrent PBC unresponsive to UDCA and changes in immunosuppression. Following 6 months' TDF/FTC/raltregravir (RAL) she experienced a marked reduction in hepatic biochemistry which normalized by 12 months with clear histological improvement. We therefore demonstrated marked reduction in hepatic biochemistry and HBRV with histological improvement following a randomized controlled trials using combination antiretroviral therapy.

ELISA Studies

Figure 2:
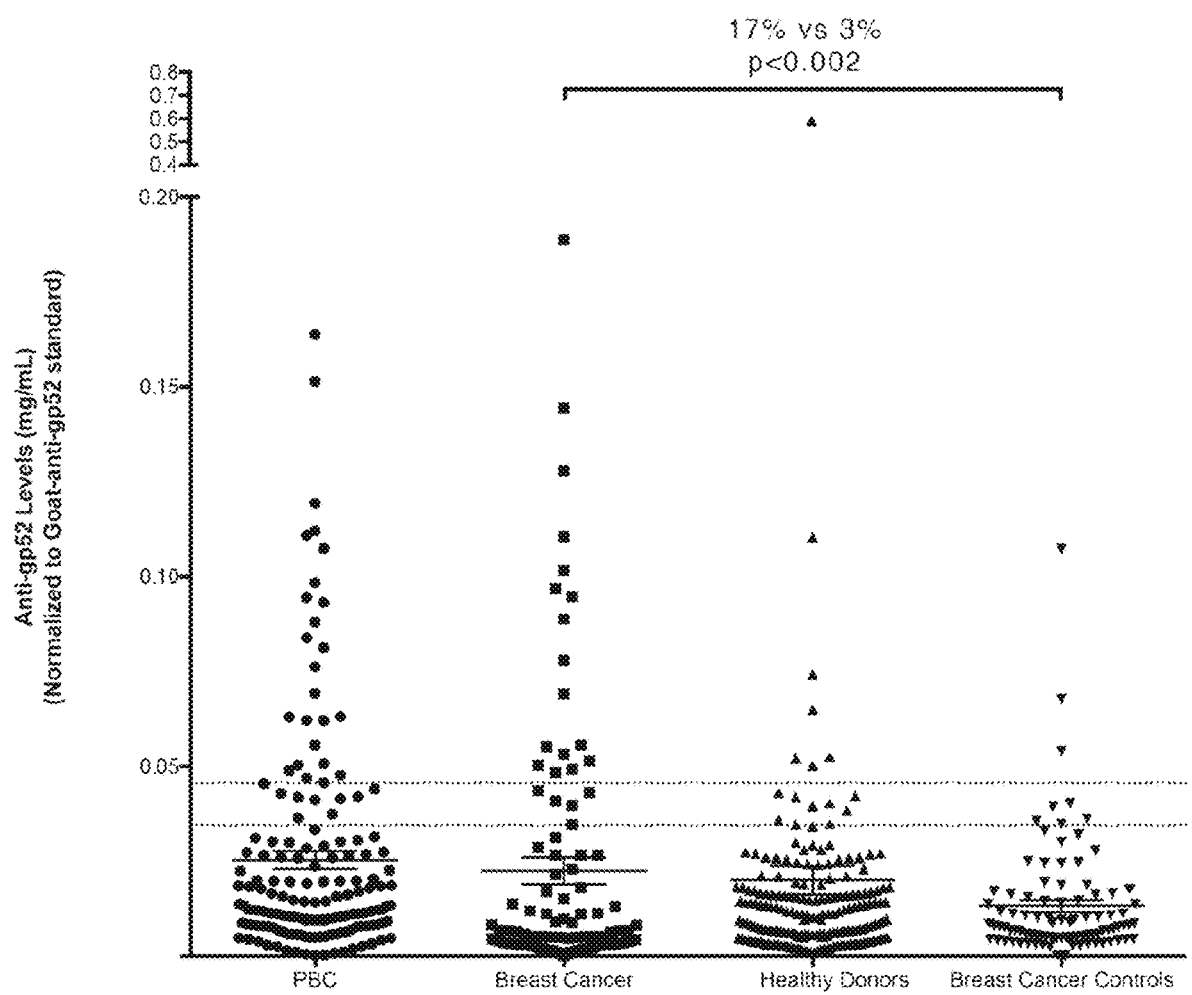
FIG. 2 depicts HBRV Env seroprevalence in subjects with PBC and age matched control healthy females (also see FIG. 16).

While initial Western blot studies showed PBC subjects reactivity to HBRV Env,[37] we subsequently established a diagnostic HBRV Env gp52 ELISA and found only 15% of PBC subjects had demonstrable Env gp52 antibodies (FIG. 2) and HBRV Gag proteins also lacked diagnostic utility for clinical studies. The limited humoral immune responses is consistent with the natural biology of MMTV, where infection though the oral route is associated with tolerization in mice.[38] Neutralizing antibody production is only associated with robust interferon (IFN)-γ responses in mice,[39] in keeping with our hypothesis that PBC subjects make limited immune responses to HBRV.

Referring to FIG. 3, ELISA studies were conducted using recombinant HBRV gp52 Env expressed in HEK 293 cells. The sero-prevalence was 15% in PBC subjects versus 3% age/sex matched controls (p<0.002). The two dotted lines shown represent the median of background+2×SD of the signal and +3×SD respectively, with the latter cutoff used for the ELISA.

All references are herein incorporated by reference.

TABLE 1

Sequences for SEQ ID Nos: 1-146

| SEQ ID NO. | | Amino acid sequence |
|---|---|---|
| 1 | Gag 9 | YPIWLQLREILTEQSDLVLL |
| 2 | Gag 27 | EKGDLTFTFPVVFMGESDDD |
| 3 | Gag 40 | LKDVTTNAVLAWRAIPPPGV |
| 4 | Gag 1 | MGVSGSKGQKLFVSVLQRLL |
| 5 | Gag 3 | SERGLHVKESSAIEFYQFLI |
| 6 | Gag 25 | ALRRKPLPPVGFAGAMAEAR |
| 7 | Gag 26 | GFAGAMAEAREKGDLTFTFP |
| 8 | Gag 33 | WLTPSDWHQTARATLSPGDY |
| 9 | Gag 37 | KRKGKVSLDMLLGTGQFLSP |
| 10 | Gag 42 | KKTVLAGLKQGNEESYETFI |
| 11 | Gag 43 | GNEESYETFISRLEEAVYRM |
| 12 | Gag 51 | RGQKYSTLVKQTYGGGKGGQ |
| 13 | Gag 50 | VQGMAYAAAMRGQKYSTLVK |
| 14 | Gag 49 | RACLDASPAVVQGMAYAAAM |
| 15 | Gag 52 | QTYGGGKGGQGSEGPVCFSC |
| 16 | Env 79 | FIFIGVGALLLVIVLMIF |
| 17 | Env 85 | GNAAPAAEMYELPRVSYT |
| 18 | Env 15 | PVGWGNTDPIRVLTNQTI |
| 19 | Env 13 | TGESYWAYLPKPSILHPV |
| 20 | Env 17 | TIYLGGSPDFHGFRNMSG |
| 21 | Env 23 | QVFLSDTPTVDNNKPGGK |
| 22 | Env 20 | KSDTLPICFSLSFSTPTG |
| 23 | Env 21 | FSLSFSTPTGCFQVDKQV |
| 24 | Env 22 | TGCFQVDKQVFLSDTPTV |
| 25 | Env 24 | TVDNNKPGGKGDKRRMWE |
| 26 | Env 19 | SGNVHFEGKSDTLPICFS |
| 27 | Env 48 | ILLGLPQLIDIEKRGSTF |
| 28 | Env 49 | IDIEKRGSTFHISCSSCR |
| 29 | Env 50 | TFHISCSSCRLTNCLDSS |
| 30 | Env 54 | VLLPVDIGDEPWFDDSAI |
| 31 | Env 55 | DEPWFDDSAILTFRYATD |
| 32 | Env 56 | AILTFRYATDLIRAKRFV |
| 33 | Env 66 | EGVVLELGQDEANLKTRM |

TABLE 1-continued

Sequences for SEQ ID Nos: 1-146

| SEQ ID NO. | | Amino acid sequence |
|---|---|---|
| 34 | Env 68 | RMSTRCHANYDFICVTPL |
| 35 | Env 72 | LLGIWNDNEISYNIQELA |
| 36 | Env 73 | EISYNIQELANLISDMSK |
| 37 | Gag 2 | LFVSVLQRLLSERGLHVKES |
| 38 | Gag 4 | SAIEFYQFLIKVSPWFPEEG |
| 39 | Gag 5 | KVSPWFPEEGGLNLQDWKRV |
| 40 | Gag 6 | GLNLQDWKRVGREMKRYAAE |
| 41 | Gag 7 | GREMKRYAAEHGTDSIPKQA |
| 42 | Gag 8 | HGTDSIPKQAYPIWLQLREI |
| 43 | Gag 10 | LTEQSDLVLLSAEAKSVTEE |
| 44 | Gag 11 | SAEAKSVTEEELEEGLTGLL |
| 45 | Gag 12 | ELEEGLTGLLSTSSQEKTYG |
| 46 | Gag 13 | STSSQEKTYGTRGTAYAEID |
| 47 | Gag 14 | TRGTAYAEIDTEVDKLSEHI |
| 48 | Gag 15 | TEVDKLSEHIYDEPYEEKEK |
| 49 | Gag 16 | YDEPYEEKEKADKNEEKDHV |
| 50 | Gag 17 | ADKNEEKDHVRKVKKVVQRK |
| 51 | Gag 18 | RKVKKVVQRKEISEGKRKEK |
| 52 | Gag 19 | EISEGKRKEKDQKAFLATDW |
| 53 | Gag 20 | DQKAFLATDWNDDDLSPEDW |
| 54 | Gag 21 | NDDDLSPEDWDDLEEQAAHY |
| 55 | Gag 22 | DDLEEQAAHYHDDDELILPV |
| 56 | Gap 23 | HDDDELILPVKRKVVKKKPQ |
| 57 | Gag 24 | KRKVVKKKPQALRRKPLPPV |
| 58 | Gag 28 | VVFMGESDDDDTPVWEPLPL |
| 59 | Gag 29 | DTPVWEPLPLKTLKELQLAV |
| 60 | Gag 30 | KTLKELQLAVKTMGPSAPYT |
| 61 | Gap 31 | KTMGPSAPYTLQVVDMVASQ |
| 62 | Gag 32 | LQVVDMVASQWLTPSDWHQT |
| 63 | Gag 34 | ARATLSPGDYVLWRTEYEEK |
| 64 | Gag 35 | VLWRTEYEEKSKETVQKAAG |
| 65 | Gag 36 | SKETVQKAAGKRKGKVSLDM |
| 66 | Gag 38 | LLGTGQFLSPSSQIKLSKDV |
| 67 | Gag 39 | SSQIKLSKDVLKDVTTNAVL |
| 68 | Gag 41 | AWRAIPPPGVKKTVLAGLKQ |
| 69 | Gag 44 | SRLEEAVYRMMPRGEGSDIL |
| 70 | Gag 45 | MPRGEGSDILIKQLAWENAN |
| 71 | Gag 46 | IKQLAWENANSLCQDLIRPI |

TABLE 1-continued Sequences for SEQ ID Nos: 1-146

| SEQ ID NO. | | Amino acid sequence |
|---|---|---|
| 72 | Gag 47 | SLCQDLIRPIRKTGTIQDYI |
| 73 | Gag 48 | RKTGTIQDYIRACLDASPAV |
| 74 | Gag 53 | GSEGPVCFSCGKTGHIKKDC |
| 75 | Gag 54 | GKTGHIKKDCKEEKGSKRAP |
| 76 | Gag 55 | KEEKGSKRAPSGLCPRCKKG |
| 77 | Gag 56 | SGLCPRCKKGYHWKSECKSK |
| 78 | Gag 57 | YHWKSECKSKFDKDGNPLPP |
| 79 | Gag 58 | DKDGNPLPPLETNTENSKNL |
| 80 | Env 1 | MPNHQSGSPTGSSDLLLS |
| 81 | Env 2 | PTGSSDLLLSGKKQRPHL |
| 82 | Env 3 | LSGKKQRPHLALRRKRRR |
| 83 | Env 4 | HLALRRKRRREMRKINRK |
| 84 | Env 5 | RREMRKINRKVRRMNLAP |
| 85 | Env 6 | RKVRRMNLAPIKEKTAWQ |
| 86 | Env 7 | APIKEKTAWQHLQALIFE |
| 87 | Env 8 | WQHLQALIFEAEEVLKTS |
| 88 | Env 9 | FEAEEVLKTSQTPQTSLT |
| 89 | Env 10 | TSQTPQTSLTLFLTLLSV |
| 90 | Env 11 | LTLFLTLLSVLGPPPVTG |
| 91 | Env 12 | SVLGPPPVTGESYWAYLP |
| 92 | Env 14 | LPKPSILHPVGWGNTDPI |
| 93 | Env 16 | PIRVLTNQTIYLGGSPDF |
| 94 | Env 18 | DFHGFRNMSGNVHFEGKS |
| 95 | Env 25 | GKGDKRRMWELWLTTLGN |
| 96 | Env 26 | WELWLTTLGNSGANTKLV |
| 97 | Env 27 | GNSGANTKLVPIKKKLPP |
| 98 | Env 28 | LVPIKKKLPPKYPHCQIA |
| 99 | Env 29 | PPKYPHCQIAFKKDAFWE |
| 100 | Env 29 | PPKYPHCQIAFKKDAFWE |
| 101 | Env 30 | IAFKKDAFWEGDESAPPR |
| 102 | Env 31 | WEGDESAPPRWLPCAFPD |
| 103 | Env 32 | PRWLPCAFPDQGVSFSPK |
| 104 | Env 33 | PDQGVSFSPKGTLGLEWD |
| 105 | Env 34 | PKGTLGLLWDFSLPSPSV |
| 106 | Env 35 | WDFSLPSPSVDQSDQIKS |
| 107 | Env 36 | SVDQSDQIKSKKDLFGNY |
| 108 | Env 37 | KSKKDLFGNYTPPVNKEV |
| 109 | Env 38 | NYTPPVNKEVHRWYEAGW |
| 110 | Env 39 | EVHRWYEAGWVEPTWFWE |
| 111 | Env 39 | EVHRWYEAGWVEPTWFWE |
| 112 | Env 40 | GWVEPTWFWENSPKDPND |
| 113 | Env 41 | WENSPKDPNDRDFTALVP |
| 114 | Env 42 | NDRDFTALVPHTELFRLV |
| 115 | Env 43 | VPHTELFRLVAASRYLIL |
| 116 | Env 44 | LVAASRYLILKRPGFQEH |
| 117 | Env 45 | ILKRPGFQEHDMIPTSAC |
| 118 | Env 46 | EHDMIPTSACATYPYAIL |
| 119 | Env 47 | ACATYPYAILLGLPQLID |
| 120 | Env 51 | CRLTNCLDSSAYDYAAII |
| 121 | Env 52 | SSAYDYAAIIVKRPPYVL |
| 122 | Env 52 | SSAYDYAAIIVKRPPYVL |
| 123 | Env 53 | IIVKRPPYVLLPVDIGDE |
| 124 | Env 57 | TDLIRAKRFVAAIILGIS |
| 125 | Env 58 | FVAAIILGISALIAIITS |
| 126 | Env 59 | ISALIAIITSFAVATTAL |
| 127 | Env 60 | TSFAVATTALVKEMQTAT |
| 128 | Env 61 | ALVKEMQTATFVNNLHRN |
| 129 | Env 62 | ATFVNNLHRNVTLALSEQ |
| 130 | Env 63 | RNVTLALSEQRIIDLKLE |
| 131 | Env 64 | EQRIIDLKLEARLNALEG |
| 132 | Env 65 | LEARLNALEGVVLELGQD |
| 133 | Env 67 | QDEANLKTRMSTRCHANY |
| 134 | Env 69 | NYDFICVTPLPYNASESW |
| 135 | Env 70 | PLPYNASESWERTKAHLL |
| 136 | Env 71 | SWERTKAHLLGIWNDNEI |
| 137 | Env 74 | LANLISDMSKQHIDTVDL |
| 138 | Env 75 | SKQHIDTVDLSGLAQSFA |
| 139 | Env 76 | DLSGLAQSFANGVKALNP |
| 140 | Env 77 | FANGVKALNPLDWTQYFI |
| 141 | Env 78 | NPLDWTQYFIFIGVGALL |
| 142 | Env 80 | LLLVIVLMIFPIVFQCLA |
| 143 | Env 81 | IFPIVFQCLAKSLDQVQS |
| 144 | Env 82 | LAKSLDQVQSDLNVLLLK |
| 145 | Env 83 | QSDLNVLLLKKKKGGNAA |
| 146 | Env 84 | LKKKKGGNAAPAAEMVEL |

Example 7—Seroprevalence of Human Betaretrovirus Surface Protein Antibodies in Patients with Breast Cancer and Liver Disease Mouse mammary tumor virus (MMTV) is a betaretrovirus that plays a causal role in the development of breast cancer and lymphoma in mice. Closely related sequences that share 91-99%/o nucleotide identity with MMTV have been repeatedly found in humans with neoplastic and inflammatory diseases. Evidence for infection with a betaretrovirus has been found in patients with breast cancer and primary biliary cholangitis and referred to as the Human Mammary Tumor Virus and the Human Betaretrovirus (HBRV), respectively. Using the gold standard technique of demonstrating retroviral infection, HBRV proviral integrations have been detected in cholangiocytes, lymph nodes and liver of patients with primary biliary cholangitis. However, the scientific biomedical community has been reluctant to embrace the hypothesis that MMTV like betaretroviruses may infect humans because reports of viral detection have been inconsistent and robust diagnostic assays have been lacking. Specifically, prior serological assays using MMTV proteins have produced divergent results in human disease.

Accordingly, in the following studies, a partial HBRV Surface (Su) construct was transfected into HEK293 to create an ELISA assay. The secreted HBRV gp52 Su protein was then used to screen for serological responses in patients with breast cancer and liver disease. A greater proportion of breast cancer patients (n=98) were found to have serological reactivity to HBRV Su as compared to age and sex matched control subjects (10.2% versus 2.0%, P=0.017, OR=5.6 [1.25-26.3]). Similarly, the frequency of HBRV Su reactivity was higher in patients with primary biliary cholangitis (n=156) as compared to blood donors (11.5% vs. 3.1%, P=0.0024, OR=4.09 [1.66-10.1]). While the sensitivity of the HBRV Su ELISA was somewhat limited under the conditions used, the assay was highly specific for serologic detection in patients with breast cancer or primary biliary cholangitis, respectively (98.0% [93.1%-99.7%] and 97.0% [93.4%-98.6%]).

Breast cancer is the most frequent cancer diagnosis among females and a leading cause of cancer deaths worldwide [1, 2]. Several viruses have been linked with the development of human breast cancer but none have been established as having a causal etiology [3, 4]. One such agent resembles mouse mammary tumor virus (MMTV), a murine betaretrovirus that plays a direct role in the development of breast cancer in mice [5]. Indeed, cloned betaretrovirus nucleotide sequences from humans reportedly share between 91% to 99% identity with various regions of the MMTV genome [6-9]. However, diagnostic assays are lacking to reproducibly detect betaretrovirus infection in humans [10].

MMTV does not encode an oncogene but rather activates growth pathways by insertional mutagenesis to promote carcinogenesis in mice [11]. The diagnosis of MMTV infection in mice can be challenging. The viral burden is below the limits of detection in blood and the agent is encoded as an endogenous retrovirus in most mice, therefore, exogenous viral genomic nucleic acid sequences cannot easily be distinguished from endogenous expression of MMTV [12]. Furthermore, inadequate humoral responses are made by weanling pups infected via ingestion of MMTV in milk due to the tolerizing effects of neonatal infection by the oral route [13]. Accordingly, a diagnosis of MMTV infection is made by assessing skewing of T cell receptor V-β subsets to demonstrate the MMTV superantigen effect [14].

Evidence for human infection first surfaced in 1971, when B-type particles resembling MMTV were observed by electron microscopy in the milk of breast cancer patients [15]. Breast cancer patients were also reported to harbor betaretrovirus nucleic acid sequences and/or proteins in various samples, including milk [16], serum [17], salivary glands [18], as well as breast cancer tissue [19], cyst fluid [20], and breast cancer cells in culture [21, 22]. Thereafter, betaretrovirus sequences resembling MMTV were PCR-cloned from breast cancer tissues derived from various countries and the agent was referred to as the human mammary tumor virus [7, 23-27].

In 2003, a human betaretrovirus (HBRV) was characterized in patients with primary biliary cholangitis (PBC; previously known as primary biliary cirrhosis [28]), an inflammatory autoimmune liver disease. The agent was predominantly detected in perihepatic lymph nodes and was shown to promote the expression of mitochondrial autoantigens in co-cultivation studies with cholangiocytes, a well characterized PBC disease specific phenotype [9, 29]. Evidence of human betaretrovirus proviral integrations was subsequently demonstrated in PBC patients by ligation mediated PCR and Illumina sequencing, using a bioinformatics pipeline that ensured the exclusion of all sequences potentially related to murine or HERV sequences. More than 2,200 unique HBRV integrations were identified, and the majority of PBC patients were found to have evidence of proviral integrations linked with HBRV RNA production in cholangiocytes [30]. In clinical trials, PBC patients on combination anti-retroviral therapy have shown biochemical and histological improvement with therapy [31-34].

The hypothesis that a betaretrovirus may be linked with human breast cancer has gained little traction over the years because of the inconsistency of findings in different reports, a concern for cross-reactivity with human endogenous retroviruses (HERV) and the low level of viral burden [10, 35, 36]. With regard to the potential for a link with betaretrovirus infection and PBC, investigators have either been unable to detect viral infection [37] or to confirm the specificity of HBRV infection in PBC patients [38]. Furthermore, previous serological studies using MMTV preparations as substrate have been unable to demonstrate specific antibody reactivity to defined MMTV proteins [37, 39]. While HBRV shares between a 93% to 97% amino acid identity with the MMTV Envelope protein, consistent differences have been observed between HBRV Env compared to MMTV Env that may alter antigenicity [6]. In the present study, we expressed the HBRV gp52 Surface (Su) protein in human cells to create an enzyme linked immunosorbent assay (ELISA). In this example, we report the seroprevalence of anti-HBRV gp52 Su reactivity in patients with breast cancer, liver disease and healthy subjects.

Materials and Methods

Patient Samples

A serum panel of breast cancer patients (n=98) and age/sex match controls (n=102) was obtained from the Alberta's Tomorrow Project; a longitudinal study tracking 55,000 adults in Alberta [40]. Liver disease patient serum was prospectively collected from the hepatology outpatients at the Zeidler Clinic, University of Alberta Hospital from January 2003 to December 2014. Serum from 156 patients with PBC, 46 with primary sclerosing cholangitis (PSC), 16 with autoimmune hepatitis (AIH), 25 with non-alcoholic fatty liver disease (steatosis), 8 with alcoholic liver disease (ALD), 19 with viral hepatitis, 6 with cryptogenic liver disease and 19 with miscellaneous liver disease. Healthy blood donors' serum samples (n=194) were provided by the Department of Transfusion Medicine, National Institute of Health, Bethesda, Md.

Recombinant DNA Expression Constructs

The HBRV Su was derived from HBRV sequences obtained from a PBC patients' perihepatic lymph node [6]. The HBRV Su coding sequence was cloned into pcDNA3.1 (Invitrogen) vector along with a TAP tag at the 3' terminus of the HBRV Su [41] and 4 copies of M-PMV cytoplasmic transport element (CTE) downstream [42].

HBRV Su Expression Construct:

The pHBRV Su-TAP expression construct was made with the TAP tag located at the 3' terminus of the HBRV Su. The TAP, HBRV Signal peptide and Su coding region (1362 bp) were PCR-amplified with primer pairs SuFW/SuRV and TapFW/TapRV (Table A) using HiF Taq polymerase (Invitrogen). The amplified fragments were digested with NheI/KpnI and KpnI/BamHI and cloned into pcdna3.1 (Invitrogen). To generate pHBRV-SU-TAP-4CFW and pHBRV-SU-TAP-4CRV, and the CTE sequence was excised from pGAG-GFP-CET with XbaI and inserted into the corresponding site of pHBRV Su-TAP. To create pHBRV Su-TAP-4C FW-puromycin, the puromycin open reading frame was amplified from pCMV-MMTV-puri [Zhang, G., et al., *Pericentriolar Targeting of the Mouse Mammary Tumor Virus GAG Protein*. PLoS One, 2015. 10(6): p. e0131515] with primer pair puriFW/puriRV and inserted into the Sma1/BstBI sites of pHBRV Su-TAP-4C. All the constructs were verified by sequencing.

TABLE A

Primer sequences used for construction of the expression plasmids

| Primer | Primer sequence (5' to 3')* | Restriction enzyme |
|---|---|---|
| SuFW | GTTG<u>GCTAGC</u>ATGCCGAATCACCAATCTG GGTCC (SEQ ID NO: 149) | NheI |
| SuRV | TCGA<u>GGTACC</u>GGCTCGAATTAAATCTGTG GCAT (SEQ ID NO: 150) | KpnI |
| TapFW | ATGC<u>GGTACC</u>CTGGTGCCGCGCGGCAGCG (SEQ ID NO: 151) | KpnI |
| TapRV | CTCC<u>GGATCC</u>TTAATGGTGATGGTGATGA TGCC (SEQ ID NO: 152) | BamHI |
| PuriFW | GATCGATAT<u>CCCGGG</u>ATGGCCACCGAGTA CAAGCCCAC (SEQ ID NO: 153) | SmaI |
| PuriRV | GATC<u>TTCGAA</u>TCAGGCACCGGGCTTGCGG GTC (SEQ ID NO: 154) | BstBI |

*Introduced restriction sites are underlined

HBRV Envelope Coding Sequence (1362 bp, Primers Underlined):

The HBRV Su was constructed from Human betaretrovirus isolates AF513920, AF513921 and AY326252 [Xu. L., et al., *Cloning the human betaretrovirus proviral genome from patients with primary biliary cirrhosis*. Hepatology, 2004. 39(1): p. 151-6].

(SEQ ID NO: 148)

atgccgaatcaccaatctgggtccccgaccggttcatccgacctttta ctgagcggaaagaagcaacgcccacacctggcactgcggagaaaacgc -continued cgcagcgagatgagaaagatcaacaggaaagtccggaggatgaatcta gcccccatcaaagagaagacggcttggcaacatctgcaggcgttaatc ttcgaagcggaggaggttcttaaaacctcacaaactccccaaacctct ttgactttatttcttgctttgttgtctgtcctcggcccccgcctgtg accggggaaagttattgggcttacctacctaaaccacctattctccat cccgtgggatggggaaatacagaccccattagagttctgaccaatcaa accatatatttgggtgggtcacctgactttcacgggtttagaaacatg tctggcaatgtacattttgaggggaagtctgatacgctccccatttgc ttttccttctccttttctacccccacaggctgatttcaagtagataag caagtatttctttctgatacacccgcggttgataataataaacctggg ggaaagggtgataaaaggcgtatgtgggaactttggttgactactttg gggaactcaggggccaatacaaaactggtccctataaaaaagaagttg ccccccaaatatcctcactgccagatcgcctttaagaaggacgccttc tgggagggagacgagtctgctcctccacggtggttgccttgcgccttc cctgaccagggggtgagtttttctccaaaagggacccttgggttactt tgggatttctcccttccctcgcctagtgtagatcagtcagatcagatt agaagcaaaaaggatctatttggaaattatactcccccctgtcaataaa gaggttcatcgatggtatgaagcaggatgggtagaacgtacatggttc tgggaaaattctcctaaggatcccaatgatagagattttactgctcta gttccccatacagaattgtttcgcttagttgcagcctcaagatatctt attctcaaaaggccaggatttcaagaacatgacatgattcctacatct gcctgtgctacttacccttatgccatattattaggattacctcagcta atagatatagagaaaagaggatctacttttcatatttcctgttcttct tgtagattgactaattgtttagattcttctgcctacgactatgcagcg atcatagtcaagaggccgccatacgtgctgctacctgtagatattggt gatgaaccatggtttgatgattctgccattctaacctttaggtatgcc acagatttaattcgagcc Protein Sequence:

(SEQ ID NO: 147)

MPNHQSGSPTGSSDLLLSGKKQRPHLALRRKRRSEMRKINRKVRRMNL

APIKEKTAWQHLQALIFEAEEVLKTSQTPQTSLTLFLALLSVLGPPPV

TGESYWAYLPKPPILHPVGWGNTDPIRVLTNQTIYLGGSPDFHGFRNM

SGNVHFEGKSDTLPICFSFSFSTPTGCFQVDKQVFLSDTPAVDNNKPG

GKGDKRRMWELWLTTLGNSGANTKLVPIKKKLPPKYPHCQIAFKKDAF

WEGDESAPPRWLPCAFPDQGVSFSPKGTLGLLWDFSLPSPSVDQSDQI

RSKKDLFGNYTPPVNKEVHRWYEAGWVERTWFWENSPKDPNDRDFTAL

VPHTELFRLVAASRYLILKRPGFQEHDMIPTSACATYPYAILLGLPQL

IDIEKRGSTFHISCSSCRLTNCLDSSAYDYAAIIVKRPPYVLLPVDIG

DEPWFDDSAILTFRYATDLIRA (See FIG. 8)

Cell Culture, Transfection and Stable Cell Line Generation

HEK293T cells (ATCC) were routinely maintained in Dulbecco's modified Eagles medium supplemented with 10% fetal bovine serum (Gibco) and 100 µg/ml Normycin. Transfection of HEK293T was performed using PEI as described previously [43]. Briefly, $10^5$ cells were seeded in 6 well plates one day before transfection and 2 µg of each plasmid were used for each well. To generate stable HEK293T cell lines harboring pHBRV Su-TAP-4C FW, the pHBRV Su-TAP-4C FW-Puromycin plasmid was linearized with PvuI and transfected into HEK293T cells. Individual clones were selected with Puromycin (Invitrogen).

Western Blot Analysis

Secreted HBRV Su protein in 400 µl supernatant was precipitated with TCA and dissolved in PBS. Cell lysates were prepared from transfected and stable cells using RIPA buffer with complete proteinase inhibitor (Roche). Approximately, $2\times10^6$ cells were collected and washed twice with ice-cold PBS, incubated with RIPA buffer on ice for 30 min and centrifuged at 20,000×g for 30 minutes. Proteins from cell supernatant and lysate were quantified using the BCA assay (Bio-Rad) and 50 µg and 100 µg of total protein from cell lysate and supernatant, respectively, were resolved by 10% sodium dodecyl sulfate (SDS)-polyacrylamide gel electrophoresis (PAGE) and transferred to nitrocellulose membrane as previously described (FIG. 14) [44].

Western blot analysis was performed using the primary polyclonal goat anti-MMTV envelope gp52 antibody, mouse monoclonal anti-Flag antibody (Sigma-Aldrich) and IRDye goat anti-mouse and rabbit anti-goat secondary antibodies (LI-COR). Reacting membranes were visualized with LI-COR Odyssey infrared imaging system.

For detection of serological reactivity to HBRV-Su, 100 ng of purified protein was resolved on a 10% SDS-PAGE minigel (Bio-Rad) and transferred to nitrocellulose membrane. The membrane was cut into 5 mm wide stripes. Each stripe was incubated with serum from a breast cancer patient or a control (1:400 dilution) and IRDye goat anti-human secondary antibody.

Scale Up of HBRV Su Production and Purification and Characterization

Stable cells expressing HBRV Su were expanded to 12×15 cm cell cultural dishes in Dulbecco's modified Eagles medium supplemented with 10% fetal bovine serum. The medium in each plate was replaced with 25 ml Pro293™ CD serum-free medium (Lonza) when cells reached 95% confluence. The medium was collected after 5-6 days incubation, centrifuged at 3,000 g for 20 min. The clarified medium was adjusted to pH 8.0 and filtered through 0.22 µm filter before purification.

Purification of HBRV Su was performed on 1 ml Histrap FF crude column and buffers as suggested by the supplier (GE Healthcare) using an AKTA explorer 100 (Amersham Pharmacia Biotech). The conditioned medium was loaded to the equilibrated column at the rate of 1 ml/min, the column was then washed with 20 ml binding buffer and eluted into 10×0.5 ml fractions using elution buffer. The peak elution fraction was combined and changed to proteins storage buffer by ultrafiltration (Millipore, 30 kDa cut-off limit concentrator, 4000 g for 20 min). The final preparation was aliquoted for storage at −80° C. for ELISA. The 10 eluted fractions were assessed by Western Blot analysis using anti-MMTV Env antibody or anti-FLAG antibody and 10% SDS-PAGE gels stained with Coomassie R-250 blue stain (Bio-Rad). The protein concentration was determined by BCA assay (Pierce) using bovine serum albumin (BSA) as a standard.

HBRV Su ELISA

ELISA were performed at room temperature with all sera in duplicate using high-binding microplates (Greiner, Monroe, USA). Briefly, wells were coated with 1001 of 2 ng/µl purified HBRV Su in PBS for 18 hours and blocked with 1% BSA in PBS for 3 hours. Serum was incubated at 100 µl/well at a 1:400 dilution in PBS with 1% BSA (Sigma) for 1 hour. A serial dilution of polyclonal anti-MMTV Env was included on each plate as a standard and then incubated with 100 µl/well donkey anti-human and donkey anti-goat secondary antibodies (Jackson Immuno-Research Lab) for 1 hour. The plate was washed 3×5 min after each step using PBS with 0.5% Tween. Plates were developed with 100 µl/well tetramethylbenzidine substrate (TMB, Sigma) for 20 min and then stopped with 50 µl/well 2N $H_2SO_4$. The absorbance at 450 nm and 540 nm (background) was measured with EMAX Plus Microplate Reader (Molecular Devices, USA) and the cut off level was established using the reactivity of control samples by adding the mean background level to 3×S.D. Two tailed Fisher's exact test was used to assess significant differences in frequency between different groups, followed by calculation of the odds ratio (Baptista-Pike methodology) along with sensitivity, specificity, positive predictive value, negative predictive value and likelihood ratio (Wilson Brown methodology) using Prism 8 software.

Results

HBRV Su Expression in HEK 293T Cells

Figure 14B:
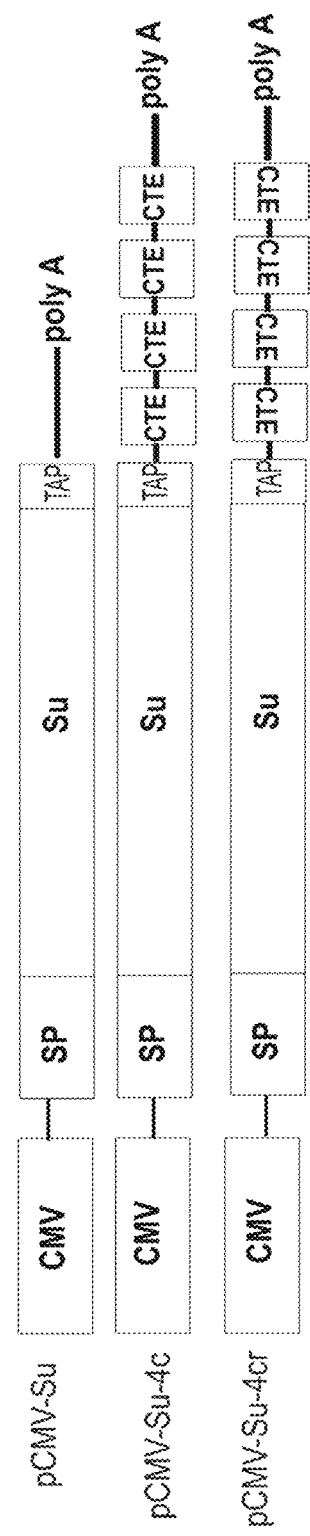
Figure 14C:
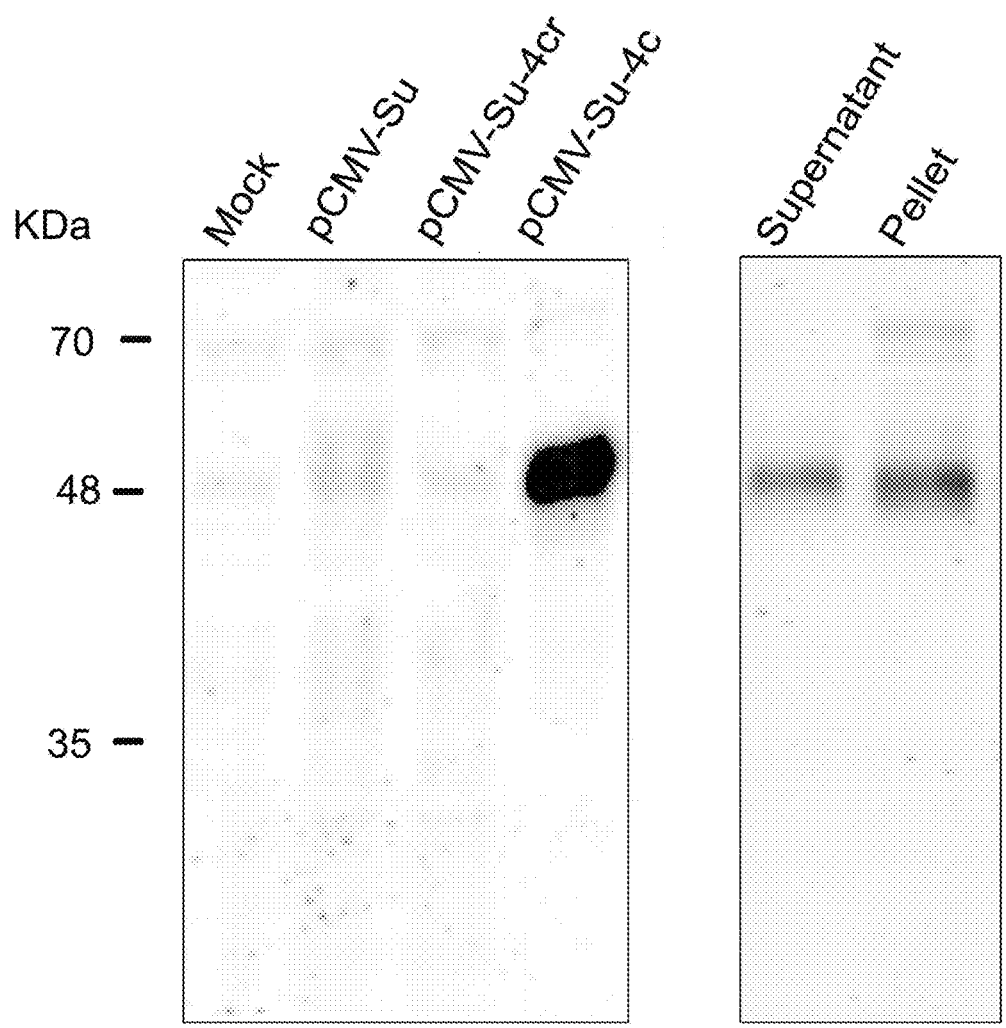

A mammalian expression system was employed to express the HBRV Su because prior attempts to express multiple constructs expressing HBRV Env protein in bacteria and baculovirus systems were not sufficiently productive. MMTV Env protein is encoded by a single spliced mRNA in mice, which produces a SP (p 14), Su (gp52) and transmembrane domain (gp36) (FIG. 14A); the Su protein is generated by removal of the signal peptide by signal peptidase and cleavage of the transmembrane domain by cellular Furin. Therefore, a mammalian expression vector pCMV Su-Tap was constructed, using the cytomegalovirus immediate early promoter to drive protein expression and a TAP tag to enable protein purification (FIG. 14B). Using the pCMV-Su-TAP construct, very little HBRV Su protein was detected in lysates from transfected HEK293T cells (FIG. 14C). Therefore an M-PMV cytoplasmic transport element (CTE) was incorporated into the construct to increase protein expression [42]. To this end, two additional Su expression constructs were generated with the 4 copies of M-PMV CTE inserted in the downstream of Su-TAP for expression studies. Following expression in HEK293T, increased production of HBRV Su was observed in cell lysates transfected with the pCMV-Su-Tap-4c but not in cells with the pCMV-Su-Tap-4cr construct that had the CTE arranged in the antisense orientation. Moreover, we were able to detect secreted Su protein in medium of the cell transfected with the pCMV-Su-Tap-4c plasmid two day after transfection (FIG. 14C).

Large Scale Production and Purification of HBRV Su

Figure 15A:
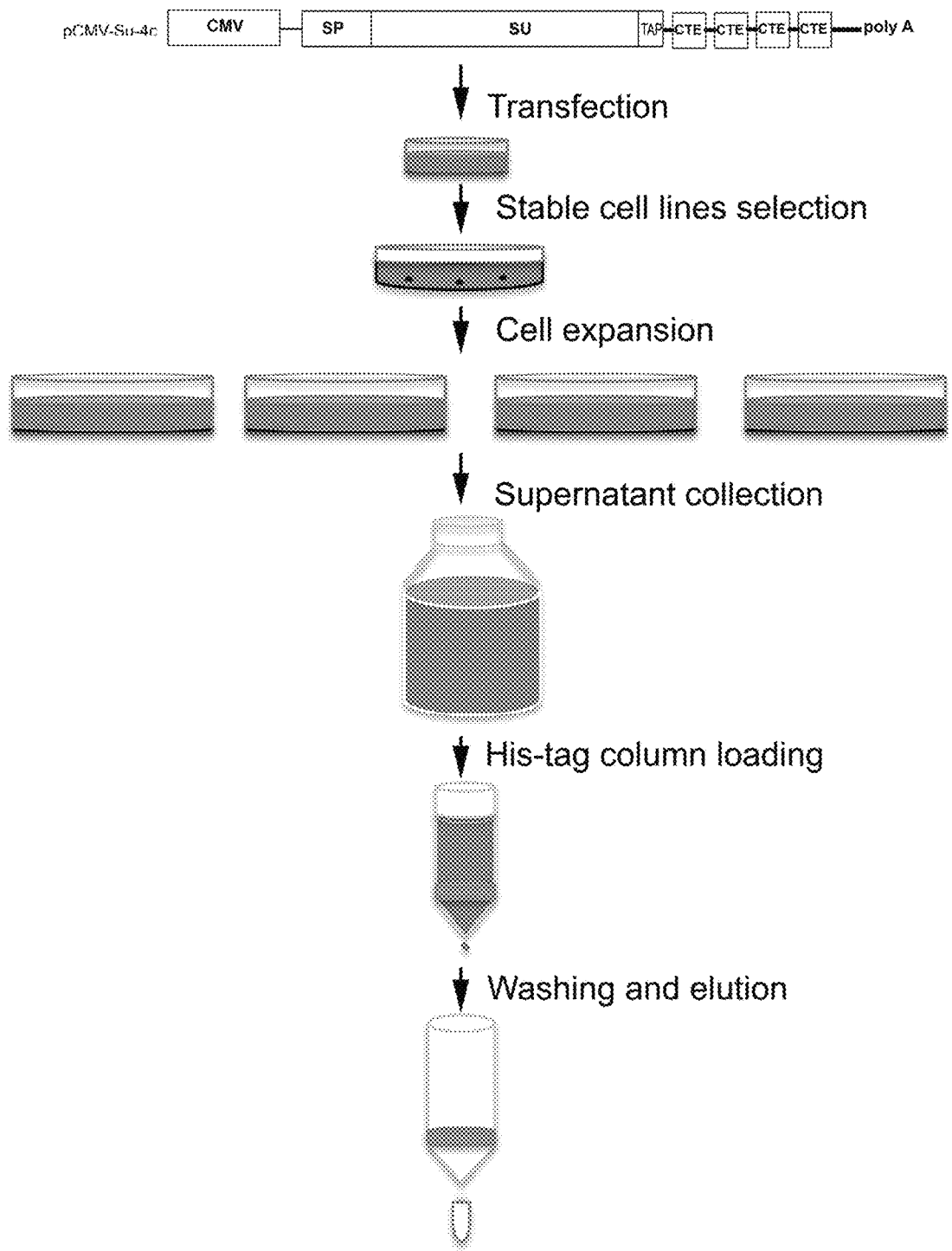
Figure 16:
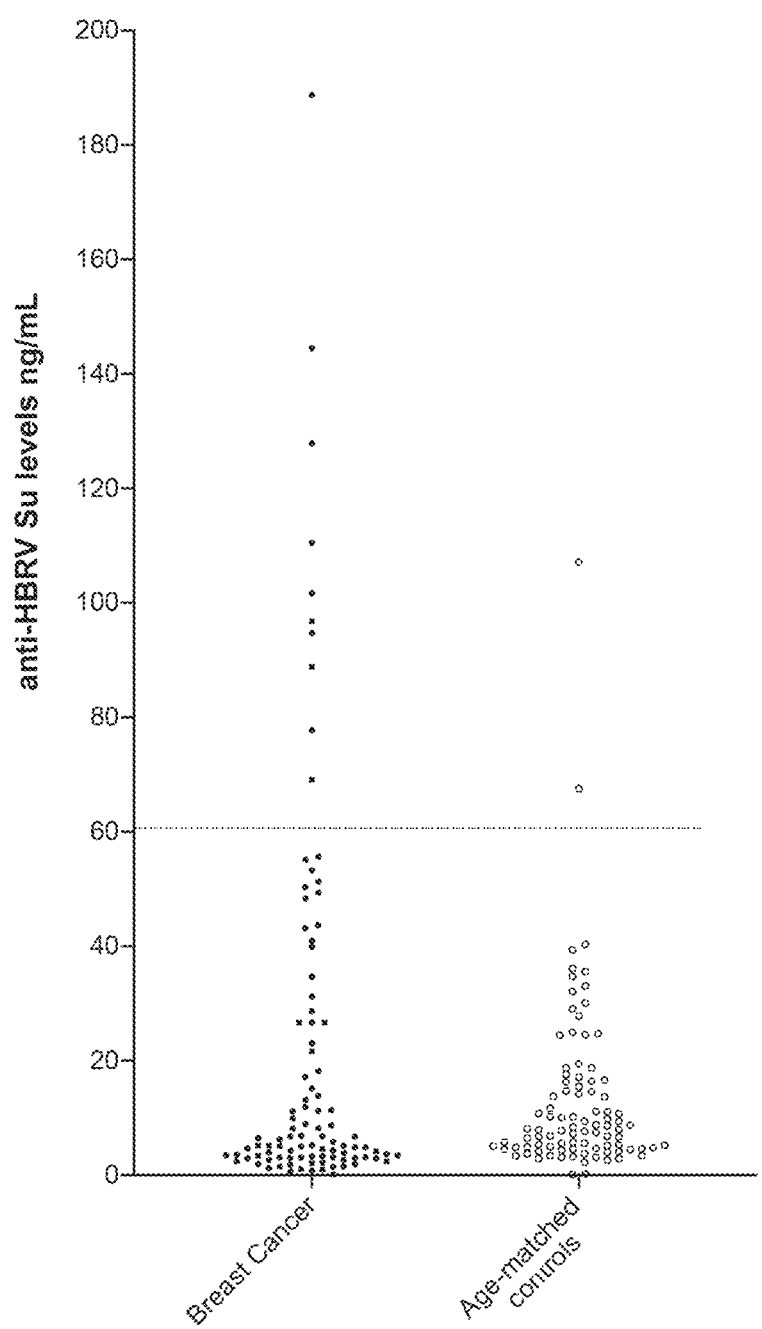
Figure 16:
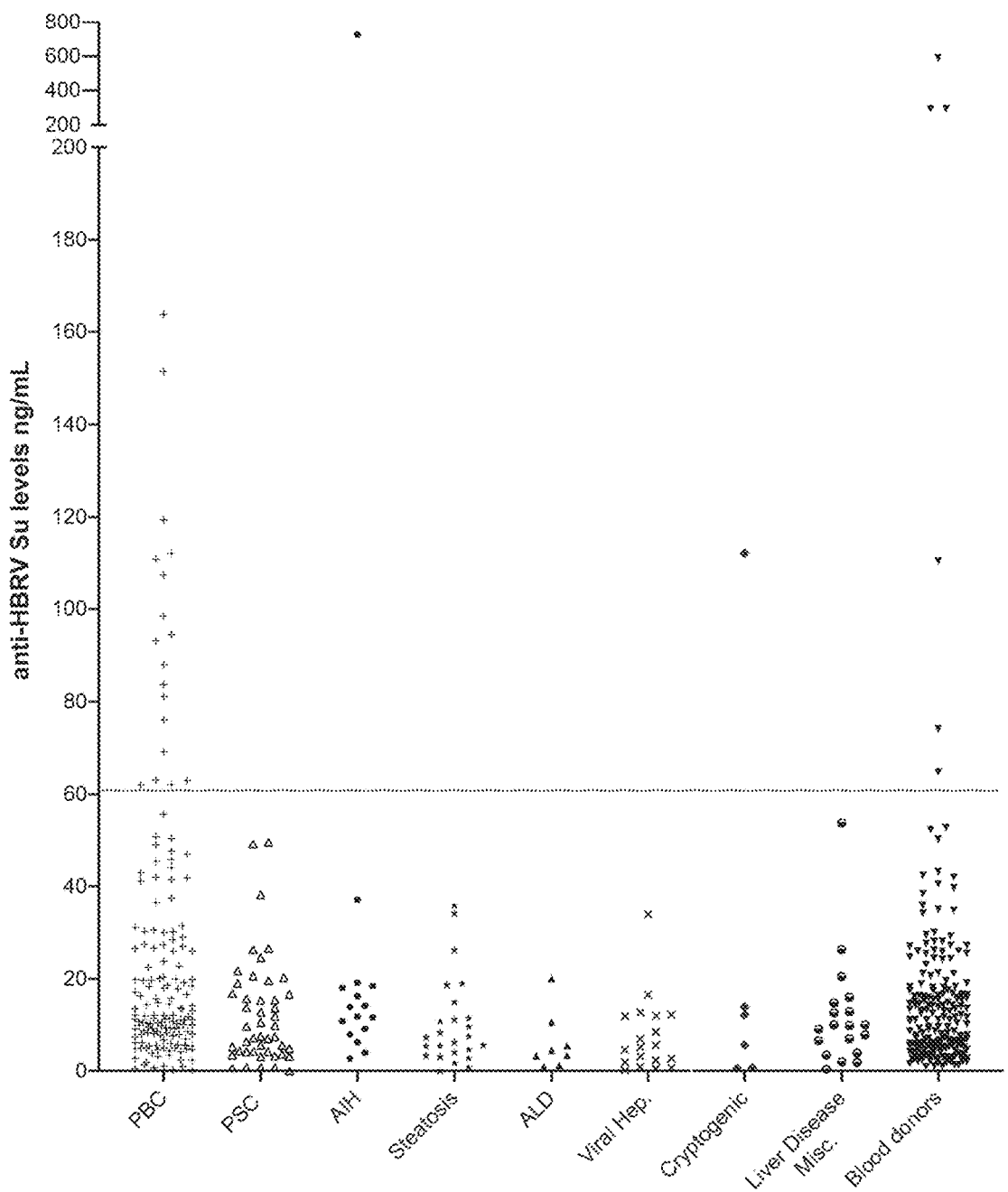

Since abundant HBRV Su protein was secreted from 293T cells transfected with the pCMV-Su-Tap-4c plasmids, a strategy was developed to purify the protein directly from a large-scale cell culture medium (FIG. 15A). Stable 293T cell lines were generated following transfection with the pCMV-Su-Tap-4c plasmid and the cells with the highest Su secretion in the culture medium were expanded to 12×15 cm cell culture dishes using DMEM medium supplement with 10% FBS. When cells reached 90-95% confluence, the medium was replaced with serum-free medium and incubated for another 5 days before collection. Approximately 300 ml was obtained for each batch, which was then purified with chromatography to derive 150-200 μg HBRV Su protein. SDS-PAGE revealed that the purified Su protein was homogenous and devoid of other contaminants. Western blot analysis with polyclonal anti-MMTV Env confirmed that the purified protein was HBRV Su along with select serum from seropositive and negative breast cancer and controls samples (FIGS. 15B and C).

Detection of Anti-HBRV Su Protein Antibodies by ELISA

The ELISA protocol was established using 200 ng/well of purified HBRV Su. The antibody response was calculated by converting the optical density reading to the equivalent ng/ml reactivity of the positive control, polyclonal anti-MMTV Env antibody. The background reactivity was calibrated using the serum samples from the age/sex matched healthy controls used as a comparison group for the breast cancer patients. The cut off level (mean background+3× S.D.) was calculated as 61 ng/mL and samples found to be greater than this were considered positive (FIG. 16). Accordingly, a greater proportion of breast cancer patients (10.2%) were found to have serological reactivity to HBRV Su versus 2.0% of age and sex matched control subjects (FIG. 16: P=0.017, OR=5.6 [1.25-26.3]).

The seroprevalence of HBRV Su reactivity in patients with PBC was comparable to that observed in patients with breast cancer (FIG. 16: 11.5% vs. 10.2%). The frequency of HBRV Su reactivity was significantly higher in PBC patients vs. blood donors (11.5% vs. 3.1%, P=0.0024, OR=4.09 [1.66-10.1]). In prior studies using the gold standard methodology of detecting HBRV integrations in patients' cholangiocytes, subjects with cryptogenic liver disease and AIH were found to harbor infection and in this study, isolated reactivity was observed in subjects with cryptogenic liver disease (16.7%) and AIH (6.3%); whereas other subjects with liver disease were universally negative (FIG. 16B).

While reactivity in healthy blood donors was incrementally higher than the healthy age/sex-matched comparison group for the breast cancer patients, the difference was not found to be significant (3.1% vs. 2.0%; p=0.72). The sensitivity of the HBRV Su ELISA was limited in detecting reactivity in patients with breast cancer and PBC as compared to their respective control groups (10.2% [5.6%-17.8%] and 11.5% [7.4%-17.5%]). Whereas the assay was highly specific for serologic detection in patients with breast cancer and PBC, respectively (98.0% [93.1%-99.7%] and 97.0% [93.4%-98.6%]). Accordingly, the positive predictive values (83.3% [55.2%-97.0%] and 75.0% [55.1%-88.0%]) were diagnostically more useful that the negative predictive values (53.2% [46.1%-60.2%] and 57.7% [52.3%-62.9%]) for patients in the breast cancer and the liver disease study groups.

As described herein, an HBRV ELISA was used for assessing the seroprevalence of infection in patients. Approximately 10% of breast cancer and PBC patients had detectable anti-HBRV Su, and the test was found to be highly specific for both disorders. The likelihood ratios for having breast cancer with HBRV Su reactivity was 5.2 and for having PBC with HBRV Su reactivity was 3.7: the difference in likelihood ratios probably reflects the chosen control groups for each disorder. Notably, the breast cancer control subjects were mainly middle aged women and therefore a more suitable control group for the PBC patients, who are also predominatly female; whereas the blood donors were more of an admixture of both sexes. The healthy comparison groups revealed a sizeable population seroprevalence of ~2-3%. One hypothesis may be that HBRV infection may only be disease related in genetically predisposed individuals [10, 45].

Prior seroprevalence studies using MMTV proteins have been widely inconsistent. For example, an ELISA based study using MMTV proteins demonstrated serological reactivity in 26% of breast cancer patients and 8% of healthy controls [46]. A similar study found no difference between breast cancer patients and their respective controls [47] and a study using 4 strains of MMTV reported only non-specific reactivity in breast cancer patients, although reactivity consistent with the molecular weights of viral proteins was observed in individual strains of MMTV [39]. In studies of patients with liver disease, MMTV Western blot reactivity was attributed to autoreactivity with the anti-mitochondrial antibody, which is found in up to 95% of patients and used for diagnosing PBC [29], whereas, similar MMTV Western blot studies employing mitochondrial proteins to remove the autoantibodies from PBC patients' serum, demonstrated the presence of signal [48]. As purified anti-mitochondrial antibody has no reactivity with HBRV Su, we conclude that humans do make humoral responses to HBRV based on our ELISA.

The prevalence of infection detected by the HBRV Su ELISA as described was somewhat lower than other reports using different techniques to diagnose disease. For example, a metanalysis of molecular epidemiological studies reported a prevalence of 40% HBRV infection in Western countries based on PCR detection of betaretrovirus sequences in breast cancer samples [49]. An even higher prevalence of infection has been reported in PBC patients based on the presence of proviral HBRV integrations detected by ligation mediated PCR and Illumina sequencing, with provirus found in 58% of cholangiocytes from patients with PBC as compared to 7% of non-autoimmune liver disease controls [30]. The discrepancy of a higher frequency of viral infection in tissue as compared to a lower seroprevalence of anti-HBRV Su reactivity may be partly explained by observations from neonatal mouse infection. Weanling pups have a high risk of developing breast cancer from MMTV infection because they become immunotolerant to viral infection. This occurs because MMTV is taken up in the gut associated lymphoid tissue along with bacterial lipopolysaccharide, which triggers a cascade of events. The lipopolysaccharide/viral complex engages toll-like receptor 4 that in turn triggers an IL-4 and IL-6 dependent production of IL-10, which renders the mouse unresponsive to MMTV Su and prevents the formation of neutralizing antibodies [13]. It is currently unknown whether a similar immunological process may occur in humans with HBRV infection. Notably the cellular immune response to HBRV peptides are more prevalent in patients with liver disease [50].

One goal of the present study was to derive a reliable and reproducible diagnostic ELISA to investigate the frequency of HBRV infection. In prior experiments, we used bacterial or baculovirus expressed proteins but failed to generate sufficient amounts of pure viral protein. We also generated serological data using the bacterially expressed Gag proteins and while a higher seroprevalence was observed in our PBC population as a whole, no significant differences were found between patients and controls with liver disease. Notably, cross reactivity with retroviral Gag (Group AntiGen) is a common occurrence in patients with any viral infection due to the positively charged antigenic determinants in capsid and core proteins surrounding the viral genome [51, 52]. For this ELISA, a unique strategy for large scale production of purified and secreted HBRV Su protein was developed using HEK 293T cells. Three factors contributed to the production of HBRV Su sufficient for multiple ELISA assays: these included (i) using multiple copies of CTE downstream of the Su coding region to enhance HBRV Su expression and secretion; (ii) ensuring the stable expression of HBRV Su protein in human cells; and (iii) replacing the FBS containing medium with serum-free medium to remove a source of protein contamination and ensure the high purity of protein after chromatography purification. It is also suspected that the use of HBRV rather than MMTV proteins to assess the betaretrovirus seroprevalence likely improved the accuracy of the assay.

CONCLUSIONS

In this example, an HBRV ELISA assay has been constructed by expressing HBRV env in HEK293 to produce purified HBRV Su protein. The ELISA detection of HBRV Su antibodies is highly specific for both breast cancer and PBC (although the assay implementation example may somewhat lack sensitivity (relatively) under the conditions tested, as higher prevalence rates for HBRV Infection have been recorded using other techniques).

TABLE 2

References cited in Example 7:

1. Jemal, A., et al., Global cancer statistics. CA Cancer J Clin, 2011. 61(2): p. 69-90.
2. Bray, F., et al., Global cancer statistics 2018: GLOBOCAN estimates of incidence and mortality worldwide for 36 cancers in 185 countries. CA Cancer J Clin, 2018. 68(6): p. 394-424.
3. Lawson, J.S., et al., Association of Mouse Mammary Tumor Virus With Human Breast Cancer: Histology, Immunohistochemistry and Polymerase Chain Reaction Analyses. Front Oncol, 2018. 8: p. 141.
4. Lawson, J.S. and W.K. Glenn, Multiple oncogenic viruses are present in human breast tissues before development of virus associated breast cancer. Infect Agent Cancer, 2017. 12: p. 55.
5. Sliva, K., et al., Murine leukemia virus (MLV) replication monitored with fluorescent proteins. Virol J, 2004. 1(1): p. 14.
6. Xu, L., et al., Cloning the human betaretrovirus proviral genome from patients with primary biliary cirrhosis. Hepatology, 2004. 39(1): p. 151-6.
7. Wang, Y., et al., Detection of mammary tumor virus env gene-like sequences in human breast cancer. Cancer Res, 1995. 55(22): p. 5173-9.
8. Wang, Y., et al., Detection of MMTV-like LTR and LTR-env gene sequences in human breast cancer. Int J Oncol, 2001. 18(5): p. 1041-4.
9. Xu, L., et al., Does a betaretrovirus infection trigger primary biliary cirrhosis? Proc Natl Acad Sci of the U S A, 2003. 100(14): p. 8454-9.
10. Mason, A.L., S.Y. Gilady, and J.R. Mackey, Mouse mammary tumor virus in human breast cancer red herring or smoking gun? The American journal of pathology, 2011. 179(4): p. 1588-90.
11. Cohen, J.C., et al., Integration of the DNA of mouse mammary tumor virus in virus-infected normal and neoplastic tissue of the mouse. Cell, 1979. 16(2): p. 333-45.
12. Dudley, J.P., T.V. Golovkina, and S.R. Ross, Lessons Learned from Mouse Mammary Tumor Virus in Animal Models. ILAR J, 2016. 57(1): p. 12-23.
13. Kane, M., et al., Successful transmission of a retrovirus depends on the commensal microbiota. Science, 2011. 334(6053): p. 245-9.
14. Acha-Orbea, H. and H.R. MacDonald, Superantigens of mouse mammary tumor virus. Annu Rev Immunol, 1995. 13: p. 459-86.
15. Moore, D.H., et al., Search for a human breast cancer virus. Nature, 1971. 229(5287): p. 611-4,
16. Zotter, S., et al., Mouse mammary tumour virus-related antigens in core-like density fractions from large samples of women's milk. Eur J Cancer, 1980. 16(4): p. 455-67.
17. Day, N.K., et al., Antibodies reactive with murine mammary tumor virus in sera of patients with breast cancer: geographic and family studies. Proc Natl Acad Sci U S A, 1981. 78(4): p. 2483-7.
18. Mazzanti, C.M., et al., Human saliva as route of inter-human infection for mouse mammary tumor virus. Oncotarget, 2015. 6(21): p. 18355-63.
19. Levine, P.H., et al., Increased incidence of mouse mammary tumor virus-related antigen in Tunisian patients with breast cancer, Int J Cancer, 1984. 33(3): p. 305-8.
20. Witkin, S.S., et al., Antigens and antibodies cross-reactive to the murine mammary tumor virus in human breast cyst fluids. J Clin Invest, 1981. 67(1): p. 216-22.
21. Litvinov, S.V. and T.V. Golovkina, Expression of proteins immunologically related to murine mammary tumour virus (MMTV) core proteins in the cells of breast cancer continuous lines MCF-7, T47D, MDA-231 and cells from human milk. Acta Virol, 1989. 33(2): p. 137-42.
22. Keydar, I., et al., Properties of retrovirus-like particles produced by a human breast carcinoma cell line: immunological relationship with mouse mammary tumor virus proteins. Proc Natl Acad Sci U S A, 1984. 81(13): p. 4188-92.
23. Zammarchi, F., et al., MMTV-like sequences in human breast cancer: a fluorescent PCR/laser microdissection approach. J Pathol, 2006. 209(4): p. 436-44.
24. Al Dossary, R., K.R. Alkharsah, and H. Kussaibi, Prevalence of Mouse Mammary Tumor Virus (MMTV)-like sequences in human breast cancer tissues and adjacent normal breast tissues in Saudi Arabia. BMC cancer, 2018. 18(1): p. 170-170.
25. Hachana, M., et al., Prevalence and characteristics of the MMTV-like associated breast carcinomas in Tunisia. Cancer Lett, 2008. 271(2): p. 222-30.
26. Naushad, W., et al., Detection and identification of mouse mammary tumor virus-like DNA sequences in blood and breast tissues of breast cancer patients. Tumour Biol, 2014. 35(8): p. 8077-86.

TABLE 2-continued

References cited in Example 7:

27. Melana, S.M., et al., [Detection of murine mammary tumor virus (MMTV) env gene-like sequences in breast cancer from Argentine patients]. Medicina (B Aires), 2002. 62(4): p. 323-7.
28. Cheung, A.C., et al., Time to make the change from 'primary biliary cirrhosis' to 'primary biliary cholangitis'. Can J Gastroenterol Hepatol, 2015. 29(6): p. 293.
29. Mason, A., Is PBC a viral infectious disease? Best Practice & Research Clinical Gastroenterology, 2018. 27e39:27-39: p. DOI 10.1016/j.bpg.2018.06.001.
30. Wang, W., et al., Frequent proviral integration of the human betaretrovirus in biliary epithelium of patients with autoimmune and idiopathic liver disease. Aliment Pharmacol Ther, 2015. 41(4): p. 393-405.
31. Lytvyak, E., et al., Randomized controlled trial: Combination antiretroviral therapy with Tenofovir-Emtricitabine and Lopinavir-Ritonavir in patients with primary biliary cholangitis. Canadian Liver Journal, 2018. in press.
32. Lytvyak, E., et al., Combination Anti-Retroviral Therapy Provides Reduction in Human Betaretrovirus Load and Durable Biochemical Responses in Patients with Primary Biliary Cirrhosis Hepatology, 2015. 62((suppl)): p. 528A.
33. Lytvyak, E., A.J. Montano-Loza, and A.L. Mason, Combination antiretroviral studies for patients with primary biliary cirrhosis. World J Gastroenterol, 2016. 22(1): p. 349-60.
34. Mason, A.L., et al., Clinical trial: randomized controlled study of zidovudine and lamivudine for patients with primary biliary cirrhosis stabilized on ursodiol. Alimentary Pharmacology & Therapeutics, 2008. 28(7): p. 886-894.
35. Fukuoka, H., et al., No association of mouse mammary tumor virus-related retrovirus with Japanese cases of breast cancer. J Med Virol, 2008. 80(8): p. 1447-51.
36. Motamedifar, M., M. Saki, and A. Ghaderi, Lack of association of mouse mammary tumor virus-like sequences in Iranian breast cancer patients. Med Princ Pract, 2012. 21(3): p. 244-8.
37. Selmi, C., et al., Lack of immunological or molecular evidence for a role of mouse mammary tumor retrovirus in primary biliary cirrhosis. Gastroenterology, 2004. 127(2): p. 493-501.
38. Johal, H., et al., Mouse mammary tumour virus-like virus (MMTV-LV) is present within the liver in a wide range of hepatic disorders and unrelated to nuclear p53 expression or hepatocarcinogenesis. J Hepatol, 2009. 50(3): p. 548-54.
39. Goedert, J.J., C.S. Rabkin, and S.R. Ross, Prevalence of serologic reactivity against four strains of mouse mammary tumour virus among US women with breast cancer. Br J Cancer, 2006. 94(4): p. 548-51.
40. Borugian, M.J., et al., The Canadian Partnership for Tomorrow Project: building a pan-Canadian research platform for disease prevention. Cmaj, 2010. 182(11): p. 1197-201.
41. Puig, O., et al., The tandem affinity purification (TAP) method: a general procedure of protein complex purification. Methods, 2001. 24(3): p. 218-29.
42. Wodrich, H., A. Schambach, and H.G. Krausslich, Multiple copies of the Mason-Pfizer monkey virus constitutive RNA transport element lead to enhanced HIV-1 Gag expression in a context-dependent manner. Nucleic Acids Res, 2000. 28(4): p. 901-10.
43. Zhang, G., et al., Pericentriolar Targeting of the Mouse Mammary Tumor Virus GAG Protein. PLoS One, 2015. 10(6): p. e0131515.
44. Sanfacon, H. and G. Zhang, Analysis of interactions between viral replicase proteins and plant intracellular membranes. Methods in molecular biology, 2008. 451: p. 361-75.
45. Hirschfield, G.M., et al., The genetics of complex cholestatic disorders. Gastroenterology, 2013. 144(7): p. 1357-74.
46. Witkin, S.S., et al., An enzyme-linked immunoassay for the detection of antibodies to the mouse mammary tumor virus: application to human breast cancer. J Immunol Methods, 1980. 32(1): p. 85-91.
47. Dion, A.S., et al., Responses of serum from breast cancer patients to murine mammary tumor virus: fact or artifact? J Natl Cancer Inst, 1987. 79(2): p. 207-11.
48. Mason, A., et al., Patients with primary biliary cirrhosis make anti-viral and anti-mitochondrial antibodies to mouse mammary tumor virus. Gastroenterology, 2004. 127(6): p. 1863-1864.
49. Wang, F., et al., Mouse mammary tumor virus-like virus infection and the risk of human breast cancer: a meta-analysis. Am J Transl Res, 2014. 6(3): p. 248-66.
50. Rahbari, M., et al., Virological footprint of T-Cell responses in patients with primary biliary cirrhosis. Canadian Journal of Gastroenterology and Hepatology 2015. 29: p. 159A.
51. Mason, A., et al., Detection of retroviral antibodies in primary biliary cirrhosis and other idiopathic biliary disorders. Lancet, 1998. 351(9116): p. 1620-1624.
52. Karlin, S. and V. Brendel, Charge configurations in viral proteins. Proc Natl Acad Sci U S A, 1988. 85(24): p. 9396-400.

REFERENCES

1. Mason A, Xu L, Guo L, et al. Detection of retroviral antibodies in primary biliary cirrhosis and other idiopathic biliary disorders. Lancet 1998; 351:1620-24.
2. Xu L, Sakalian M, Shen Z, et al. Cloning the human betaretrovirus proviral genome from patients with primary biliary cirrhosis. Hepatology 2004; 39:151-6.
3. Xu L, Shen Z, Guo L, et al. Does a betaretrovirus infection trigger primary biliary cirrhosis? Proc Natl Acad Sci of the USA 2003; 100:8454-9.
4. Wang W, Wasilenko S, Indik S, et al. Isolation of the human betaretrovirus and demonstration of integration sites in patients with primary biliary cirrhosis. Canadian Journal of Gastroenterology 2012; 26:84A.

5. Wang W, Indik S, Wasilenko S T, et al. Frequent proviral integration of the human betaretrovirus in biliary epithelium of patients with autoimmune and idiopathic liver disease. Aliment Pharmacol Ther 2015; 41:393-405.
6. Sadamoto T, Joplin R, Keogh A, et al. Expression of pyruvate-dehydrogenase complex PDC-E2 on biliary epithelial cells induced by lymph nodes from primary biliary cirrhosis. Lancet 1998; 352:1595-6.
7. Sharon D, Chen M, Zhang G, et al. Impact of combination antiretroviral therapy in the NOD.c3c4 mouse model of autoimmune biliary disease. Liver Int 2015; 35:1442-50.
8. Zhang G, Chen M, Graham D, et al. Mouse mammary tumor virus in anti-mitochondrial antibody producing mouse models. J Hepatol 2011; 55:876-84.
9. Wysokinski F, Meng B, Wang W, et al. Cholangiocytes from Patients with Primary Biliary Cholangitis Display The Warburg Effect with Increased Mitochondria, Oxygen Consumption and Glycolytic Activity. Hepatology 2017; 66:S933A.
10. Rahbari M, Sharon D, Landi A, et al. Virological footprint of T-Cell responses in patients with primary biliary cirrhosis. Canadian Journal of Gastroenterology and Hepatology 2015; 29:159A.
11. Mason A L, Lindor K D, Bacon B R, et al. Clinical trial: randomized controlled study of zidovudine and lamivudine for patients with primary biliary cirrhosis stabilized on ursodiol. Alimentary Pharmacology & Therapeutics 2008; 28:886-894.
12. Lytvyak E, Montano-Loza A, Saxinger L, et al. Combination Anti-Retroviral Therapy Provides Reduction in Human Betaretrovirus Load and Durable Biochemical Responses in Patients with Primary Biliary Cirrhosis Hepatology 2015; 62:528A.
13. Johal H, Scott G M, Jones R, et al. Mouse mammary tumour virus-like virus (MMTV-LV) is present within the liver in a wide range of hepatic disorders and unrelated to nuclear p53 expression or hepatocarcinogenesis. J Hepatol 2009; 50:548-54.
14. Mason A. Is PBC a viral infectious disease? Best Practice & Research Clinical Gastroenterology 2018; in press:DOI 10.1016/j.bpg.2018.06.001.
15. Mason A, Sis B. Primary Biliary Cirrhosis. In: Shaffner E, Thomson A, eds. First Principles in Gastroenterology and Hepatolgy. Volume 7, 2014:86-94.
16. Poupon R. Primary biliary cirrhosis: a 2010 update. J Hepatol 2010; 52:745-58.
17. Montano-Loza A J, Wasilenko S, Bintner J, et al. Cyclosporine A Protects Against Primary Biliary Cirrhosis Recurrence After Liver Transplantation. Am J Transplant 2010; 10:852-858.
18. Angulo P, Batts K P, Therneau T M, et al. Long-term ursodeoxycholic acid delays histological progression in primary biliary cirrhosis. Hepatology 1999; 29:644-7.
19. Combes B, Carithers R L, Maddrey W C, et al. A randomized double-blind, placebo-controlled trial of ursodeoxycholic acid in primary biliary cirrhosis. Hepatology 1995; 22:759-66.
20. Heathcote E J, Cauch-Dudek K, Walker V, et al. The Canadian double blind randomized controlled trial of ursodeoxycholic acid in primary biliary cirrhosis. Hepatology 1994; 19:1149-56.
21. Lindor K D, Therneau T M, Jorgensen R A, et al. Effects of ursodeoxycholic acid on survival in patients with primary biliary cirrhosis [see comments]. Gastroenterology 1996; 110:1515-8.
22. Poupon R E, Balkau B, Eschwege E, et al. A multicenter, controlled trial of ursodiol for the treatment of primary biliary cirrhosis. UDCA-PBC study group. N. Eng. J. Med. 1991; 324:1548-54.
23. Poupon R E, Poupon R, Balkau B, et al. Ursodiol for the long term treatment of primary biliary cirrhosis. N. Eng. J. Med. 1994; 330:1342-7.
24. Hirschfield G M, Mason A, Luketic V, et al. Efficacy of obeticholic acid in patients with primary biliary cirrhosis and inadequate response to ursodeoxycholic acid. Gastroenterology 2015; 148:751-61 e8.
25. Nevens F, Andreone P, Mazzella G, et al. A Placebo-Controlled Trial of Obeticholic Acid in Primary Biliary Cholangitis. N Engl J Med 2016; 375:631-43.
26. Lytvyak E, Hosamani I, Montano-Loza A, et al. Randomized controlled trial: Combination antiretroviral therapy with Tenofovir-Emtricitabine and Lopinavir-Ritonavir in patients with primary biliary cholangitis. Canadian Liver Journal 2018; in press.
27. Mason A, Nair S. Primary biliary cirrhosis: new thoughts on pathophysiology and treatment. Curr Gastroenterol Rep 2002; 4:45-51.
28. Mason A, Xu L, Guo L, et al. Detection of retroviral antibodies in primary biliary cirrhosis and other idiopathic biliary disorders. Lancet 1998; 351:1620-1624.
29. Xu L, Guo L, Shen Z, et al. Duplication of MERI15 on chromosome 4 in patients with primary biliary cirrhosis. Liver International 2009; 29:375-383.
30. Acha-Orbea H, Palmer E. Mls—a retrovirus exploits the immune system [see comments]. Immunol Today 1991; 12:356-61.
31. Selmi C, Ross S R, Ansari A A, et al. Lack of immunological or molecular evidence for a role of mouse mammary tumor retrovirus in primary biliary cirrhosis. Gastroenterology 2004; 127:493-501.
32. Wysokinski F, Meng B, Wang W, et al. Cholangiocytes from patients with primary biliary cholangitis display the Warburg effect with increased mitochondria, oxygen consumption and glycolytic activity. Hepatology 2017; 66:S933A.
33. Lamb R, Bonuccelli G, Ozsvari B, et al. Mitochondrial mass, a new metabolic biomarker for stem-like cancer cells: Understanding WNT/FGF-driven anabolic signaling. Oncotarget 2015; 6:30453-71.
34. Zhang G, Chen M, Graham D, et al. Mouse Mammary Tumor Virus in Anti-Mitochondrial Antibody Producing Mouse Models Journal of Hepatology 2011, 55:876-884.
36. Wasilenko S T, Mason G E, Mason A L. Primary biliary cirrhosis, bacteria and molecular mimicry: what's the molecule and where's the mimic? Liver Int 2009; 29:779-82.
37. Mason A, Xu L, Shen Z, et al. Patients with primary billary cirrhosis make anti-viral and anti-mitochondrial antibodies to mouse mammary tumor virus. Gastroenterology 2004; 127:1863-1864.
38. Kane M, Case L K, Kopaskie K, et al. Successful transmission of a retrovirus depends on the commensal microbiota. Science 2011:334:245-9.
39. Purdy A, Case L, Duvall M, et al. Unique resistance of I/LnJ mice to a retrovirus is due to sustained interferon gamma-dependent production of virus-neutralizing antibodies. J Exp Med 2003; 197:233-43.
40. Gershwin M E, Coppel R L, Mackay I R. Primary biliary cirrhosis and mitochondrial autoantigens. Insights from molecular biology. Hepatology 1988; 8:147-151.
41. Kaplan M M, Gershwin M E. Primary biliary cirrhosis. N Engl J Med 2005; 353:1261-73.

42. Perrillo R P, Mason A L, Jacob S, et al. Hepatitis and cholestasis in a middle-aged woman [clinical conference]. Hepatology 1996; 24:730-4.
43. Van-de-Water J, Cooper A, Surh C D, et al. Detection of autoantibodies to the recombinant 74 Kd and 52 Kd mitochondrial autoantigens of primary biliary cirrhosis. New England Journal of Medicine 1989; 320:1377-80.
44. Krams S M, Dorshkind K, Gershwin M E. Generation of biliary lesions after transfer of human lymphocytes into severe combined immunodeficient (SCID) mice. J Exp Med 1989; 170:1919-30.
45. Krams S M, Surh C D, Coppel R L, et al. Immunization of experimental animals with dihydrolipoamide acetyltransferase, as a purified recombinant polypeptide, generates mitochondrial antibodies but not primary biliary cirrhosis. Hepatology 1989; 9:411-6.
46. Dyson J K, Hirschfield G M, Adams D H, et al. Novel therapeutic targets in primary biliary cirrhosis. Nat Rev Gastroenterol Hepatol 2015.
47. Gish R G, Mason A. Autoimmune liver disease. Current standards, future directions. Clin Liver Dis 2001; 5:287-314.
48. Katsumi T, Tomita K, Leung P S, et al. Animal models of primary biliary cirrhosis. Clin Rev Allergy Immunol 2015; 48:142-53.
49. Subsin B, Zhang G, Girgis S, et al. Splenocyte transfer in the NOD.c3c4 mouse model of primary biliary cirrhosis is associated with cholangitis and mouse mammary tumor virus infection. J. Hepatol. 2011: Abstract.
50. Neuberger J, Thompson R. PBC and AMA—What is the connection? Hepatology 1999; 29:271-277.
51. Shimoda S, Van de Water J, Ansari A, et al. Identification and precursor frequency analysis of a common T cell epitope motif in mitochondrial autoantigens in primary biliary cirrhosis. J Clin Invest 1998; 102:1831-40.
52. He X S, Rehermann B, Lopez-Labrador F X, et al. Quantitative analysis of hepatitis C virus-specific CD8(+) T cells in peripheral blood and liver using peptide-MHC tetramers. Proc Natl Acad Sci USA 1999; 96:5692-7.
53. Mangeney M, Renard M, Schlecht-Louf G, et al. Placental syncytins: Genetic disjunction between the fusogenic and immunosuppressive activity of retroviral envelope proteins. Proc Natl Acad Sci USA 2007; 104:20534-9.
54. Morozov V A, Morozov A V, Semaan M, et al. Single mutations in the transmembrane envelope protein abrogate the immunosuppressive property of HIV-1. Retrovirology 2012; 9:67.
55. Schlecht-Louf G, Renard M, Mangeney M, et al. Retroviral infection in vivo requires an immune escape virulence factor encrypted in the envelope protein of oncoretroviruses. Proc Natl Acad Sci USA 2010; 107: 3782-7.
56. Jude B A, Pobezinskaya Y, Bishop J, et al. Subversion of the innate immune system by a retrovirus. Nat Immunol 2003; 4:573-8.
57. Rassa J C, Meyers J L, Zhang Y, et al. Murine retroviruses activate B cells via interaction with toll-like receptor 4. Proc Natl Acad Sci USA 2002; 99:2281-6.
58. Xystrakis E, Yuksel M, Lin F, et al. Impact of Donation Mode on the Proportion and Function of T Lymphocytes in the Liver. PLoS One 2015; 10:e0139791.
59. Abofayed H, Gandhi B, Mason A. Proinflammatory Cellular Immune Responses to Human Betaretrovirus in Patients with Primar Biliary Cholangitis [AASLD abstract] Hepatology 2018; in press.
60. Mazurek G H, Villarino M E, Cdc. Guidelines for using the QuantiFERON-TB test for diagnosing latent *Mycobacterium tuberculosis* infection. Centers for Disease Control and Prevention. MMWR Recomm Rep 2003; 52:15-8.
61. Howley M M, Painter J A, Katz D J, et al. Evaluation of QuantiFERON-TB gold in-tube and tuberculin skin tests among immigrant children being screened for latent tuberculosis infection. Pediatr Infect Dis J 2015; 34:35-9.
62. Walker S, Fazou C, Crough T. et al. Ex vivo monitoring of human cytomegalovirus-specific CD8+ T-cell responses using QuantiFERON-CMV. Transpl Infect Dis 2007; 9:165-70.
63. Chiereghin A, Potena L, Borgese L, et al. Monitoring of CMV-specific cell-mediated immunity in heart transplant recipients: clinical utility of the QuantiFERON®-CMV assay for the management of post-transplant CMV infection. J Clin Microbiol 2018.
64. QuantiFERON-TB Gold Plus (QFT-Plus) Package Insert
65. Mason A L, Gilady S Y, Mackey J R. Mouse mammary tumor virus in human breast cancer red herring or smoking gun? The American journal of pathology 2011; 179: 1588-90.
66. Fleming T, Dunne J, Crowley B. Ex vivo monitoring of human cytomegalovirus-specific CD8(+) T-Cell responses using the QuantiFERON-CMV assay in allogeneic hematopoietic stem cell transplant recipients attending an Irish hospital. J Med Virol 2010; 82:433-40.
67. Dion A S, Girardi A J. Williams C C, et al. Serologic responses to murine mammary tumor virus (MuMTV) in MuMTV-exposed laboratory personnel. J Natl Cancer Inst 1986; 76:611-9.
68. Missale G, Bertoni R, Lamonaca V, et al. Different clinical behaviors of acute hepatitis C virus infection are associated with different vigor of the anti-viral cell-mediated immune response. J Clin Invest 1996, 98:706-14.
69. Larrubia J R, Benito-Martinez S, Miquel J, et al. Bim-mediated apoptosis and PD-1/PD-L1 pathway impair reactivity of PD1(+)/CD127(−) HCV-specific CD8 (+) cells targeting the virus in chronic hepatitis C virus infection. Cell Immunol 2011; 269:104-14.
70. (http://tools.iedb.org/mhci/).
71. Kim Y, Ponomarenko J, Zhu Z, et al. Immune epitope database analysis resource. Nucleic Acids Res 2012; 40:W525-30.
72. Pickett B E, Sadat E L, Zhang Y, et al. ViPR: an open bioinformatics database and analysis resource for virology research. Nucleic Acids Res 2012; 40:D593-8.
73. Nielsen M, Lundegaard C, Worning P, et al. Reliable prediction of T-cell epitopes using neural networks with novel sequence representations. Protein Sci 2003; 12:1007-17.
74. Lundegaard C, Lamberth K, Harndahl M, et al. NetMHC-3.0: accurate web accessible predictions of human, mouse and monkey MHC class I affinities for peptides of length 8-11. Nucleic Acids Res 2008; 36:W509-12.
75. Peters B, Sette A. Generating quantitative models describing the sequence specificity of biological processes with the stabilized matrix method. BMC Bioinformatics 2005; 6:132.
76. Sidney J, Assarsson E, Moore C, et al. Quantitative peptide binding motifs for 19 human and mouse MHC class I molecules derived using positional scanning combinatorial peptide libraries. Immunome Res 2008; 4:2.

77. Jagannathan P, Osborne C M, Royce C, et al. Comparisons of CD8+ T cells specific for human immunodeficiency virus, hepatitis C virus, and cytomegalovirus reveal differences in frequency, immunodominance, phenotype, and interleukin-2 responsiveness. J Virol 2009; 83:2728-42.
78. Day C L, Kaufmann D E, Kiepiela P, et al. PD-1 expression on HIV-specific T cells is associated with T-cell exhaustion and disease progression. Nature 2006; 443:350-4.
79. Kita H, Matsumura S, He X S, et al. Quantitative and functional analysis of PDC-E2-specific autoreactive cytotoxic T lymphocytes in primary biliary cirrhosis. J Clin Invest 2002; 109:1231-40.
80. Gershwin M E, Selmi C, Worman H J, et al. Risk factors and comorbidities in primary biliary cirrhosis: a controlled interview-based study of 1032 patients. Hepatology 2005; 42:1194-202.
81. Liang Y, Yang Z, Zhong R. Primary biliary cirrhosis and cancer risk: a systematic review and meta-analysis. Hepatology 2012; 56:1409-17.
82. Vergani D, Wells L, Larcher V F, et al. Genetically determined low C4: a predisposing factor to autoimmune chronic active hepatitis. Lancet 1985; 2:294-8.
83. Doherty D G, Underhill J A, Donaldson P T, et al. Polymorphism in the human complement C4 genes and genetic susceptibility to autoimmune hepatitis. Autoimmunity 1994; 18:243-9.
84. Irie J, Wu Y, Wicker L S, et al. NOD.c3c4 congenic mice develop autoimmune biliary disease that serologically and pathogenetically models human primary biliary cirrhosis. J Exp Med 2006; 203:1209-19.
85. Koarada S, Wu Y, Fertig N, et al. Genetic control of autoimmunity: protection from diabetes, but spontaneous autoimmune biliary disease in a nonobese diabetic congenic strain. J Immunol 2004; 173:2315-23.
86. Wakabayashi K, Lian Z X, Moritoki Y, et al. IL-2 receptor alpha(−/−) mice and the development of primary biliary cirrhosis. Hepatology 2006; 44:1240-9.
87. Oertelt S, Lian Z X, Cheng C M, et al. Anti-Mitochondrial Antibodies and Primary Biliary Cirrhosis in TGF-beta Receptor II Dominant-Negative Mice. J Immunol 2006; 177:1655-60.
88. Acha-Orbea H, Finke D, Attinger A, et al. Interplays between mouse mammary tumor virus and the cellular and humoral immune response. Immunol Rev 1999; 168: 287-303.
89. Held W, Shakhov A N, Waanders G, et al. An exogenous mouse mammary tumor virus with properties of Mls-la (Mtv-7). J Exp Med 1992; 175:1623-33.
90. Galley K. Danska J. Peri-Islet Infiltrates of Young Non-Obese Diabetic Mice Display Restricted TCR Beta-Chain Diversity. The Journal of Immunology 1995; 154: 2969-2982.
91. D'Acquisto F, Crompton T. CD3+CD4−CD8− (double negative) T cells: saviours or villains of the immune response? Biochem Pharmacol 2011; 82:333-40.
92. Bhan A K, Dienstag J L, Wands J R, et al. Alterations of T-cell subsets in primary biliary cirrhosis. Clin Exp Immunol 1982; 47:351-8.
93. M Seifi, J Jovel, R Pencek, et al. Obeticholic acid response in PBC associated with differential expression of antigen presentation, Wnt signalling and mRNA splicing [Abstract]. Journal of Hepatology 2018; 68:S446-S447.
94. Chen B, Khodadoust M S, Liu C L, et al. Profiling Tumor Infiltrating Immune Cells with CIBERSORT. Methods Mol Biol 2018; 1711:243-259.
95. Newman A M, Liu C L, Green M R, et al. Robust enumeration of cell subsets from tissue expression profiles. Nat Methods 2015; 12:453-7.
96. Han A, Glanville J, Hansmann L, et al. Linking T-cell receptor sequence to functional phenotype at the single-cell level. Nat Biotechnol 2014; 32:684-92.
97. Acha-Orbea H, Shakhov A N, Finke D. Immune response to MMTV infection. Front Biosci 2007; 12:1594-609.
98. Finke D, Acha-Orbea H. Differential migration of in vivo primed B and T lymphocytes to lymphoid and non-lymphoid organs. Eur J Immunol 2001; 31:2603-11.
99. Finke D. Mortezavi L, Acha-Orbea H. Preactivation of B lymphocytes does not enhance mouse mammary tumor virus infection. J Virol 1998; 72:7688-91.
100. Candando K M, Lykken J M, Tedder T F. B10 cell regulation of health and disease. Immunol Rev 2014; 259:259-72.
101. Iwata Y, Matsushita T, Horikawa M, et al. Characterization of a rare IL-10-competent B-cell subset in humans that parallels mouse regulatory B10 cells. Blood 2011; 117:530-41.
102. Ardavin C, Martin P, Ferrero I, et al. B cell response after MMTV infection: extrafollicular plasmablasts represent the main infected population and can transmit viral infection. J Immunol 1999; 162:2538-45.
103. Maecker H T, McCoy J P, Nussenblatt R. Standardizing immunophenotyping for the Human Immunology Project. Nat Rev Immunol 2012; 12:191-200.
104. Mauri C, Bosma A. Immune regulatory function of B cells. Annu Rev Immunol 2012; 30:221-41.
105. Shapiro-Shelef M, Calame K. Regulation of plasma-cell development. Nat Rev Immunol 2005; 5:230-42.
106. Allman D, Pillai S. Peripheral B cell subsets. Curr Opin Immunol 2008; 20:149-57.
107. Sharon D, Mason A. Role of Novel Retroviruses in Chronic Liver Disease: Assessing the Link of Human Betaretrovirus with Primary Biliary Cirrhosis. Current Infectious Disease Reports 2015:17; 460.
108. Hirschfield G M, Chapman R W, Karlsen T H, et al. The genetics of complex cholestatic disorders. Gastroenterology 2013; 144:1357-74.
109. Hirschfield G M, Liu X, Han Y. et al. Variants at IRF5-TNPO3, 17q12-21 and MMEL1 are associated with primary biliary cirrhosis. Nat Genet 2010; 42:655-7.
110. Hirschfield G M, Liu X, Xu C, et al. Primary biliary cirrhosis associated with HLA, IL12A, and IL12RB2 variants. N Engl J Med 2009, 360:2544-55.
111. Hirschfield G M, Xie G, Lu E, et al. Association of primary biliary cirrhosis with variants in the CLEC 6A, SOCS 1, SPIB and SIAE immunomodulatory genes. Genes and immunity 2012.
112. Juran B D, Hirschfield G M, Invernizzi P, et al. Immunochip analyses identify a novel risk locus for primary biliary cirrhosis at 13q 14, multiple independent associations at four established risk loci and epistasis between 1p31 and 7q32 risk variants. Hum Mol Genet 2012; 21:5209-21.
113. Liu X, Invernizzi P. Lu Y, et al. Genome-wide meta-analyses identify three loci associated with primary biliary cirrhosis. Nat Genet 2010; 42:658-60.
114. Hirschfield G M, Gershwin M E, Strauss R, et al. Phase 2 study evaluating the efficacy and safety of ustekinumab in patients with primary biliary cirrhosis who had an inadequate response to ursodeoxycholic acid. Journal of Hepatology 2014; 60:S189-190.

115. Pulickal A S, Hambleton S, Callaghan M J, et al. Biliary cirrhosis in a child with inherited interleukin-12 deficiency. Journal of tropical pediatrics 2008; 54:269-71.
116. Li P, Lu G, Cui Y, et al. Association of IL12A Expression Quantitative Trait Loci (eQTL) With Primary Biliary Cirrhosis in a Chinese Han Population. Medicine (Baltimore) 2016; 95:e3665.
117. Jovel J, Lin Z, O'Keefe S, et al. A Survey of Molecular Heterogeneity in Hepatocellular Carcinoma. Hepatol Commun 2018; 2:941-955.
118. Stavrou S, Crawford D, Blouch K, et al. Different modes of retrovirus restriction by human APOBEC3A and APOBEC3G in vivo. PLoS Pathog 2014; 10:e1004145.
119. MacMillan A L, *Kohli* R M, Ross S R. APOBEC3 inhibition of mouse mammary tumor virus infection: the role of cytidine deamination versus inhibition of reverse transcription. J Virol 2013; 87:4808-17.

---

What is claimed is:

1. A method for determination of previous history and/or presence of a betaretrovirus infection in a subject, the method comprising:
   obtaining a biological sample from the subject, the biological sample comprising immune effector-producing cells,
   incubating the biological sample with one or more betaretrovirus-specific epitopes, the betaretrovirus-specific epitopes comprising at least 7 contiguous amino acids from any one of SEQ ID Nos. 1-36; and
   measuring the production of one or more immune effectors by the immune effector-producing cells;
   wherein the subject has or had a betaretroviral infection when the level of the one or more immune effectors produced is one standard deviation or more from an equivalent control with no betaretroviral-specific epitope added.

2. The method of claim 1, wherein the determination of previous history and/or presence of betaretrovirus infection indicates the subject as having, or being at risk of having, cancer or liver disease.

3. The method of claim 2, wherein the cancer is breast cancer, or hematopoetic malignancy, or the liver disease is primary biliary cholangitis, autoimmune hepatitis, alcoholic liver disease, or cryptogenic cirrhosis.

4. The method of claim 3, wherein the hematopoetic malignancy is chronic lymphocytic leukemia (CLL), non-Hodgkins lymphoma, or plasma cell myeloma.

5. The method of claim 1, wherein the subject is diagnosed with an autoimmune disorder or neurodegenerative disease or suspected of having an autoimmune disorder or neurodegenerative disease.

6. The method of claim 5, wherein the autoimmune disorder is Crohn's disease or Systemic Lupus Erythematosus and the neurodegenerative disease is Parkinson's disease or Alzheimer's disease.

7. The method of claim 1 wherein the biological sample comprises whole blood or purified leukocytes or lymphocytes obtained from the subject.

8. The method of claim 7 wherein the leukocytes are intrahepatic lymphocytes.

9. The method of claim 1 wherein the immune effector-producing cells are CD8+ T-cells.

10. The method of claim 1, wherein the one or more immune effectors produced comprise interferon-gamma, TNF-alpha, or a combination thereof.

11. The method of claim 10, wherein the one or more immune effectors produced is interferon-gamma and the threshold for the subject having or having had a betaretroviral infection is about 10 picograms/ml or greater.

12. The method of claim 1, further comprising treating the subject that exhibits the history and/or presence of betaretrovirus infection.

13. The method of claim 12, in which the treatment comprises anti-cancer therapy, anti-viral therapy or a combination thereof.

14. The method of claim 13, in which the anti-viral therapy comprises combination antiretroviral therapy (cART).

15. The method of claim 1, wherein the quantity of the one or more immune effectors produced is two or more standard deviations from an equivalent control without a betaretroviral-specific epitope added.

16. The method of claim 1, wherein the quantity of the one or more immune effectors produced is three or more standard deviations from an equivalent control without a betaretroviral-specific epitope added.

* * * * *